(12) United States Patent
McDaniel et al.

(10) Patent No.: US 8,937,041 B2
(45) Date of Patent: Jan. 20, 2015

(54) MACROCYCLIC HEPATITIS C SERINE PROTEASE INHIBITORS

(75) Inventors: Keith F. McDaniel, Wauconda, IL (US); Hui-Ju Chen, Grayslake, IL (US); Ming Yeung, Grayslake, IL (US); Timothy Middleton, Elkhorn, WI (US); Liangjun Lu, Kildeer, IL (US); Kevin Kurtz, Kenosha, WI (US)

(73) Assignee: AbbVie, Inc., North Chicago, IL (US)

( * ) Notice: Subject to any disclaimer, the term of this patent is extended or adjusted under 35 U.S.C. 154(b) by 83 days.

(21) Appl. No.: 13/339,440

(22) Filed: Dec. 29, 2011

(65) Prior Publication Data

US 2012/0172291 A1    Jul. 5, 2012

Related U.S. Application Data

(60) Provisional application No. 61/428,446, filed on Dec. 30, 2010.

(51) Int. Cl.
*A61K 38/00* (2006.01)
*C07K 5/08* (2006.01)
*C07K 5/083* (2006.01)

(52) U.S. Cl.
CPC ............. *C07K 5/0804* (2013.01); *C07K 5/0827* (2013.01); *A61K 38/00* (2013.01)
USPC ........................................................ 514/4.3

(58) Field of Classification Search
CPC ..... A61K 38/00; C07K 5/0804; C07K 5/0827
See application file for complete search history.

(56) References Cited

U.S. PATENT DOCUMENTS

| | | | |
|---|---|---|---|
| 5,831,002 A | 11/1998 | Haupt et al. |
| 6,268,207 B1 | 7/2001 | Bailey |
| 6,323,180 B1 | 11/2001 | Llinas-Brunet et al. |
| 6,329,379 B1 | 12/2001 | Llinas-Brunet et al. |
| 6,329,417 B1 | 12/2001 | Llinas-Brunet et al. |
| 6,410,531 B1 | 6/2002 | Llinas-Brunet et al. |
| 6,420,380 B2 | 7/2002 | Llinas-Brunet et al. |
| 6,534,523 B1 | 3/2003 | Llinas-Brunet et al. |
| 6,608,027 B1 | 8/2003 | Tsantrizos et al. |
| 6,642,204 B2 | 11/2003 | Llinas-Brunet et al. |
| 6,653,295 B2 | 11/2003 | Glunz et al. |
| 6,699,855 B2 | 3/2004 | Zhang et al. |
| 6,727,366 B2 | 4/2004 | Han et al. |
| 6,767,991 B1 | 7/2004 | Llinas-Brunet et al. |
| 6,774,212 B2 | 8/2004 | Han |
| 6,803,374 B2 | 10/2004 | Priestley et al. |
| 6,846,806 B2 | 1/2005 | Priestley |
| 6,867,185 B2 | 3/2005 | Campbell et al. |
| 6,869,964 B2 | 3/2005 | Campbell et al. |
| 6,872,805 B2 | 3/2005 | Campbell et al. |
| 6,878,722 B2 | 4/2005 | Campbell et al. |
| 6,939,854 B2 | 9/2005 | Priestley |
| 6,995,174 B2 | 2/2006 | Wang et al. |
| 7,037,911 B2 | 5/2006 | Zhang |
| 7,041,698 B2 | 5/2006 | Ripka et al. |
| 7,091,184 B2 | 8/2006 | Llinas-Brunet et al. |
| 7,112,601 B2 | 9/2006 | Glunz et al. |
| 7,119,072 B2 | 10/2006 | Llinas-Brunet et al. |
| 7,122,627 B2 | 10/2006 | Priestley et al. |
| 7,132,504 B2 | 11/2006 | Scola et al. |
| 7,135,462 B2 | 11/2006 | Scola et al. |
| 7,153,848 B2 | 12/2006 | Hudyma et al. |
| 7,157,424 B2 | 1/2007 | Chen et al. |
| 7,173,004 B2 | 2/2007 | McPhee et al. |
| 7,176,208 B2 | 2/2007 | Nakajima et al. |
| 7,183,302 B2 | 2/2007 | Romine et al. |
| 7,189,844 B2 | 3/2007 | Gallou et al. |
| 7,309,708 B2 | 12/2007 | Tu et al. |
| 7,323,447 B2 | 1/2008 | Sin et al. |
| 7,348,425 B2 | 3/2008 | Hudyma et al. |
| 7,368,452 B2 | 5/2008 | Nakajima et al. |
| 7,375,218 B2 | 5/2008 | Gallou |
| 7,491,794 B2 | 2/2009 | Blatt et al. |
| 7,504,378 B2 | 3/2009 | Llinas-Brunet et al. |
| 7,544,798 B2 | 6/2009 | Busacca et al. |
| 7,566,719 B2 | 7/2009 | Nakajima et al. |
| 7,592,419 B2 | 9/2009 | Venkatraman et al. |
| 7,601,709 B2 | 10/2009 | Miao et al. |
| 7,608,590 B2 | 10/2009 | Rosenquist et al. |
| 7,642,235 B2 | 1/2010 | Llinas-Brunet et al. |
| 7,642,339 B2 | 1/2010 | Chaudhary et al. |
| 7,659,245 B2 | 2/2010 | Simmen et al. |

(Continued)

FOREIGN PATENT DOCUMENTS

| | | |
|---|---|---|
| EP | 1437362 A1 | 7/2004 |
| EP | 1455809 | 6/2011 |

(Continued)

OTHER PUBLICATIONS

International Search Report for corresponding PCT International Application No. PCT/US09/05082 dated Apr. 1, 2010.
Lu, Liangjun, et al., "Mutations Conferring Resistance to a Potent Hepatitis C Virus Serine Protease Inhibitor In Vitro," Antimicrobial Agents and Chemotherapy, Jun. 2004, vol. 48, No. 6, pp. 2260-2266.
A. Johansson et al., "Acyl Sulfonamides as Potent protease Inhibitors of the Hepatitis C Virus Full-Length NS3 (Protease-Helicase/NTPase): A Comparative Study of Different C-Terminals", Bioorganic & Medicinal Chemistry, vol. 11, pp. 2251-2568 (2003).

(Continued)

*Primary Examiner* — Thomas S Heard
(74) *Attorney, Agent, or Firm* — Edwards Wildman Palmer LLP; Jeffrey D. Hsi; Stephen W. Rafferty

(57) ABSTRACT

The present invention relates to novel fluorinated macrocyclic compounds and methods of treating a hepatitis C infection in a subject in need of such therapy with said macrocyclic compounds. The present invention further relates to pharmaceutical compositions comprising the compounds of the present invention, or pharmaceutically acceptable salts, esters, or prodrugs thereof, in combination with a pharmaceutically acceptable carrier or excipient.

18 Claims, No Drawings

(56) References Cited

U.S. PATENT DOCUMENTS

| | | |
|---|---|---|
| 7,687,459 B2 | 3/2010 | Niu et al. |
| 7,741,281 B2 | 6/2010 | D'Andrea et al. |
| 7,763,584 B2 | 7/2010 | Wang et al. |
| 7,772,180 B2 | 8/2010 | Sin et al. |
| 7,772,183 B2 | 8/2010 | Carini et al. |
| 7,829,665 B2 | 11/2010 | Blatt et al. |
| 2002/0016442 A1 | 2/2002 | Llinas-brunet et al. |
| 2002/0037998 A1 | 3/2002 | Llinas-Brunet et al. |
| 2002/0111313 A1 | 8/2002 | Campbell et al. |
| 2003/0181363 A1 | 9/2003 | Llinas-Brunet et al. |
| 2003/0186895 A1 | 10/2003 | Llinas-Brunet et al. |
| 2003/0187018 A1 | 10/2003 | Llinas-Brunet et al. |
| 2003/0191067 A1 | 10/2003 | Llinas-Brunet et al. |
| 2003/0224977 A1 | 12/2003 | Llinas-Brunet et al. |
| 2003/0232386 A1 | 12/2003 | Shah et al. |
| 2004/0002448 A1 | 1/2004 | Tsantrizos et al. |
| 2004/0038872 A1 | 2/2004 | Campbell et al. |
| 2004/0048802 A1 | 3/2004 | Ripka et al. |
| 2004/0058982 A1 | 3/2004 | Harris |
| 2004/0106559 A1 | 6/2004 | Wang et al. |
| 2004/0180815 A1 | 9/2004 | Nakajima et al. |
| 2004/0229776 A1 | 11/2004 | Chen et al. |
| 2004/0229777 A1 | 11/2004 | Cerreta et al. |
| 2004/0229818 A1 | 11/2004 | Llinas-Brunet |
| 2004/0248779 A1 | 12/2004 | Dersch et al. |
| 2004/0248806 A1 | 12/2004 | Temsamani et al. |
| 2004/0266668 A1 | 12/2004 | Nakajima et al. |
| 2005/0020503 A1 | 1/2005 | Llinas-Brunet et al. |
| 2005/0049187 A1 | 3/2005 | Brandenburg et al. |
| 2005/0065073 A1 | 3/2005 | Wu et al. |
| 2005/0075279 A1 | 4/2005 | Llinas-Brunet et al. |
| 2005/0080005 A1 | 4/2005 | Llinas-Brunet et al. |
| 2005/0090432 A1 | 4/2005 | McPhee et al. |
| 2005/0119168 A1 | 6/2005 | Venkatraman et al. |
| 2005/0143316 A1 | 6/2005 | Tu et al. |
| 2005/0148085 A1 | 7/2005 | Larsen |
| 2005/0153877 A1 | 7/2005 | Miao et al. |
| 2005/0153900 A1 | 7/2005 | Velazquez et al. |
| 2005/0164921 A1 | 7/2005 | Njoroge et al. |
| 2005/0192212 A1 | 9/2005 | Llinas-Brunet et al. |
| 2005/0209135 A1 | 9/2005 | Busacca et al. |
| 2005/0214366 A1 | 9/2005 | Harris |
| 2005/0215423 A1 | 9/2005 | Brenner et al. |
| 2005/0222045 A1 | 10/2005 | Auvin et al. |
| 2005/0267018 A1 | 12/2005 | Blatt et al. |
| 2005/0267151 A1 | 12/2005 | Busacca et al. |
| 2006/0009667 A1 | 1/2006 | Herweck et al. |
| 2006/0019905 A1 | 1/2006 | Bailey et al. |
| 2006/0046965 A1 | 3/2006 | Bailey et al. |
| 2006/0063915 A1 | 3/2006 | Gallou et al. |
| 2006/0063916 A1 | 3/2006 | Gallou |
| 2006/0068007 A1 | 3/2006 | Li et al. |
| 2006/0089300 A1 | 4/2006 | Llinas-Brunet et al. |
| 2006/0122123 A1 | 6/2006 | Chaudhary et al. |
| 2006/0166893 A1 | 7/2006 | Auvin et al. |
| 2006/0172950 A1 | 8/2006 | Wang et al. |
| 2006/0199773 A1 | 9/2006 | Sausker et al. |
| 2006/0205638 A1 | 9/2006 | Busacca et al. |
| 2006/0257980 A1 | 11/2006 | Li |
| 2006/0258868 A1 | 11/2006 | Bailey et al. |
| 2006/0275366 A1 | 12/2006 | Malcolm et al. |
| 2006/0276405 A1 | 12/2006 | Albrecht |
| 2006/0276407 A1 | 12/2006 | Albrecht et al. |
| 2006/0281688 A1 | 12/2006 | Zhang et al. |
| 2007/0004635 A1 | 1/2007 | Albrecht et al. |
| 2007/0010431 A1 | 1/2007 | Malcolm et al. |
| 2007/0010455 A1 | 1/2007 | Hewawasam et al. |
| 2007/0060510 A1 | 3/2007 | Nakajima et al. |
| 2007/0060565 A1 | 3/2007 | Meanwell et al. |
| 2007/0072809 A1 | 3/2007 | Cho et al. |
| 2007/0078081 A1 | 4/2007 | Casarez et al. |
| 2007/0078122 A1 | 4/2007 | Bergstrom et al. |
| 2007/0093414 A1 | 4/2007 | Carini et al. |
| 2007/0099825 A1 | 5/2007 | D'Andrea et al. |
| 2007/0161575 A1 | 7/2007 | Miao et al. |
| 2007/0179167 A1 | 8/2007 | Cottrell et al. |
| 2007/0184024 A1 | 8/2007 | Meanwell et al. |
| 2007/0185083 A1 | 8/2007 | Bergstrom et al. |
| 2007/0237818 A1 | 10/2007 | Malcolm et al. |
| 2007/0243166 A1 | 10/2007 | Llinas-Brunet et al. |
| 2007/0249637 A1 | 10/2007 | Collins et al. |
| 2007/0258947 A1 | 11/2007 | Njoroge et al. |
| 2007/0270405 A1 | 11/2007 | Bender et al. |
| 2007/0270406 A1 | 11/2007 | Gentles et al. |
| 2007/0275930 A1 | 11/2007 | Gentles et al. |
| 2007/0281884 A1 | 12/2007 | Sun et al. |
| 2007/0281885 A1 | 12/2007 | Sun et al. |
| 2007/0287664 A1 | 12/2007 | Ralston et al. |
| 2007/0287694 A1 | 12/2007 | Yeung et al. |
| 2007/0299078 A1 | 12/2007 | Niu et al. |
| 2008/0008681 A1 | 1/2008 | Niu et al. |
| 2008/0014173 A1 | 1/2008 | Scola et al. |
| 2008/0032936 A1 | 2/2008 | Gai et al. |
| 2008/0038225 A1 | 2/2008 | Sun et al. |
| 2008/0039375 A1 | 2/2008 | Moore et al. |
| 2008/0039470 A1 | 2/2008 | Niu et al. |
| 2008/0045536 A1 | 2/2008 | Vaccaro et al. |
| 2008/0107623 A1 | 5/2008 | D'Andrea et al. |
| 2008/0107624 A1 | 5/2008 | D'Andrea et al. |
| 2008/0107625 A1 | 5/2008 | D'Andrea et al. |
| 2008/0108632 A1 | 5/2008 | Lin et al. |
| 2008/0119461 A1 | 5/2008 | Sin et al. |
| 2008/0145334 A1 | 6/2008 | Wang et al. |
| 2008/0146537 A1 | 6/2008 | Bender et al. |
| 2008/0152619 A1 | 6/2008 | Sin et al. |
| 2008/0152622 A1 | 6/2008 | Nakajima et al. |
| 2008/0159982 A1 | 7/2008 | Wang et al. |
| 2008/0171015 A1 | 7/2008 | Bender et al. |
| 2008/0181868 A1 | 7/2008 | Sun et al. |
| 2008/0200497 A1 | 8/2008 | Bailey et al. |
| 2008/0242835 A1 | 10/2008 | Shu |
| 2008/0267916 A1 | 10/2008 | Gai et al. |
| 2008/0267917 A1 | 10/2008 | Niu et al. |
| 2008/0269228 A1 | 10/2008 | Moore et al. |
| 2008/0269502 A1 | 10/2008 | Gantz et al. |
| 2008/0279821 A1 | 11/2008 | Niu et al. |
| 2008/0311077 A1 | 12/2008 | Chaudhary et al. |
| 2009/0005387 A1 | 1/2009 | Niu et al. |
| 2009/0035271 A1 | 2/2009 | Sun et al. |
| 2009/0036708 A1 | 2/2009 | Jia et al. |
| 2009/0041721 A1 | 2/2009 | Niu et al. |
| 2009/0047252 A1 | 2/2009 | Cai et al. |
| 2009/0075869 A1 | 3/2009 | Holloway et al. |
| 2009/0093533 A1 | 4/2009 | Beigelman et al. |
| 2009/0105471 A1 | 4/2009 | Blatt et al. |
| 2009/0111757 A1 | 4/2009 | Lin et al. |
| 2009/0111969 A1 | 4/2009 | Blatt et al. |
| 2009/0111982 A1 | 4/2009 | Blatt et al. |
| 2009/0124808 A1 | 5/2009 | Busacca et al. |
| 2009/0130059 A1 | 5/2009 | Sun et al. |
| 2009/0148407 A1 | 6/2009 | Blatt et al. |
| 2009/0149491 A1 | 6/2009 | Liu et al. |
| 2009/0155209 A1 | 6/2009 | Blatt et al. |
| 2009/0162318 A1 | 6/2009 | Bender et al. |
| 2009/0163706 A1 | 6/2009 | Hildbrand et al. |
| 2009/0169510 A1 | 7/2009 | Blatt et al. |
| 2009/0175822 A1 | 7/2009 | Moore et al. |
| 2009/0176858 A1 | 7/2009 | Niu et al. |
| 2009/0180981 A1 | 7/2009 | Niu et al. |
| 2009/0186869 A1 | 7/2009 | Cottell et al. |
| 2009/0191153 A1 | 7/2009 | Sun et al. |
| 2009/0202480 A1 | 8/2009 | Parsy et al. |
| 2009/0257978 A1 | 10/2009 | Cho et al. |
| 2009/0269305 A1 | 10/2009 | Seiwert et al. |
| 2009/0274648 A1 | 11/2009 | Wang et al. |
| 2009/0274652 A1 | 11/2009 | Sin et al. |
| 2009/0281141 A1 | 11/2009 | Simmen et al. |
| 2009/0285773 A1 | 11/2009 | Sun et al. |
| 2009/0285774 A1 | 11/2009 | Sin et al. |
| 2009/0286814 A1 | 11/2009 | Lin et al. |
| 2009/0286843 A1 | 11/2009 | Blatt et al. |
| 2009/0297472 A1 | 12/2009 | Wang et al. |
| 2009/0304626 A1 | 12/2009 | Wang et al. |
| 2009/0304629 A1 | 12/2009 | Miao et al. |

(56) References Cited

U.S. PATENT DOCUMENTS

| | | |
|---|---|---|
| 2009/0306085 A1 | 12/2009 | Petter et al. |
| 2009/0326194 A1 | 12/2009 | Busacca et al. |
| 2010/0015092 A1 | 1/2010 | Nakajima et al. |
| 2010/0018355 A1 | 1/2010 | Crawford |
| 2010/0022578 A1 | 1/2010 | Raboisson et al. |
| 2010/0028300 A1 | 2/2010 | Llinas-Brunet et al. |
| 2010/0036116 A1 | 2/2010 | Scalone et al. |
| 2010/0041591 A1 | 2/2010 | Niu et al. |
| 2010/0041728 A1 | 2/2010 | Antonov et al. |
| 2010/0068182 A1 | 3/2010 | Huang et al. |
| 2010/0069294 A1 | 3/2010 | Petter et al. |
| 2010/0074890 A1 | 3/2010 | Hagel et al. |
| 2010/0080770 A1 | 4/2010 | Hiebert et al. |
| 2010/0080771 A1 | 4/2010 | Hiebert et al. |
| 2010/0081700 A1 | 4/2010 | Wang et al. |
| 2010/0081713 A1 | 4/2010 | Sharma et al. |
| 2010/0093792 A1 | 4/2010 | Berkenbusch et al. |
| 2010/0099695 A1 | 4/2010 | Liverton et al. |
| 2010/0113440 A1 | 5/2010 | Belfrage et al. |
| 2010/0124545 A1 | 5/2010 | Zhang et al. |
| 2010/0144608 A1 | 6/2010 | Ku et al. |
| 2010/0150866 A1 | 6/2010 | Wang et al. |
| 2010/0160403 A1 | 6/2010 | Link et al. |
| 2010/0168384 A1 | 7/2010 | McDaniel et al. |
| 2010/0196321 A1 | 8/2010 | Cooper et al. |
| 2010/0240698 A1 | 9/2010 | Simmen et al. |
| 2010/0260710 A1 | 10/2010 | Parsy et al. |
| 2010/0272674 A1 | 10/2010 | Hiebert et al. |
| 2010/0292219 A1 | 11/2010 | Agarwal et al. |
| 2010/0297079 A1 | 11/2010 | Almond et al. |
| 2011/0020272 A1 | 1/2011 | Schubert |
| 2011/0059047 A1 | 3/2011 | Seiwert et al. |
| 2011/0065737 A1 | 3/2011 | Liu et al. |
| 2011/0178107 A1 | 7/2011 | Wang et al. |

FOREIGN PATENT DOCUMENTS

| | | |
|---|---|---|
| WO | 96/40751 A1 | 12/1996 |
| WO | 96/40752 A1 | 12/1996 |
| WO | 99/07733 A2 | 2/1999 |
| WO | 00/09543 A2 | 2/2000 |
| WO | 00/09558 A1 | 2/2000 |
| WO | 00/59929 A1 | 10/2000 |
| WO | 02/060926 A2 | 8/2002 |
| WO | 03/053349 A2 | 7/2003 |
| WO | 03/064416 A1 | 8/2003 |
| WO | 03/064455 A2 | 8/2003 |
| WO | 03/064456 A1 | 8/2003 |
| WO | 03/066103 A1 | 8/2003 |
| WO | 03/099274 A1 | 12/2003 |
| WO | 2004/030670 A1 | 4/2004 |
| WO | 2004/037855 A1 | 5/2004 |
| WO | 2004/039833 A1 | 5/2004 |
| WO | 2004/072243 A2 | 8/2004 |
| WO | 2004/087741 A1 | 10/2004 |
| WO | 2004/089974 A1 | 10/2004 |
| WO | 2004/092203 A2 | 10/2004 |
| WO | 2004/093798 A2 | 11/2004 |
| WO | 2004/093915 A1 | 11/2004 |
| WO | 2004/094452 A2 | 11/2004 |
| WO | 2004/103996 A1 | 12/2004 |
| WO | 2005/028501 A1 | 3/2005 |
| WO | 2005/037214 A2 | 4/2005 |
| WO | 2005/046712 A1 | 5/2005 |
| WO | 2005/051410 A1 | 6/2005 |
| WO | 2005/051980 A1 | 6/2005 |
| WO | 2005/054430 A2 | 6/2005 |
| WO | 2005/070955 A1 | 8/2005 |
| WO | 2005/075502 A1 | 8/2005 |
| WO | 2005/090383 A2 | 9/2005 |
| WO | 2005/095403 A2 | 10/2005 |
| WO | 2005/116054 A1 | 12/2005 |
| WO | 2006/000085 A1 | 1/2006 |
| WO | 2006/005479 A2 | 1/2006 |
| WO | 2006/020276 A2 | 2/2006 |
| WO | 2006/033851 A1 | 3/2006 |
| WO | 2006/033878 A1 | 3/2006 |
| WO | 2006/036614 A2 | 4/2006 |
| WO | 2006/096652 A2 | 9/2006 |
| WO | 2006/114405 A2 | 11/2006 |
| WO | 2006/119061 A2 | 11/2006 |
| WO | 2006/122188 A2 | 11/2006 |
| WO | 2006/128455 A2 | 12/2006 |
| WO | 2006/130552 A2 | 12/2006 |
| WO | 2006/130553 A2 | 12/2006 |
| WO | 2006/130607 A2 | 12/2006 |
| WO | 2006/130626 A2 | 12/2006 |
| WO | 2006/130627 A2 | 12/2006 |
| WO | 2006/130628 A2 | 12/2006 |
| WO | 2006/130666 A2 | 12/2006 |
| WO | 2006/130686 A2 | 12/2006 |
| WO | 2006/130687 A2 | 12/2006 |
| WO | 2006/130688 A2 | 12/2006 |
| WO | 2007/001406 A2 | 1/2007 |
| WO | 2007/005838 A1 | 1/2007 |
| WO | 2007/008657 A2 | 1/2007 |
| WO | 2007/009109 A2 | 1/2007 |
| WO | 2007/009227 A1 | 1/2007 |
| WO | 2007/014919 A1 | 2/2007 |
| WO | 2007/014921 A1 | 2/2007 |
| WO | 2007/014923 A1 | 2/2007 |
| WO | 2007/014924 A1 | 2/2007 |
| WO | 2007/014925 A1 | 2/2007 |
| WO | 2007/014926 A1 | 2/2007 |
| WO | 2007/015824 A2 | 2/2007 |
| WO | 2007/016441 A1 | 2/2007 |
| WO | 2007/030656 A1 | 3/2007 |
| WO | 2007/044893 A2 | 4/2007 |
| WO | 2007/044933 A1 | 4/2007 |
| WO | 2007/056120 A1 | 5/2007 |
| WO | 2007/131966 A1 | 11/2007 |
| WO | 2007/139585 A1 | 12/2007 |
| WO | 2007/143694 A2 | 12/2007 |
| WO | 2007/148135 A1 | 12/2007 |
| WO | 2008/002924 A2 | 1/2008 |
| WO | 2008/008502 A1 | 1/2008 |
| WO | 2008/008776 A2 | 1/2008 |
| WO | 2008/019289 A2 | 2/2008 |
| WO | 2008/019303 A2 | 2/2008 |
| WO | 2008/021956 A2 | 2/2008 |
| WO | 2008/021960 A2 | 2/2008 |
| WO | 2008/022006 A2 | 2/2008 |
| WO | 2008/039538 A2 | 4/2008 |
| WO | 2008/046860 A2 | 4/2008 |
| WO | 2008/051475 A2 | 5/2008 |
| WO | 2008/051514 A2 | 5/2008 |
| WO | 2008/057208 A2 | 5/2008 |
| WO | 2008/057209 A1 | 5/2008 |
| WO | 2008/057871 A2 | 5/2008 |
| WO | 2008/057873 A2 | 5/2008 |
| WO | 2008/057875 A2 | 5/2008 |
| WO | 2008/057995 A2 | 5/2008 |
| WO | 2008/059046 A1 | 5/2008 |
| WO | 2008/060927 A2 | 5/2008 |
| WO | 2008/062457 A2 | 5/2008 |
| WO | 2008/064057 A1 | 5/2008 |
| WO | 2008/064061 A1 | 5/2008 |
| WO | 2008/064066 A1 | 5/2008 |
| WO | 2008/070733 A2 | 6/2008 |
| WO | 2008/086161 A1 | 7/2008 |
| WO | 2008/092954 A2 | 8/2008 |
| WO | 2008/095058 A1 | 8/2008 |
| WO | 2008/096001 A1 | 8/2008 |
| WO | 2008/098368 A1 | 8/2008 |
| WO | 2008/101665 A1 | 8/2008 |
| WO | 2008/106130 A2 | 9/2008 |
| WO | 2008/114006 A1 | 9/2008 |
| WO | 2008/124384 A2 | 10/2008 |
| WO | 2008/128921 A1 | 10/2008 |
| WO | 2008/137779 A2 | 11/2008 |
| WO | 2008/141227 A1 | 11/2008 |
| WO | 2009/005676 A2 | 1/2009 |
| WO | 2009/005677 A2 | 1/2009 |

(56) References Cited

FOREIGN PATENT DOCUMENTS

| | | |
|---|---|---|
| WO | 2009/010804 A1 | 1/2009 |
| WO | 2009/014730 A1 | 1/2009 |
| WO | 2009/053828 A2 | 4/2009 |
| WO | 2009/067108 A1 | 5/2009 |
| WO | 2009/070689 A1 | 6/2009 |
| WO | 2009/070692 A1 | 6/2009 |
| WO | 2009/073713 A1 | 6/2009 |
| WO | 2009/073719 A1 | 6/2009 |
| WO | 2009/073780 A1 | 6/2009 |
| WO | 2009/080542 A1 | 7/2009 |
| WO | 2009/082697 A1 | 7/2009 |
| WO | 2009/082701 A1 | 7/2009 |
| WO | 2009/085659 A1 | 7/2009 |
| WO | 2009094443 A1 | 7/2009 |
| WO | 2009/099596 A2 | 8/2009 |
| WO | 2009/129109 A1 | 10/2009 |
| WO | 2009/137432 A1 | 11/2009 |
| WO | 2009/139792 A1 | 11/2009 |
| WO | 2009/140475 A1 | 11/2009 |
| WO | 2009/140500 A1 | 11/2009 |
| WO | 2009/142842 A2 | 11/2009 |
| WO | 2009/146347 A1 | 12/2009 |
| WO | 2009/148923 A1 | 12/2009 |
| WO | 2009/149377 A1 | 12/2009 |
| WO | 2010/000459 A1 | 1/2010 |
| WO | 2010/015545 A1 | 2/2010 |
| WO | 2010/021717 A2 | 2/2010 |
| WO | 2010/028236 A1 | 3/2010 |
| WO | 2010/033443 A1 | 3/2010 |
| WO | 2010/033444 A1 | 3/2010 |
| WO | 2010/033466 A1 | 3/2010 |
| WO | 2010/034105 A1 | 4/2010 |
| WO | 2010/036551 A1 | 4/2010 |
| WO | 2010/036871 A1 | 4/2010 |
| WO | 2010/036896 A1 | 4/2010 |
| WO | 2010/042834 A1 | 4/2010 |
| WO | 2010/048468 A1 | 4/2010 |
| WO | 2010/059667 A1 | 5/2010 |
| WO | 2010/059937 A1 | 5/2010 |
| WO | 2010/065577 A1 | 6/2010 |
| WO | 2010/077783 A1 | 7/2010 |
| WO | 2010/080389 A1 | 7/2010 |
| WO | 2010/088394 A1 | 8/2010 |
| WO | 2010/118078 A1 | 10/2010 |
| WO | 2010/120476 A2 | 10/2010 |
| WO | 2010/128521 A2 | 11/2010 |
| WO | 2010/135520 A1 | 11/2010 |
| WO | 2010/135748 A1 | 11/2010 |
| WO | 2011/017389 A1 | 2/2011 |
| WO | 2011/063501 A1 | 6/2011 |
| WO | 2011/063502 A1 | 6/2011 |

OTHER PUBLICATIONS

N. Goudreau et al., "NMR Structural Characterization of Peptide Inhibitors Bound to the Hepatitis C virus NS3 Protease: Design of New P2 Substituent", J. Med. Chem., vol. 47, pp. 123-132 (2004).

N. Goudreau et al., "The terapeutic potential of NS3 protease inhibitors in HCV infection", Expert Opin. Investig. Drugs, 14(9), pp. 1129-1144 (2005).

J. Rancourt et al., "Peptide-Based Inhibitors of the Hepatitis C Virus NS3 Protease: Structure-Activity Relationship at the C-Terminal Position", J. Med. Chem., vol. 47, pp. 2511-2522 (2004).

B.W. Dymock et al., "Emerging therapies for hepatitis C virus infection", Emerging Drugs—Ashley Publications Ltd., 6(1), pp. 13-42 (2001).

M. Llinás-Brunet et al., "Peptide-Based Inhibitors of the Hepatitis C Virus Serine Protease", Bioorganic & Medicinal Chemistry Letters 8, pp. 1713-1718 (1998)

Y.S. Tsantrizos et al., "Macrocyclic Inhibitors of the NS3 Protease as potential Therapeutic Agents of Hepatitis C Virus Infection", Angew. Chem. Int. Ed., 42(12), pp. 1355-1360 (2003).

J.L. Kim et al., "Crystal Structure of the Hepatitis C Virus NS3 Protease Domain Complexed with a Synthetic NS4A Cofactor Peptide", Cell, vol. 87, pp. 343-355 (1996).

G. Barbato et al., "Inhibitor binding induces active site stabilization of the HCV NS3 protein serine protease domain", The EMBO Journal, 19(6), pp. 1195-1206 (2000).

P. Ettmayer et al., J. Med. Chem., 47(10), pp. 2393-2404 (2004).

Y. Singh et al., "Recent Trends in targeted Anticancer Prodrug and Conjugate", DesignCurr Med. Chem., 15(18), pp. 1802-1826 (2008).

C.E. Muller et al., "Prodrug Approaches for Enhancing the Bioavailability of Drugs with Low Solubility", Chemistry & Biodiversity, vol. 6, pp. 2071-2083(2009).

Beaumont et al., "Design of Ester Prodrugs ot Enhance Oral Absorption of Poorly Permeable Compounds: Challenges to the Discovery Scientist", Current Drug Metabolism, vol. 4, pp. 461-485 (2003).

H.K. Han et al., AAPS Pharmsci.—Article 6, 2(1), pp. 1-11 (2000).

Testa et al., "Prodrug Research: Futile or Fertile?", Biochemical Pharmacology, pp. 2097-2106 (2004).

R. Ronn et al., "Exploration of acyl sulfonamides as carboxylic acid replacements in protease inhibitors of the hepatitis C virus full-length NS3", Bioorganic & Medicinal Chemistry, vol. 14, pp. 544-559 (2006).

International Search Report for corresponding PCT International Application No. PCT/US2011/067699 dated Sep. 3, 2012.

Supplementary European Search Report for corresponding European Patent Application No. 11883822.2 dated Jun. 27, 2014.

MACROCYCLIC HEPATITIS C SERINE PROTEASE INHIBITORS

RELATED APPLICATIONS

This application claims the benefit of U.S. Provisional application 61/428,446, filed on Dec. 30, 2010. The entire contents of the above application are incorporated herein by reference.

JOINT RESEARCH AGREEMENT

Inventions described in this application were made by or on behalf of Abbott Laboratories and Enanta Pharmaceuticals, Inc. whom are parties to a joint research agreement, that was in effect on or before the date such inventions were made and such inventions were made as a result of activities undertaken within the scope of the joint research agreement.

TECHNICAL FIELD

The present invention relates to novel fluorinated macrocycles having activity against the hepatitis C virus (HCV) and useful in the treatment of HCV infections. More particularly, the invention relates to macrocyclic compounds, compositions containing such compounds and methods for using the same, as well as processes for making such compounds.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which often have significant side effects.

SUMMARY OF THE INVENTION

The present invention relates to novel macrocyclic compounds and methods of treating a hepatitis C infection in a subject in need of such therapy with said macrocyclic compounds. The compounds of the present invention interfere with the life cycle of the hepatitis C virus and are useful as antiviral agents. The present invention further relates to pharmaceutical compositions comprising the compounds of the present invention, or pharmaceutically acceptable salts, esters or prodrugs thereof, in combination with a pharmaceutically acceptable carrier or excipient.

In one aspect, the invention provides a compound of formula I:

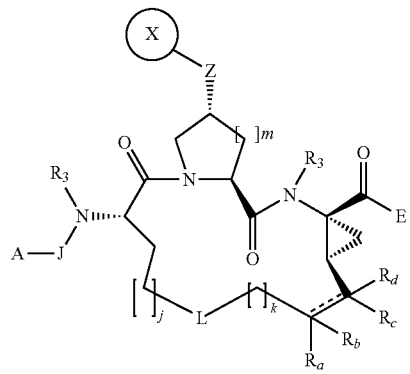

(I)

or pharmaceutically acceptable salts, esters, hydrates, solvates, polymorphs, or prodrugs thereof,
wherein:

X is an optionally substituted carbocyclic, optionally substituted heterocyclyl, optionally substituted aryl, or optionally substituted heteroaryl;

Z is O, $S(O)_m$, $NR_x$, OC(O), C(O), C(O)O, $NR_xC(O)$, or $C(O)NR_x$;

each $R_x$ is independently H or alkyl;

J is —C(O)—, —O—C(O)—, —C(O)O—, —N($R_3$)—C(O)—, —C(S)—, —C(=$NR_4$)—, —N($R_3$)—, —S(O)—, or —S($O_2$)— or absent;

A is selected from the group consisting of the following:
(i) H, aryl; substituted aryl; heteroaryl; substituted heteroaryl;
(ii) heterocyclyl or substituted heterocyclyl; and
(iii) —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; substituted —$C_1$-$C_8$ alkyl, substituted —$C_2$-$C_8$ alkenyl or substituted —$C_2$-$C_8$ alkynyl, each containing 0, 1, 2, or 3 heteroatoms independently selected from O, S and N; —$C_3$-$C_{12}$ carbocyclic, substituted —$C_3$-$C_{12}$ carbocyclic; —$C_3$-$C_{12}$ cycloalkenyl, or substituted —$C_3$-$C_{12}$ cycloalkenyl;

E is -G-$R_5$;

wherein G is absent; optionally substituted alkylene, optionally substituted alkenylene, optionally substituted alkynylene, each containing 0, 1, 2, or 3 heteroatoms selected from O, S, or N;

or —O—, —S—, —N($R_3$)—, —N($R_3$)S($O_p$)—, —N($R_3$)C(O)—, —N($R_3$)C(O)S($O_p$)—, —OS($O_p$)—, —C(O)S($O_p$)—, or —C(O)N($R_3$)S($O_p$)—;

each p is independently 0, 1, or 2;

$R_5$ is H; optionally substituted alkyl, optionally substituted alkenyl, or optionally substituted alkynyl, each containing 0, 1, 2, or 3 heteroatoms selected from O, S, or N; optionally substituted carbocyclic, optionally substituted heterocyclic, optionally substituted aryl, or optionally substituted heteroaryl;

===== denotes a carbon-carbon single or double bond (i.e.,

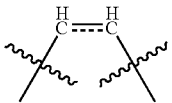

means

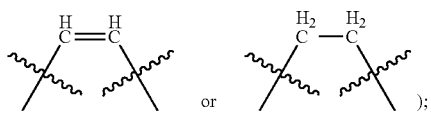

each of $R_a$, $R_b$, $R_c$, and $R_d$ are each independently H or halo, wherein at least two of $R_a$, $R_b$, $R_c$, and $R_d$ are halo; and $R_b$ and $R_d$ are absent if ==== is a double bond each $R_3$ and $R_4$ is independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; and optionally substituted carbocyclic;

L is absent or a $C_2$-$C_5$ saturated or unsaturated chain, optionally containing one to three heteroatoms independently selected from O, N and $S(O)_q$, wherein L is optionally substituted with one or more substituents selected from halogen, hydroxy, mercapto, amino, carboxy, nitro, oxo, phosphonoxy, phosphono, thioxo, cyano, $C_1$-$C_6$alkyl, $C_2$-$C_6$alkenyl and $C_2$-$C_6$alkynyl, wherein each $C_1$-$C_6$alkyl, $C_2$-$C_6$alkenyl and $C_2$-$C_6$alkynyl, group is optionally substituted at each occurrence with one or more substituents selected from halogen, hydroxy, mercapto, amino, carboxy, nitro, oxo, phosphonoxy, phosphono, thioxo, formyl and cyano;

j=independently 0, 1, 2, 3, or 4;
k=independently 0, 1, 2, or 3;
each m is independently 0, 1, or 2; and
q is independently 0, 1, or 2.

The present invention also features the compounds of Formula I', and pharmaceutically acceptable salts, esters, hydrates, solvates, polymorphs, or prodrugs thereof,

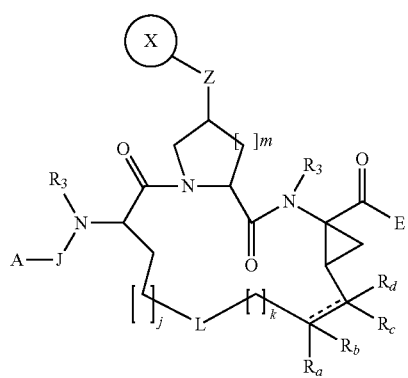

(I')

wherein Z, X, A, L, $R_3$, J, E, j, k, m, $R_a$, $R_b$, $R_c$, and $R_d$, are as defined in Formula I.

In another aspect, the invention provides a pharmaceutical composition comprising a compound of any of the formulae herein (e.g., Formula I or I'), or a pharmaceutically acceptable salt, ester, or prodrug thereof, in combination with an excipient.

In one aspect, the invention provides a method of treating a viral infection in a subject, comprising administering to the subject a therapeutically effective amount of a compound of any of the formulae herein (e.g., Formula I or I', or a pharmaceutically acceptable salt, ester or prodrug thereof, or a pharmaceutical composition comprising the same.

DETAILED DESCRIPTION OF THE INVENTION

In one aspect, the invention provides a compound of formula I:

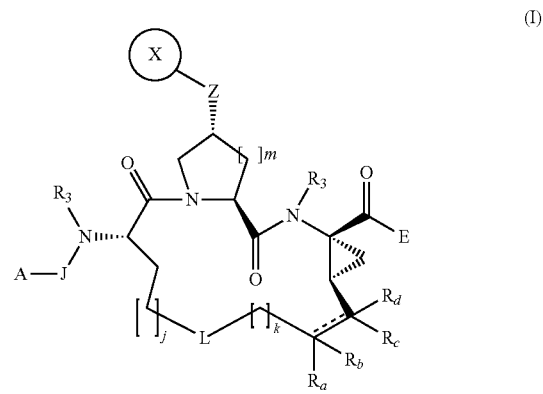

(I)

or pharmaceutically acceptable salts, esters, hydrates, solvates, polymorphs, or prodrugs thereof,
wherein:

X is an optionally substituted carbocyclic, optionally substituted heterocyclyl, optionally substituted aryl, or optionally substituted heteroaryl;

Z is O, $S(O)_m$, $NR_x$, OC(O), C(O), C(O)O, $NR_xC(O)$, or $C(O)NR_x$;

each $R_x$ is independently H or alkyl;

J is —C(O)—, —O—C(O)—, —C(O)O—, —N($R_3$)—C(O)—, —C(S)—, —C(=$NR_4$)—, —N($R_3$)—, —S(O)—, or —S($O_2$)— or absent;

A is selected from the group consisting of the following:
(i) H, aryl; substituted aryl; heteroaryl; substituted heteroaryl;
(ii) heterocyclyl or substituted heterocyclyl; and
(iii) —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; substituted —$C_1$-$C_8$ alkyl, substituted —$C_2$-$C_8$ alkenyl or substituted —$C_2$-$C_8$ alkynyl, each containing 0, 1, 2, or 3 heteroatoms independently selected from O, S and N; —$C_3$-$C_{12}$ carbocyclic, substituted —$C_3$-$C_{12}$ carbocyclic; —$C_3$-$C_{12}$ cycloalkenyl, or substituted —$C_3$-$C_{12}$ cycloalkenyl;

E is -G-$R_5$;
wherein G is absent; optionally substituted alkylene, optionally substituted alkenylene, optionally substituted alkynylene, each containing 0, 1, 2, or 3 heteroatoms selected from O, S, or N;
or —O—, —S—, —N($R_3$)—, —N($R_3$)S($O_p$)—, —N($R_3$)C(O)—, —N($R_3$)C(O)S($O_p$)—, —OS($O_p$)—, —C(O)S($O_p$)—, or —C(O)N($R_3$)S($O_p$)—;
each p is independently 0, 1, or 2;
$R_5$ is H; optionally substituted alkyl, optionally substituted alkenyl, or optionally substituted alkynyl, each containing 0, 1, 2, or 3 heteroatoms selected from O, S, or N; optionally substituted carbocyclic, optionally substituted heterocyclic, optionally substituted aryl, or optionally substituted heteroaryl;

==== denotes a carbon-carbon single or double bond (i.e., means

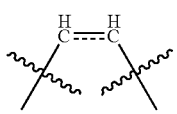

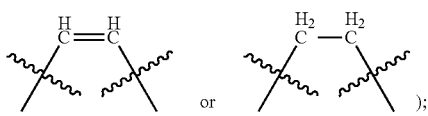

each of $R_a$, $R_b$, $R_c$, and $R_d$ are each independently H or halo, wherein at least two of $R_a$, $R_b$, $R_c$, and $R_d$ are halo; and $R_b$ and $R_d$ are absent if ═══ is a double bond each $R_3$ and $R_4$ is independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; and optionally substituted carbocyclic;

L is absent or a $C_2$-$C_5$ saturated or unsaturated chain, optionally containing one to three heteroatoms independently selected from O, N and $S(O)_q$, wherein L is optionally substituted with one or more substituents selected from halogen, hydroxy, mercapto, amino, carboxy, nitro, oxo, phosphonoxy, phosphono, thioxo, cyano, $C_1$-$C_6$alkyl, $C_2$-$C_6$alkenyl and $C_2$-$C_6$alkynyl, wherein each $C_1$-$C_6$alkyl, $C_2$-$C_6$alkenyl and $C_2$-$C_6$alkynyl, group is optionally substituted at each occurrence with one or more substituents selected from halogen, hydroxy, mercapto, amino, carboxy, nitro, oxo, phosphonoxy, phosphono, thioxo, formyl and cyano;

j=independently 0, 1, 2, 3, or 4;
k=independently 0, 1, 2, or 3;
each m is independently 0, 1, or 2; and
q is independently 0, 1, or 2.

The present invention also features the compounds of Formula I', and pharmaceutically acceptable salts, esters, hydrates, solvates, polymorphs, or prodrugs thereof, (I')

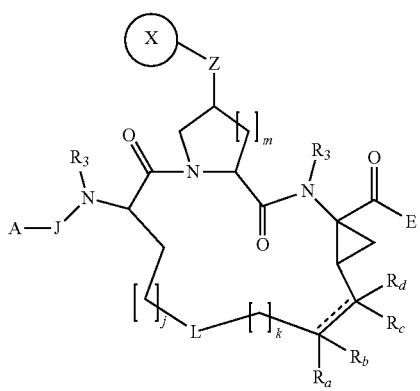

wherein Z, X, A, L, $R_3$, J, E, j, k, m, $R_a$, $R_b$, $R_c$, and $R_d$ are as defined in Formula I.

In certain embodiments, Z is O or OC(O); and ring X is cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl;-1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl; each of which may be optionally substituted.

In a further embodiment, ring X is phenanthridinyl, quinoxalinyl, quinolinyl, or isoindolinyl.

In a further embodiment, ring X is

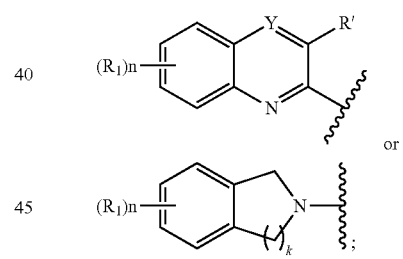

wherein
Y is N or —C(R")—;
wherein if Y is —C(R")—, then R' and R" taken together with the carbon atoms to which they are attached form a ring, which is optionally substituted;
R' is H, alkyl, alkenyl, alkynyl, carbocyclic, heterocyclyl, aryl, or heteroaryl, each of which may be optionally substituted;
each $R_1$ is independently selected from halogen, hydroxy, amino, —CN, —CF$_3$, —N$_3$, —NO$_2$, —OR$_4$, —SR$_4$, —SOR$_4$, —SO$_2$R$_4$, —N(R$_3$)S(O)$_2$—R$_4$, —N(R$_3$)(SO$_2$)NR$_3$R$_4$, —NR$_3$R$_4$, —C(O)—OR$_4$, —C(O)R$_4$, —C(O)NR$_3$R$_4$, —N(R$_3$)C(O)R$_4$; optionally substituted aryl; optionally substituted heteroaryl; optionally substituted heterocyclic; optionally substituted carbocyclic; optionally substituted alkyl, optionally substituted haloalkyl, optionally substituted alkenyl, or optionally substituted alkynyl, each containing 0, 1, 2, or 3 heteroatoms selected from O, S, or N;
each n is independently 0, 1, 2, 3, or 4;

each $R_3$ and $R_4$ are independently selected at each occurrence from the following:
optionally substituted alkyl, optionally substituted haloalkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; and
k is 0, 1, or 2.

In another aspect, the invention provides a compound of formula I-A:

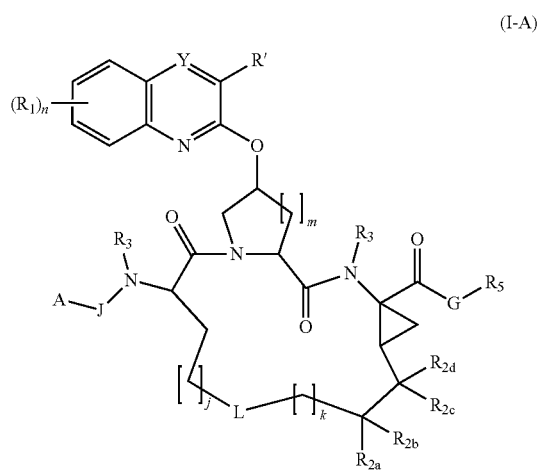

(I-A)

or a pharmaceutically acceptable salt, ester or prodrug thereof,
wherein:
J is —C(O)—, —O—C(O)—, —N($R_3$)—C(O)—, —C(S)—, —C(=N$R_4$)—, —N($R_3$)—, —S(O)—, or —S($O_2$)— or absent;
A is optionally substituted alkyl, optionally substituted heteroaryl, optionally substituted aryl, optionally substituted heterocyclic, or optionally substituted carbocyclic;
Y is N or —C(R")—;
R' is H, optionally substituted alkyl, optionally substituted aryl, optionally substituted heteroaryl; optionally substituted carbocyclic, or optionally substituted heterocyclic; or
R' and R", together with the atoms to which each is attached, can form a ring;
each $R_1$ is independently selected from H, halogen, hydroxy, amino, —CN, —$CF_3$, —$N_3$, —$NO_2$, —$OR_4$, —$SR_4$, —$SOR_4$, —$SO_2R_4$, —N($R_3$)S$(O)_2$—$R_4$, —N($R_3$)($SO_2$)NR$_3$R$_4$, —NR$_3$R$_4$, —C(O)—$OR_4$, —C(O)$R_4$, —C(O)NR$_3$R$_4$, —N($R_3$)C(O)$R_4$; optionally substituted aryl; optionally substituted heteroaryl; optionally substituted heterocyclic; optionally substituted carbocyclic; optionally substituted alkyl, optionally substituted haloalkyl, optionally substituted alkenyl, or optionally substituted alkynyl, each containing 0, 1, 2, or 3 heteroatoms selected from O, S, or N;
G is —N($R_3$)S$(O)_p$—; —N($R_3$)C(O)—, —N($R_3$)C(O)S($O_p$)—, —OS$(O)_p$—, —C(O)S$(O)_p$—, or —C(O)N($R_3$)S$(O)_p$—;
each p is independently 0, 1, or 2;
$R_5$ is H, optionally substituted alkyl, optionally substituted carbocyclic, optionally substituted heterocyclic, optionally substituted aryl, or optionally substituted heteroaryl;
each of $R_{2a}$, $R_{2b}$, $R_{2c}$, and $R_{2d}$ are each independently H or F, wherein at least two of $R_{2a}$, $R_{2b}$, $R_{2c}$, and $R_{2d}$ are F;

each $R_3$ and $R_4$ are independently selected at each occurrence from the following: optionally substituted alkyl, optionally substituted haloalkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;
L is absent or is selected from optionally substituted alkylene, optionally substituted alkenylene or optionally substituted alkynylene, each containing 0, 1, 2, or 3 heteroatoms selected from O, S, or N;
j=independently 0, 1, 2, 3, or 4;
k=independently 0, 1, 2, or 3;
m=independently 0, 1, or 2; and
n is independently 0, 1, 2, 3, or 4, In certain embodiments of this aspect, Y is —C(R")—; and R' and R", taken together with the atoms to which each is attached, form a ring.

In a further embodiment, the ring formed by R' and R" is an optionally substituted aryl, an optionally substituted heteroaryl, an optionally substituted carbocyclic or an optionally substituted heterocyclic.

In other embodiments, Y is N and R' is H, optionally substituted alkyl, optionally substituted aryl, or optionally substituted heteroaryl.

In certain embodiments, G is —N($R_3$)S$(O)_p$—; —N($R_3$)C(O)—, —OS$(O)_p$—, or —C(O)S$(O)_p$—; and p is 2.

In a further embodiment, $R_5$ is optionally substituted carbocyclic, optionally substituted heterocyclic, optionally substituted aryl, or optionally substituted heteroaryl. In certain embodiments, $R_5$ is carbocyclic.

In various embodiments, $R_{2a}$ and $R_{2b}$ are F. In other embodiments, $R_{2c}$ and $R_{2d}$ are F. In still other embodiments, $R_{2a}$ and $R_{2c}$ are F.

In another embodiments, J is —C(O)—, —O—C(O)—, —S(O)—, or —S($O_2$)—.

In other embodiments, A is an optionally substituted alkyl, optionally substituted heteroaryl, or optionally substituted aryl. In certain embodiments, A is heteroaryl or alkyl.

In yet another aspect, the invention provides a compound of formula I-A, or a pharmaceutically acceptable salt, ester or prodrug thereof,
wherein: Y is —C(R")—,
R' and R", taken together with the atoms to which each is attached, form a phenyl which is optionally substituted with one or more $R_1$;
m is 1, j is 2, k is 2, L is absent;
J is —C(O)—, —O—C(O)—, —N($R_3$)—C(O)—, —S(O)—, or —S($O_2$)—;
A is optionally substituted alkyl, optionally substituted alkenyl, optionally substituted alkynyl, optionally substituted heteroaryl, optionally substituted aryl, optionally substituted heterocyclic, or optionally substituted carbocyclic;
each $R_1$ is independently selected from H, halogen, hydroxy, amino, —CN, —$CF_3$, —$N_3$, —$NO_2$, —$OR_4$, —$SR_4$, —NR$_3$R$_4$, optionally substituted aryl; optionally substituted heteroaryl; optionally substituted heterocyclic; optionally substituted carbocyclic; optionally substituted haloalkyl, or optionally substituted alkyl, optionally substituted alkenyl, optionally substituted alkynyl;
G is —N($R_3$)S$(O)_p$—;
p is 0, 1, or 2;
each of $R_{2a}$, $R_{2b}$, $R_{2c}$, and $R_{2d}$ are each independently H or F, wherein at least two of $R_{2a}$, $R_{2b}$, $R_{2c}$, and $R_{2d}$ are F;
$R_5$ is optionally substituted carbocyclic or heterocyclic;

each $R_3$ and $R_4$ is independently selected at each occurrence from the following: optionally substituted alkyl, optionally substituted haloalkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; and n is 0, 1, 2, 3, or 4.

In one embodiment of this aspect, J is —C(O)—, or —O—C(O)—.

In another embodiment of this aspect, A is methyl, ethyl, propyl, iso-propyl, butyl, i-butyl, t-butyl, pentyl, hexyl, heptyl, phenyl, pyridyl, pyrimidyl, pyrazinyl, triazinyl, furanyl, thiophenyl, pyrrolyl, isoxazolyl, or pyrazolyl; each of which may be optionally substituted.

In certain embodiments of this aspect, G is —N($R_3$)S(O)$_p$— and $R_5$ is cyclopropyl, cyclobutyl, cyclopentyl, cyclohexyl, or cycloheptyl, each of which is optionally substituted.

In one embodiment of aspect, $R_{2a}$ and $R_{2b}$ are F. In another embodiment, $R_{2a}$ and $R_{2c}$ are F. In another embodiment, $R_{2c}$ and $R_{2d}$ are F.

In still another embodiment of this aspect, A-J- is A-C(O)— or A-O—C(O)—; A is $C_1$-$C_8$alkyl, $C_2$-$C_8$alkenyl or $C_2$-$C_8$alkynyl, each of which is optionally substituted with one or more $R_H$, or A is 5- to 6-membered carbocyclic or heterocyclic which is optionally substituted with one or more $R_G$; -G-$R_5$ is —N($R_3$)S(O)$_2$—$R_5$; and $R_5$ is 3- to 6-membered carbocyclic or heterocyclic which is optionally substituted with one or more $R_G$. Each $R_H$ is independently selected at each occurrence from independently selected at each occurrence from halogen, hydroxy, mercapto, amino, nitro, oxo, thioxo, or cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, nitro, oxo, thioxo, cyano or 3- to 6-membered carbocycle or heterocycle; or 3- to 6-membered carbocycle or heterocycle; wherein each 3- to 6-membered carbocycle or heterocycle in $R_H$ is independently optionally substituted at each occurrence with one or more substituents selected from halogen, hydroxy, mercapto, amino, nitro, oxo, thioxo, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. Each $R_1$ is independently selected at each occurrence from hydrogen or $R_G$. Each $R_G$ is independently selected at each occurrence from halo, hydroxy, mercapto, amino, nitro, oxo, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, nitro, oxo, thioxo, cyano; or $C_3$-$C_6$carbocycle or 3- to 6-membered heterocycle, each of which is independently optionally substituted at each occurrence with one or more substituents selected from halogen, hydroxy, mercapto, amino, nitro, oxo, thioxo, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. Each $R_3$ is independently selected at each occurrence from hydrogen; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, nitro, oxo, thioxo, cyano or 3- to 6-membered carbocycle or heterocycle; or 3- to 6-membered carbocycle or heterocycle; wherein each 3- to 6-membered carbocycle or heterocycle in $R_3$ is independently optionally substituted at each occurrence with one or more substituents selected from halogen, hydroxy, mercapto, amino, nitro, oxo, thioxo, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. Preferably, $R_3$ is hydrogen.

In still another embodiment of this aspect, A-J- is A-C(O)— or A-O—C(O)—; A is 5- to 6-membered aryl or heteroaryl which is optionally substituted with one or more $R_G$; -G-$R_5$ is —N($R_3$)S(O)$_2$—$R_5$ (preferably —N(H)S(O)$_2$—$R_5$); and $R_5$ is 3- to 6-membered cycloalkyl (preferably cyclopropyl) which is optionally substituted with one or more $R_G$. Each $R_1$ is independently selected at each occurrence from hydrogen or $R_G$. $R_G$ is as defined above. Each $R_3$ is independently selected at each occurrence from hydrogen; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, nitro, oxo, thioxo, cyano or 3- to 6-membered carbocycle or heterocycle; or 3- to 6-membered carbocycle or heterocycle; wherein each 3- to 6-membered carbocycle or heterocycle in $R_3$ is independently optionally substituted at each occurrence with one or more substituents selected from halogen, hydroxy, mercapto, amino, nitro, oxo, thioxo, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. Preferably, $R_3$ is hydrogen.

In still another aspect, the invention provides a compound of formula I-A, or a pharmaceutically acceptable salt, ester or prodrug thereof, wherein:

Y is —C(R")—;

R' and R", taken together with the atoms to which each is attached, form a phenyl which is optionally substituted with one or more $R_1$;

m is 1, j is 2, k is 2, L is absent;

J is —C(O)— or —O—C(O)—;

A is optionally substituted alkyl, optionally substituted alkenyl, optionally substituted alkynyl, optionally substituted heteroaryl, optionally substituted aryl, optionally substituted heterocyclic, or optionally substituted carbocyclic;

each $R_1$ is independently selected from H, halogen, hydroxy, amino, —CN, —CF$_3$, —N$_3$, —NO$_2$, —O$R_4$, —S$R_4$, —N$R_3$$R_4$, optionally substituted aryl; optionally substituted heteroaryl; optionally substituted heterocyclic; optionally substituted carbocyclic; optionally substituted haloalkyl, or optionally substituted alkyl, optionally substituted alkenyl, optionally substituted alkynyl;

G is —N($R_3$)S(O)$_p$—;

p is 0, 1, or 2;

$R_5$ is optionally substituted carbocyclic or heterocyclic;

$R_{2a}$ and $R_{2b}$ are F, and $R_{2c}$ and $R_{2d}$ are H;

each $R_3$ and $R_4$ is independently selected at each occurrence from the following: optionally substituted alkyl, optionally substituted haloalkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; and n is 0, 1, 2, 3, or 4.

In certain embodiments, A is methyl, ethyl, propyl, iso-propyl, butyl, i-butyl, t-butyl, pentyl, hexyl, heptyl,

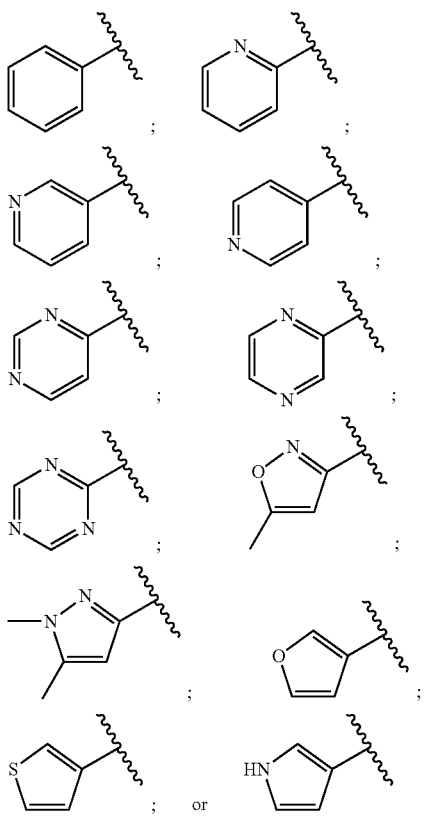

In another embodiment, $R_5$ is optionally substituted cyclopropyl.

In various embodiments, n is 0.

In still another embodiment of this aspect, A-J- is A-C(O)— or A-O—C(O)—; A is $C_1$-$C_8$alkyl, $C_2$-$C_8$alkenyl or $C_2$-$C_8$alkynyl, each of which is optionally substituted with one or more $R_H$, or A is 5- to 6-membered carbocyclic or heterocyclic which is optionally substituted with one or more $R_G$; -G-$R_5$ is —N($R_3$)S(O)$_2$—$R_5$; and $R_5$ is 3- to 6-membered carbocyclic or heterocyclic which is optionally substituted with one or more $R_G$. Each $R_H$ is independently selected at each occurrence from independently selected at each occurrence from halogen, hydroxy, mercapto, amino, nitro, oxo, thioxo, or cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, nitro, oxo, thioxo, cyano or 3- to 6-membered carbocycle or heterocycle; or 3- to 6-membered carbocycle or heterocycle; wherein each 3- to 6-membered carbocycle or heterocycle in $R_H$ is independently optionally substituted at each occurrence with one or more substituents selected from halogen, hydroxy, mercapto, amino, nitro, oxo, thioxo, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. Each $R_1$ is independently selected at each occurrence from hydrogen or $R_G$. Each $R_G$ is independently selected at each occurrence from halo, hydroxy, mercapto, amino, nitro, oxo, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, nitro, oxo, thioxo, cyano; or $C_3$-$C_6$carbocycle or 3- to 6-membered heterocycle, each of which is independently optionally substituted at each occurrence with one or more substituents selected from halogen, hydroxy, mercapto, amino, nitro, oxo, thioxo, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. Each $R_3$ is independently selected at each occurrence from hydrogen; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, nitro, oxo, thioxo, cyano or 3- to 6-membered carbocycle or heterocycle; or 3- to 6-membered carbocycle or heterocycle; wherein each 3- to 6-membered carbocycle or heterocycle in $R_3$ is independently optionally substituted at each occurrence with one or more substituents selected from halogen, hydroxy, mercapto, amino, nitro, oxo, thioxo, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. Preferably, $R_3$ is hydrogen.

In still another embodiment of this aspect, A-J- is A-C(O)— or A-O—C(O)—; A is 5- to 6-membered aryl or heteroaryl which is optionally substituted with one or more $R_G$; -G-$R_5$ is —N($R_3$)S(O)$_2$—$R_5$ (preferably —N(H)S(O)$_2$—$R_5$); and $R_5$ is 3- to 6-membered cycloalkyl (preferably cyclopropyl) which is optionally substituted with one or more $R_G$. Each $R_1$ is independently selected at each occurrence from hydrogen or $R_G$. $R_G$ is as defined above. Each $R_3$ is independently selected at each occurrence from hydrogen; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, nitro, oxo, thioxo, cyano or 3- to 6-membered carbocycle or heterocycle; or 3- to 6-membered carbocycle or heterocycle; wherein each 3- to 6-membered carbocycle or heterocycle in $R_3$ is independently optionally substituted at each occurrence with one or more substituents selected from halogen, hydroxy, mercapto, amino, nitro, oxo, thioxo, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. Preferably, $R_3$ is hydrogen.

In a further aspect, the invention provides a compound of formula II:

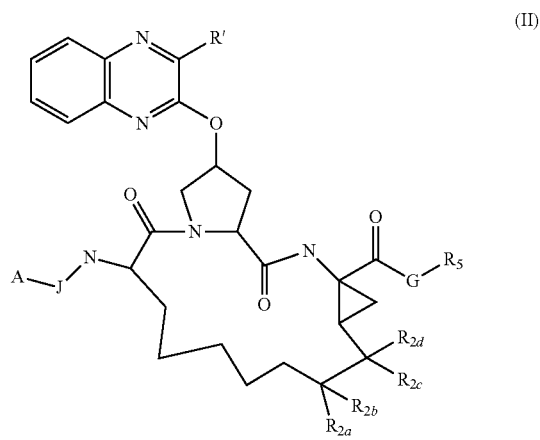

(II)

or a pharmaceutically acceptable salt, ester or prodrug thereof,
wherein:
J is —C(O)—, —O—C(O)—, —N($R_3$)—C(O)—, —S(O)—, or —S(O$_2$)—;

A is optionally substituted alkyl, or optionally substituted heteroaryl, optionally substituted aryl, optionally substituted heterocyclic, or optionally substituted carbocyclic;

R' is H, optionally substituted aryl; optionally substituted heteroaryl; or optionally substituted alkyl;

G is —N(R$_3$)S(O)$_p$—;

p is 0, 1, or 2;

each of R$_{2a}$, R$_{2b}$, R$_{2c}$, and R$_{2d}$ are each independently H or F, wherein at least two of R$_{2a}$, R$_{2b}$, R$_{2c}$, and R$_{2d}$ are F;

R$_5$ is optionally substituted carbocyclic, optionally substituted heterocyclic, optionally substituted aryl, or optionally substituted heteroaryl; and each R$_3$ and R$_4$ is independently selected at each occurrence from the following: optionally substituted alkyl, optionally substituted haloalkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen.

In certain embodiments, R' is H, optionally substituted alkyl; optionally substituted aryl; or optionally substituted heteroaryl.

In another embodiment, J is —C(O)—, or —O—C(O)—.

In other embodiments, A is methyl, ethyl, propyl, isopropyl, butyl, i-butyl, t-butyl, pentyl, hexyl, heptyl, phenyl, pyridyl, pyrimidyl, pyrazinyl, triazinyl, furanyl, thiophenyl, pyrrolyl, isoxazolyl, or pyrazolyl; each of which may be optionally substituted.

In various embodiments, G is —N(R$_3$)S(O)$_p$— and R$_5$ is cyclopropyl, cyclobutyl, cyclopentyl, cyclohexyl, or cycloheptyl, each of which is optionally substituted.

In another embodiment, R$_{2a}$ and R$_{2b}$ are F. In another embodiment, R$_{2a}$ and R$_{2c}$ are F. In another embodiment, R$_{2c}$ and R$_{2d}$ are F.

In still another embodiment of this aspect, A-J- is A-C(O)— or A-O—C(O)—; A is C$_1$-C$_8$alkyl, C$_2$-C$_8$alkenyl or C$_2$-C$_8$alkynyl, each of which is optionally substituted with one or more R$_H$, or A is 5- to 6-membered carbocyclic or heterocyclic which is optionally substituted with one or more R$_G$; -G-R$_5$ is —N(R$_3$)S(O)$_2$—R$_5$; and R$_5$ is 3- to 6-membered carbocyclic or heterocyclic which is optionally substituted with one or more R$_G$. Each R$_H$ is independently selected at each occurrence from independently selected at each occurrence from halogen, hydroxy, mercapto, amino, nitro, oxo, thioxo, or cyano; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, nitro, oxo, thioxo, cyano or 3- to 6-membered carbocycle or heterocycle; or 3- to 6-membered carbocycle or heterocycle; wherein each 3- to 6-membered carbocycle or heterocycle in R$_H$ is independently optionally substituted at each occurrence with one or more substituents selected from halogen, hydroxy, mercapto, amino, nitro, oxo, thioxo, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl. Each R$_1$ is independently selected at each occurrence from hydrogen or R$_G$. Each R$_G$ is independently selected at each occurrence from halo, hydroxy, mercapto, amino, nitro, oxo, thioxo, cyano; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, nitro, oxo, thioxo, cyano; or C$_3$-C$_6$carbocycle or 3- to 6-membered heterocycle, each of which is independently optionally substituted at each occurrence with one or more substituents selected from halogen, hydroxy, mercapto, amino, nitro, oxo, thioxo, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl. Each R$_3$ is independently selected at each occurrence from hydrogen; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, nitro, oxo, thioxo, cyano or 3- to 6-membered carbocycle or heterocycle; or 3- to 6-membered carbocycle or heterocycle; wherein each 3- to 6-membered carbocycle or heterocycle in R$_3$ is independently optionally substituted at each occurrence with one or more substituents selected from halogen, hydroxy, mercapto, amino, nitro, oxo, thioxo, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl. Preferably, R$_3$ is hydrogen.

In still another embodiment of this aspect, A-J- is A-C(O)— or A-O—C(O)—; A is 5- to 6-membered aryl or heteroaryl which is optionally substituted with one or more R$_G$; -G-R$_5$ is —N(R$_3$)S(O)$_2$—R$_5$ (preferably —N(H)S(O)$_2$—R$_5$); and R$_5$ is 3- to 6-membered cycloalkyl (preferably cyclopropyl) which is optionally substituted with one or more R$_G$. Each R$_1$ is independently selected at each occurrence from hydrogen or R$_G$. R$_G$ is as defined above. Each R$_3$ is independently selected at each occurrence from hydrogen; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, nitro, oxo, thioxo, cyano or 3- to 6-membered carbocycle or heterocycle; or 3- to 6-membered carbocycle or heterocycle; wherein each 3- to 6-membered carbocycle or heterocycle in R$_3$ is independently optionally substituted at each occurrence with one or more substituents selected from halogen, hydroxy, mercapto, amino, nitro, oxo, thioxo, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl. Preferably, R$_3$ is hydrogen.

In another aspect, the invention provides a compound of formula II-a:

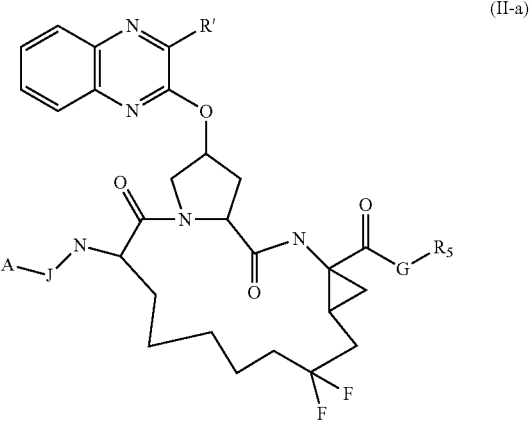

(II-a)

or a pharmaceutically acceptable salt, ester or prodrug thereof, wherein:

J is —C(O)— or —O—C(O)—;

A is optionally substituted alkyl, or optionally substituted heteroaryl, optionally substituted aryl, optionally substituted heterocyclic, or optionally substituted carbocyclic;

R' is H, optionally substituted alkyl; optionally substituted aryl; or optionally substituted heteroaryl;

G is —N(R$_3$)S(O)$_p$—;

p is 0, 1, or 2;

R$_5$ is optionally substituted carbocyclic; and each R$_3$ is optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen.

In one embodiment, R' is methyl, ethyl, propyl, iso-propyl, butyl, i-butyl, t-butyl, phenyl, pyridyl, pyrimidyl, pyrazinyl, triazinyl, furanyl, thiophenyl, pyrrolyl, isoxazolyl, or pyrazolyl; each of which may be optionally substituted.

In another embodiment, R' is methyl, ethyl, propyl, iso-propyl, butyl, i-butyl, t-butyl,

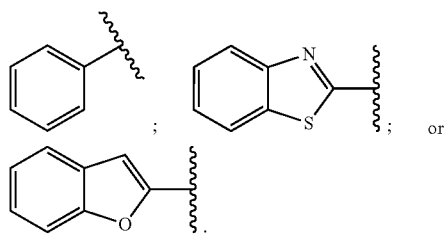

In another embodiment, A is methyl, ethyl, propyl, iso-propyl, butyl, i-butyl, t-butyl, pentyl, hexyl, heptyl, phenyl, pyridyl, pyrimidyl, pyrazinyl, triazinyl, furanyl, thiophenyl, pyrrolyl, isoxazolyl, or pyrazolyl; each of which may be optionally substituted.

In a further embodiment, A is methyl, ethyl, propyl, iso-propyl, butyl, i-butyl, t-butyl, pentyl, hexyl, heptyl,

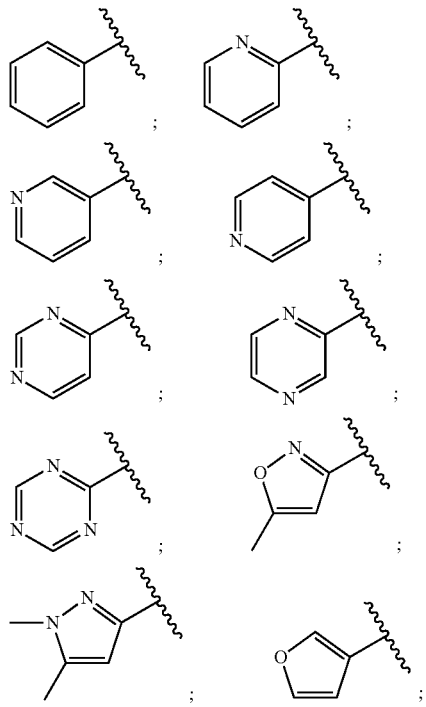

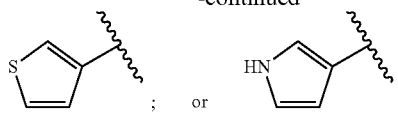

In other embodiments, G is —N(R$_3$)S(O)$_p$— and R$_5$ is cyclopropyl, cyclobutyl, cyclopentyl, cyclohexyl, or cycloheptyl, each of which is optionally substituted.

In a further embodiment, R$_5$ is optionally substituted cyclopropyl.

In still another embodiment of this aspect, A-J- is A-C(O)— or A-O—C(O)—; A is C$_1$-C$_8$alkyl, C$_2$-C$_8$alkenyl or C$_2$-C$_8$alkynyl, each of which is optionally substituted with one or more R$_H$, or A is 5- to 6-membered carbocyclic or heterocyclic which is optionally substituted with one or more R$_G$; -G-R$_5$ is —N(R$_3$)S(O)$_2$—R$_5$; and R$_5$ is 3- to 6-membered carbocyclic or heterocyclic which is optionally substituted with one or more R$_G$. Each R$_H$ is independently selected at each occurrence from independently selected at each occurrence from halogen, hydroxy, mercapto, amino, nitro, oxo, thioxo, or cyano; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, nitro, oxo, thioxo, cyano or 3- to 6-membered carbocycle or heterocycle; or 3- to 6-membered carbocycle or heterocycle; wherein each 3- to 6-membered carbocycle or heterocycle in R$_H$ is independently optionally substituted at each occurrence with one or more substituents selected from halogen, hydroxy, mercapto, amino, nitro, oxo, thioxo, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl. Each R$_1$ is independently selected at each occurrence from hydrogen or R$_G$. Each R$_G$ is independently selected at each occurrence from halo, hydroxy, mercapto, amino, nitro, oxo, thioxo, cyano; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, nitro, oxo, thioxo, cyano; or C$_3$-C$_6$carbocycle or 3- to 6-membered heterocycle, each of which is independently optionally substituted at each occurrence with one or more substituents selected from halogen, hydroxy, mercapto, amino, nitro, oxo, thioxo, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl. Each R$_3$ is independently selected at each occurrence from hydrogen; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, nitro, oxo, thioxo, cyano or 3- to 6-membered carbocycle or heterocycle; or 3- to 6-membered carbocycle or heterocycle; wherein each 3- to 6-membered carbocycle or heterocycle in R$_3$ is independently optionally substituted at each occurrence with one or more substituents selected from halogen, hydroxy, mercapto, amino, nitro, oxo, thioxo, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl. Preferably, R$_3$ is hydrogen.

In still another embodiment of this aspect, A-J- is A-C(O)— or A-O—C(O)—; A is 5- to 6-membered aryl or heteroaryl which is optionally substituted with one or more R$_G$; -G-R$_5$ is —N(R$_3$)S(O)$_2$—R$_5$ (preferably —N(H)S(O)$_2$—R$_5$); and R$_5$ is 3- to 6-membered cycloalkyl (preferably cyclopropyl) which is optionally substituted with one or more R$_G$. Each R$_1$ is independently selected at each occurrence from hydrogen or $R_G$. $R_G$ is as defined above. Each $R_3$ is independently selected at each occurrence from hydrogen; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, nitro, oxo, thioxo, cyano or 3- to 6-membered carbocycle or heterocycle; or 3- to 6-membered carbocycle or heterocycle; wherein each 3- to 6-membered carbocycle or heterocycle in $R_3$ is independently optionally substituted at each occurrence with one or more substituents selected from halogen, hydroxy, mercapto, amino, nitro, oxo, thioxo, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. Preferably, $R_3$ is hydrogen.

In yet another aspect, the invention provides a compound of formula IV:

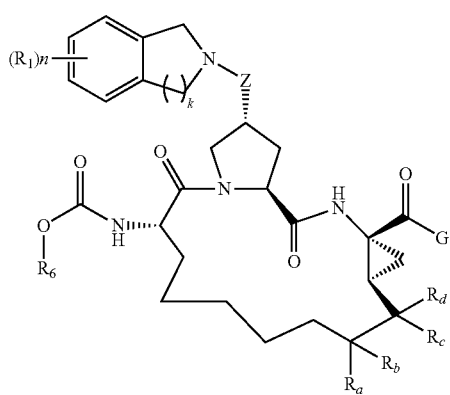

(IV)

wherein,

Z is OC(O), C(O), C(O)O, or C(O)$NR_x$;

$R_x$ is H or alkyl;

k is 0, 1, or 2;

each $R_1$ is independently selected from the group consisting of:
(i) H, aryl; substituted aryl; heteroaryl; substituted heteroaryl;
(ii) heterocyclyl or substituted heterocyclyl; and
(iii) —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; substituted —$C_1$-$C_8$ alkyl, substituted —$C_2$-$C_8$ alkenyl or substituted —$C_2$-$C_8$ alkynyl, each containing 0, 1, 2, or 3 heteroatoms independently selected from O, S and N; —$C_3$-$C_{12}$ carbocyclic, substituted —$C_3$-$C_{12}$ carbocyclic; —$C_3$-$C_{12}$ cycloalkenyl, or substituted —$C_3$-$C_{12}$ cycloalkenyl;

n is 0, 1, 2, 3, or 4;

$R_6$ is selected from aryl; substituted aryl; heteroaryl; substituted heteroaryl; heterocyclyl; substituted heterocyclyl; —$C_1$-$C_8$ alkyl, substituted —$C_1$-$C_8$ alkyl, —$C_3$-$C_{12}$ carbocyclic, and substituted —$C_3$-$C_{12}$ carbocyclic;

G is -E-$R_5$;

wherein E is —N($R_3$)S(O)$_p$—, —N($R_3$)C(O)—, or —N($R_3$)C(O)S(O)$_p$—;

each p is independently 0, 1, or 2;

$R_5$ is optionally substituted carbocyclic, optionally substituted heterocyclic, optionally substituted aryl, or optionally substituted heteroaryl;

each of $R_a$, $R_b$, $R_c$, and $R_d$ are each independently H or F, wherein at least two of $R_a$, $R_b$, $R_c$, and $R_d$ are F; and $R_3$ is H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic.

In another embodiment, the invention provides a compound wherein each $R^1$ is substituted with one, two, three or four independent $R^E$, wherein each $R^E$ is independently selected from alkyl, aryl, heteroaryl, cycloalkyl, heterocycloalkyl, halogen, hydroxy, amino, —CN, —$CF_3$, —$N_3$, —$NO_2$, —$OR^F$, —$SR^F$, —$SOR^F$, —$SO_2R^F$, —N($R^F$)S($O_2$)—$R^F$, —N($R^F$)S($O_2$)N$R^FR^F$, —N$R^FR^F$, —C(O)O$R^F$, —C(O)$R^F$, —C(O)N$R^FR^F$, or —N($R^F$)C(O)$R^F$; wherein each $R^F$ is independently hydrogen, $C_1$-$C_6$ alkyl, $C_2$-$C_6$ alkenyl, or $C_2$-$C_6$ alkynyl.

In certain embodiments, E is -G-$R_5$; and G is —O—, —S—, —N($R_3$)—, —N($R_3$)S(O)$_p$—, —N($R_3$)C(O)—, —N($R_3$) C(O)S(O$_p$)—, —OS(O$_p$)—, —C(O)S(O$_p$)—, or —C(O)N($R_3$)S(O)$_p$—; and each p is independently 0, 1, or 2. In a further embodiment, E is —N($R_3$)S(O)$_p$—.

In various embodiments, $R_5$ is H; optionally substituted carbocyclic, optionally substituted heterocyclic, optionally substituted aryl, or optionally substituted heteroaryl. In a further embodiment, $R_5$ is cyclopropyl optionally substituted with $C_1$-$C_6$alkyl, $C_1$-$C_6$alkoxy$C_1$-$C_6$alkyl, —C(O)OH, —C(O)$NH_2$, or —C(O)O—$C_1$-$C_6$alkyl.

In certain embodiments of formulae I and I', ═══ denotes a carbon-carbon single bond. In a further embodiment of each of the above-described aspects of the invention, at least two of $R_a$, $R_b$, $R_c$, and $R_d$ are F. In one embodiment, $R_a$ and $R_b$ are F. In one embodiment of each of the above-described aspects of the invention, $R_c$ and $R_d$ are F. In one embodiment of each of the above-described aspects of the invention, $R_a$ and $R_c$ are F. In another embodiment of each of the above-described aspects of the invention, three of $R_a$, $R_b$, $R_c$, and $R_d$ are F. In one embodiment of each of the above-described aspects of the invention, $R_a$, $R_b$, and $R_c$ are F. In one embodiment of each of the above-described aspects of the invention, $R_a$, $R_c$, and $R_d$ are F. In another embodiment of each of the above-described aspects of the invention, all of $R_a$, $R_b$, $R_c$, and $R_d$ are F.

In certain embodiments for formulae I and I', ----- denotes a carbon-carbon double bond. In certain embodiments of each of the above-described aspects of the invention, $R_a$ and $R_c$ are F.

In another embodiment of each of the above-described aspects of the invention, J is —(C═O)—; and A is optionally substituted heteroaryl.

In another embodiment of each of the above-described aspects of the invention, J is —(C═O)—; and A is optionally substituted aryl.

In another embodiment of each of the above-described aspects of the invention J is —(C═O)O—; and A is optionally substituted alkyl.

In another embodiment of each of the above-described aspects of the invention, J is —(C═O)—; A is optionally substituted alkyl; Z is O, ring X is phenanthridinyl, quinoxalinyl, quinolinyl, or isoindolinyl; and any two of $R_a$, $R_b$, $R_c$, and $R_d$ are each independently F.

In another embodiment of each of the above-described aspects of the invention, J is —(C═O)—; A is optionally substituted aryl; Z is O, ring X is phenanthridinyl, quinoxalinyl, quinolinyl, or isoindolinyl; and any two of $R_a$, $R_b$, $R_c$, and $R_d$ are each independently F.

In another embodiment of each of the above-described aspects of the invention, J is —(C═O)—; A is optionally substituted heteroaryl; Z is O, ring X is phenanthridinyl, quinoxalinyl, quinolinyl, or isoindolinyl; and any two of $R_a$, $R_b$, $R_c$, and $R_d$ are each independently F.

In another embodiment of each of the above-described aspects of the invention, J is —(C=O)O—; A is optionally substituted alkyl; Z is O, ring X is phenanthridinyl, quinoxalinyl, quinolinyl, or isoindolinyl; and any two of $R_a$, $R_b$, $R_c$, and $R_d$ are each independently F.

In another embodiment of each of the above-described aspects of the invention, J is —(C=O)O—; A is optionally substituted aryl; Z is O, ring X is phenanthridinyl, quinoxalinyl, quinolinyl, or isoindolinyl; and any two of $R_a$, $R_b$, $R_c$, and $R_d$ are each independently F.

In another embodiment of each of the above-described aspects of the invention, J is —(C=O)O—; A is optionally substituted heteroaryl; Z is O, ring X is phenanthridinyl, quinoxalinyl, quinolinyl, or isoindolinyl; and any two of $R_a$, $R_b$, $R_c$, and $R_d$ are each independently F.

In another embodiment of each of the above-described aspects of the invention, J is —(C=O)O— or —(C=O)—; A is optionally substituted alkyl; Z is O or (C=O), ring X is phenanthridinyl, quinoxalinyl, quinolinyl, or isoindolinyl; and $R_a$ and $R_b$ are F, and $R_c$ and $R_d$ are H.

In another embodiment of each of the above-described aspects of the invention, J is —(C=O)O— or —(C=O)—; A is optionally substituted alkyl; Z is O or (C=O), ring X is phenanthridinyl, quinoxalinyl, quinolinyl, or isoindolinyl; and $R_a$ and $R_c$ are F, and $R_b$ and $R_d$ are H.

In another embodiment of each of the above-described aspects of the invention, J is —(C=O)O— or —(C=O)—; A is optionally substituted alkyl; Z is O or (C=O), ring X is phenanthridinyl, quinoxalinyl, quinolinyl, or isoindolinyl; and $R_a$ and $R_b$ are H, and $R_c$ and $R_d$ are F.

In another embodiment of each of the above-described aspects of the invention, J is —(C=O)O— or —(C=O)—; A is optionally substituted aryl; Z is O or (C=O), ring X is phenanthridinyl, quinoxalinyl, quinolinyl, or isoindolinyl; and $R_a$ and $R_b$ are F, and $R_c$ and $R_d$ are H.

In another embodiment of each of the above-described aspects of the invention, J is —(C=O)O— or —(C=O)—; A is optionally substituted aryl; Z is O or (C=O), ring X is phenanthridinyl, quinoxalinyl, quinolinyl, or isoindolinyl; and $R_a$ and $R_c$ are F, and $R_b$ and $R_d$ are H.

In another embodiment of each of the above-described aspects of the invention, J is —(C=O)O— or —(C=O)—; A is optionally substituted aryl; Z is O or (C=O), ring X is phenanthridinyl, quinoxalinyl, quinolinyl, or isoindolinyl; and $R_a$ and $R_b$ are H, and $R_c$ and $R_d$ are F.

In another embodiment of each of the above-described aspects of the invention, J is —(C=O)O— or —(C=O)—; A is optionally substituted heteroaryl; Z is O or (C=O), ring X is phenanthridinyl, quinoxalinyl, quinolinyl, or isoindolinyl; and $R_a$ and $R_b$ are F, and $R_c$ and $R_d$ are H.

In another embodiment of each of the above-described aspects of the invention, J is —(C=O)O— or —(C=O)—; A is optionally substituted heteroaryl; Z is O or (C=O), ring X is phenanthridinyl, quinoxalinyl, quinolinyl, or isoindolinyl; and $R_a$ and $R_c$ are F, and $R_b$ and $R_d$ are H.

In another embodiment of each of the above-described aspects of the invention, J is —(C=O)O— or —(C=O)—; A is optionally substituted heteroaryl; Z is O or (C=O), ring X is phenanthridinyl, quinoxalinyl, quinolinyl, or isoindolinyl; and $R_a$ and $R_b$ are H, and $R_c$ and $R_d$ are F.

In another embodiment of each of the above-described aspects of the invention, E is —NHS(O)$_2$—R$_5$; R$_5$ is independently cyclopropyl optionally substituted with $C_1$-$C_6$alkyl; J is —(C=O)—; A is optionally substituted alkyl, Z is O; ring X is phenanthridinyl or quinoxalinyl; and any two of $R_a$, $R_b$, $R_c$, and $R_d$ are each independently F.

In another embodiment of each of the above-described aspects of the invention, E is —NHS(O)$_2$—R$_5$; R$_5$ is independently cyclopropyl optionally substituted with $C_1$-$C_6$alkyl; J is —(C=O)—; A is optionally substituted aryl, Z is O; ring X is phenanthridinyl or quinoxalinyl; and any two of $R_a$, $R_b$, $R_c$, and $R_d$ are each independently F.

In another embodiment of each of the above-described aspects of the invention, E is —NHS(O)$_2$—R$_5$; R$_5$ is independently cyclopropyl optionally substituted with $C_1$-$C_6$alkyl; J is —(C=O)—; A is optionally substituted heteroaryl, Z is O; ring X is phenanthridinyl or quinoxalinyl; and any two of $R_a$, $R_b$, $R_c$, and $R_d$ are each independently F.

In another embodiment of each of the above-described aspects of the invention, E is —NHS(O)$_2$—R$_5$; R$_5$ is independently cyclopropyl optionally substituted with $C_1$-$C_6$alkyl; J is —(C=O)O—; A is optionally substituted alkyl, Z is O; ring X is phenanthridinyl or quinoxalinyl; and any two of $R_a$, $R_b$, $R_c$, and $R_d$ are each independently F.

In another embodiment of each of the above-described aspects of the invention, E is —NHS(O)$_2$—R$_5$; R$_5$ is independently cyclopropyl optionally substituted with $C_1$-$C_6$alkyl; J is —(C=O)O—; A is optionally substituted aryl, Z is O; ring X is phenanthridinyl or quinoxalinyl; and any two of $R_a$, $R_b$, $R_c$, and $R_d$ are each independently F.

In another embodiment of each of the above-described aspects of the invention, E is —NHS(O)$_2$—R$_5$; R$_5$ is independently cyclopropyl optionally substituted with $C_1$-$C_6$alkyl; J is —(C=O)O—; A is optionally substituted heteroaryl, Z is O; ring X is phenanthridinyl or quinoxalinyl; and any two of $R_a$, $R_b$, $R_c$, and $R_d$ are each independently F.

In another embodiment of each of the above-described aspects of the invention, A is an optionally substituted nitrogen-containing heteroaryl.

In another embodiment of each of the above-described aspects of the invention, A is optionally substituted isoxazolyl, optionally substituted thiazolyl, optionally substituted pyrazolyl, optionally substituted pyrazinyl, optionally substituted pyridinyl, or optionally substituted pyrimidinyl.

In another embodiment of each of the above-described aspects of the invention, A is alkyl-substituted isoxazolyl.

In another embodiment of each of the above-described aspects of the invention, J can be, for example, —(C=O)— or —(C=O)O—; and A is selected from the following groups:

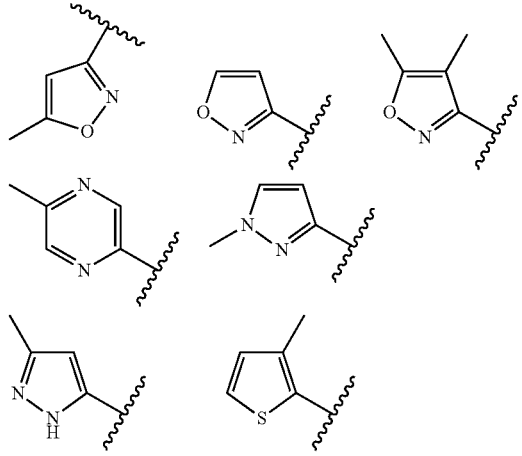

-continued

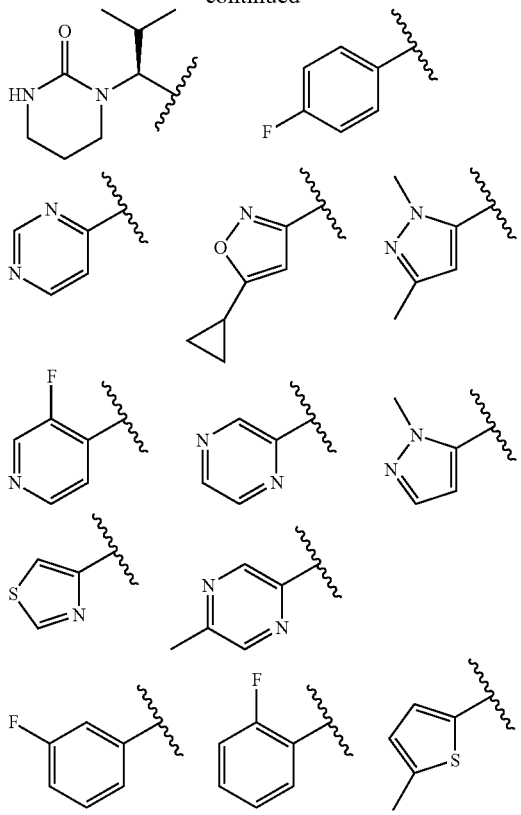

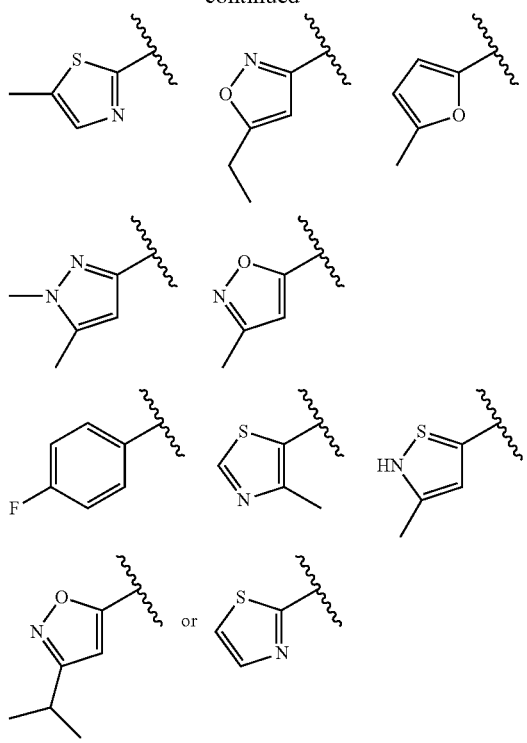

Representative compounds include, but are not limited to, the following compounds:

N-((2R,6S,13aS,14aR,16aS)-14a-(cyclopropyl sulfonylcarbamoyl)-12,12-difluoro-5,16-dioxo-2-(phenanthridin-6-yloxy)octadecahydrocyclopropa[e]pyrrolo[1,2-a][1,4]diazacyclopentadecin-6-yl)-5-methylisoxazole-3-carboxamide
(2R,6S,13aS,14aR,16aS)-N-(cyclopropylsulfonyl)-12,12-difluoro-6-(5-methylpyrazine-2-carboxamido)-5,16-dioxo-2-(phenanthridin-6-yloxy)octadecahydrocyclopropa[e]pyrrolo[1,2-a][1,4]diazacyclopentadecine-14a-carboxamide
tert-butyl (2R,6S,13aS,14aR,16aS)-14a-(cyclopropylsulfonylcarbamoyl)-12,12-difluoro-5,16-dioxo-2-(quinoxalin-2-yloxy)octadecahydrocyclopropa[e]pyrrolo[1,2-a][1,4]diazacyclopentadecin-6-ylcarbamate
tert-butyl (2R,6S,13aS,14aR,16aS)-14a-(cyclopropylsulfonylcarbamoyl)-12,12-difluoro-2-(3-methylquinoxalin-2-yloxy)-5,16-dioxooctadecahydrocyclopropa[e]pyrrolo[1,2-a][1,4]diazacyclopentadecin-6-ylcarbamate
N-((2R,6S,13aS,14aR,16aS)-14a-(cyclopropylsulfonylcarbamoyl)-12,12-difluoro-2-(3-methylquinoxalin-2-yloxy)-5,16-dioxooctadecahydrocyclopropa[e]pyrrolo[1,2-a][1,4]diazacyclopentadecin-6-yl)-5-methylisoxazole-3-carboxamide
(2R,6S,13aS,14aR,16aS)-6-(tert-butoxycarbonyl-amino)-14a-(cyclopropylsulfonylcarbamoyl)-12,12-difluoro-5,16-dioxooctadecahydrocyclopropa[e]pyrrolo[1,2-a][1,4]diazacyclopentadecin-2-yl 4-fluoroisoindoline-2-carboxylate
(2R,6S,13aS,14aR,16aS)-2-(3-(benzofuran-2-yl)quinoxalin-2-yloxy)-N-(cyclopropylsulfonyl)-12,12-difluoro-6-(1-methyl-1H-pyrazole-3-carboxamido)-5,16- tert-butyl (2R,6S,13aS,14aR,16aS)-14a-(cyclopropylsulfonylcarbamoyl)-12,12-difluoro-5,16-dioxo-2-(phenanthridin-6-yloxy)octadecahydrocyclopropa[e]pyrrolo[1,2-a][1,4]diazacyclopentadecin-6-ylcarbamate
(2R,6S,13aS,14aR,16aS)-N-(cyclopropylsulfonyl)-6-(1,5-dimethyl-1H-pyrazole-3-carboxamido)-12,12-difluoro-5,16-dioxo-2-(phenanthridin-6-yloxy)octadecahydrocyclopropa[e]pyrrolo[1,2-a][1,4]diazacyclopentadecine-14a-carboxamide
tert-butyl (2R,6S,13aS,14aR,16aS)-14a-(cyclopropylsulfonylcarbamoyl)-12,12-difluoro-5,16-dioxo-2-(3-phenylquinoxalin-2-yloxy)octadecahydrocyclopropa[e]pyrrolo[1,2-a][1,4]diazacyclopentadecin-6-ylcarbamate
N-((2R,6S,13aS,14aR,16aS)-14a-(cyclopropylsulfonylcarbamoyl)-12,12-difluoro-5,16-dioxo-2-(quinoxalin-2-yloxy)octadecahydrocyclopropa[e]pyrrolo[1,2-a][1,4]diazacyclopentadecin-6-yl)-5-methylisoxazole-3-carboxamide
N-((2R,6S,13aS,14aR,16aS)-14a-(cyclopropylsulfonylcarbamoyl)-12,12-difluoro-5,16-dioxo-2-(3-phenylquinoxalin-2-yloxy)octadecahydrocyclopropa[e]pyrrolo[1,2-a][1,4]diazacyclopentadecin-6-yl)-5-methylisoxazole-3-carboxamide
N-((2R,6S,13aS,14aR,16aS)-2-(3-(benzo[d]thiazol-2-yl)quinoxalin-2-yloxy)-14a-(cyclopropylsulfonyl-carbamoyl)-12,12-difluoro-5,16-dioxooctadecahydro-cyclopropa[e]pyrrolo[1,2-a][1,4]diazacyclo-pentadecin-6-yl)-5-methylisoxazole-3-carboxamide
N-((2R,6S,13aS,14aR,16aS)-2-(3-(benzofuran-2-yl)quinoxalin-2-yloxy)-14a-(cyclopropyl-sulfonylcarbamoyl)-12,12-difluoro-5,16-dioxoocta-decahydrocyclopropa[e]pyrrolo[1,2- dioxooctadecahydrocyclopropa[e]pyrrolo[1,2-a][1,4]diazacyclopentadecine-14a-carboxamide
tert-butyl (2R,6S,13aS,14aR,16aS)-14a-(cyclopropylsulfonylcarbamoyl)-2-(3-ethylquinoxalin-2-yloxy)-12,12-difluoro-5,16-dioxooctadecahydrocyclopropa[e]pyrrolo[1,2-a][1,4]diazacyclopentadecin-6-ylcarbamate
tert-butyl (2R,6S,13aS,14aR,16aS)-2-(3-ethylquinoxalin-2-yloxy)-12,12-difluoro-14a-(1-methylcyclopropylsulfonylcarbamoyl)-5,16-dioxooctadecahydrocyclopropa[e]pyrrolo[1,2-a][1,4]diazacyclopentadecin-6-ylcarbamate
N-((2R,6S,13aS,14aR,16aS)-14a-(cyclopropylsulfonylcarbamoyl)-2-(3-ethylquinoxalin-2-yloxy)-12,12-difluoro-5,16-dioxooctadecahydrocyclopropa[e]pyrrolo[1,2-a][1,4]diazacyclopentadecin-6-yl)isoxazole-3-carboxamide
tert-butyl (2R,6S,13aS,14aR,16aS)-2-(3-(benzo[d]thiazol-2-yl)quinoxalin-2-yloxy)-14a-(cyclopropylsulfonylcarbamoyl)-12,12-difluoro-5,16-dioxooctadecahydrocyclopropa[e]pyrrolo[1,2-a][1,4]diazacyclopentadecin-6-ylcarbamate
a][1,4]diazacyclopentadecin-6-yl)-5-methylisoxazole-3-carboxamide
N-((2R,6S,13aS,14aR,16aS)-14a-(cyclopropylsulfonylcarbamoyl)-2-(3-ethylquinoxalin-2-yloxy)-12,12-difluoro-5,16-dioxooctadecahydrocyclopropa[e]pyrrolo[1,2-a][1,4]diazacyclopentadecin-6-yl)-5-methylisoxazole-3-carboxamide
N-((2R,6S,13aS,14aR,16aS)-2-(3-ethylquinoxalin-2-yloxy)-12,12-difluoro-14a-(1-methylcyclopropylsulfonylcarbamoyl)-5,16-dioxooctadecahydrocyclopropa[e]pyrrolo[1,2-a][1,4]diazacyclopentadecin-6-yl)-5-methylisoxazole-3-carboxamide
(2R,6S,13aS,14aR,16aS)-N-(cyclopropylsulfonyl)-2-(3-ethylquinoxalin-2-yloxy)-12,12-difluoro-5,16-dioxo-6-pivalamido-octadecahydrocyclopropa[e]pyrrolo[1,2-a][1,4] diazacyclopentadecine-14a-carboxamide
tert-butyl (2R,6S,13aS,14aR,16aS)-2-(3-(benzofuran-2-yl)quinoxalin-2-yloxy)-14a-(cyclopropylsulfonylcarbamoyl)-12,12-difluoro-5,16-dioxooctadecahydrocyclopropa[e]pyrrolo[1,2-a][1,4]diazacyclopentadecin-6-ylcarbamate Other compounds contemplated by the invention include the following:

(2R,6S,13aS,14aR,16aS)-12,12-difluoro-2-(3-fluorophenanthridin-6-yloxy)-6-(1-methyl-1H-pyrazole-3-carboxamido)-N-(1-methylcyclopropylsulfonyl)-5,16-dioxooctadecahydrocyclopropa[e]pyrrolo[1,2-a][1,4]diazacyclopentadecine-14a-carboxamide
(2R,6S,13aS,14aR,16aS)-12,12-difluoro-2-(9-fluorophenanthridin-6-yloxy)-6-(1-methyl-1H-pyrazole-3-carboxamido)-N-(1-methylcyclopropylsulfonyl)-5,16-dioxooctadecahydrocyclopropa[e]pyrrolo[1,2-a][1,4]diazacyclopentadecine-14a-carboxamide
N-((2R,6S,13aS,14aR,16aS)-12,12-difluoro-2-(3-fluorophenanthridin-6-yloxy)-14a-(1-methylcyclopropylsulfonylcarbamoyl)-5,16-dioxooctadecahydrocyclopropa[e]pyrrolo[1,2-a][1,4]diazacyclopentadecin-6-yl)-5-methylisoxazole-3-carboxamide
N-((2R,6S,13aS,14aR,16aS)-12,12-difluoro-2-(9-fluorophenanthridin-6-yloxy)-14a-(1-methylcyclopropylsulfonylcarbamoyl)-5,16-dioxooctadecahydrocyclopropa[e]pyrrolo[1,2-a][1,4]diazacyclopentadecin-6-yl)-5-methylisoxazole-3-carboxamide
(2R,6S,13aS,14aR,16aS)-12,12-difluoro-6-(1-methyl-1H-pyrazole-3-carboxamido)-N-(1-methylcyclopropylsulfonyl)-5,16-dioxo-2-(3-(trifluoromethoxy)phenanthridin-6-yloxy)octadecahydrocyclopropa[e]pyrrolo[1,2-a][1,4]diazacyclopentadecine-14a-carboxamide
(2R,6S,13aS,14aR,16aS)-12,12-difluoro-6-(1-methyl-1H-pyrazole-3-carboxamido)-N-(1-methylcyclopropylsulfonyl)-5,1 6-dioxo-2-(3-(trifluoromethyl)phenanthridin-6-yloxy)octadecahydrocyclopropa[e]pyrrolo[1,2-a][1,4]diazacyclopentadecine-14a-carboxamide
N-((2R,6S,13aS,14aR,16aS)-12,12-difluoro-14a-(1-methylcyclopropylsulfonylcarbamoyl)-5,16-dioxo-2-(3-(trifluoromethoxy)phenanthridin-6-yloxy)octadecahydrocyclopropa[e]pyrrolo[1,2-a][1,4]diazacyclopentadecin-6-yl)-5-methylisoxazole-3-carboxamide
N-((2R,6S,13aS,14aR,16aS)-12,12-difluoro-
(2R,6S,13aS,14aR,16aS)-N-(cyclopropylsulfonyl)-12,12-difluoro-2-(3-fluorophenanthridin-6-yloxy)-6-(1-methyl-1H-pyrazole-3-carboxamido)-5,16-dioxooctadecahydrocyclopropa[e]pyrrolo[1,2-a][1,4]diazacyclopentadecine-14a-carboxamide
(2R,6S,13aS,14aR,16aS)-N-(cyclopropylsulfonyl)-12,12-difluoro-2-(9-fluorophenanthridin-6-yloxy)-6-(1-methyl-1H-pyrazole-3-carboxamido)-5,16-dioxooctadecahydrocyclopropa[e]pyrrolo[1,2-a][1,4] diazacyclopentadecine-14a-carboxamide
N-((2R,6S,13aS,14aR,16aS)-14a-(cyclopropylsulfonylcarbamoyl)-12,12-difluoro-2-(3-fluorophenanthridin-6-yloxy)-5,16-dioxooctadecahydrocyclopropa[e]pyrrolo[1,2-a][1,4]diazacyclopentadecin-6-yl)-5-methylisoxazole-3-carboxamide
N-((2R,6S,13aS,14aR,16aS)-14a-(cyclopropylsulfonylcarbamoyl)-12,12-difluoro-2-(9-fluorophenanthridin-6-yloxy)-5,16-dioxooctadecahydrocyclopropa[e]pyrrolo[1,2-a][1,4]diazacyclopentadecin-6-yl)-5-methylisoxazole-3-carboxamide
(2R,6S,13aS,14aR,16aS)-N-(cyclopropylsulfonyl)-12,12-difluoro-6-(1-methyl-1H-pyrazole-3-carboxamido)-5,16-dioxo-2-(3-(trifluoromethoxy)phenanthridin-6-yloxy)octadecahydro-cyclopropa[e]pyrrolo[1,2-a][1,4]diaza-cyclopentadecine-14a-carboxamide
(2R,6S,13aS,14aR,16aS)-N-(cyclopropylsulfonyl)-12,12-difluoro-6-(1-methyl-1H-pyrazole-3-carboxamido)-5,16-dioxo-2-(3-(trifluoromethyl)phenanthridin-6-yloxy)octadecahydrocyclopropa[e]pyrrolo[1,2-a][1,4] diazacyclopentadecine-14a-carboxamide
N-((2R,6S,13aS,14aR,16aS)-14a-(cyclopropyl-sulfonylcarbamoyl)-12,12-difluoro-5,16-dioxo-2-(3-(trifluoromethoxy)phenanthridin-6-yloxy)octadecahydrocyclopropa[e]pyrrolo[1,2-a][1,4]diazacyclopentadecin-6-yl)-5-methylisoxazole-3-carboxamide
N-((2R,6S,13aS,14aR,16aS)-14a-(cyclopropyl- 14a-(1-methylcyclopropylsulfonylcarbamoyl)-5,16-dioxo-2-(3-(trifluoromethyl)phenanthridin-6-yloxy)octadecahydrocyclopropa[e]pyrrolo[1,2-a][1,4]diazacyclopentadecin-6-yl)-5-methylisoxazole-3-carboxamide
(2R,6S,13aS,14aR,16aS)-12,12-difluoro-2-(3-methoxyphenanthridin-6-yloxy)-6-(1-methyl-1H-pyrazole-3-carboxamido)-N-(1-methylcyclopropylsulfonyl)-5,16-dioxooctadecahydrocyclopropa[e]pyrrolo[1,2-a][1,4]diazacyclopentadecine-14a-carboxamide
(2R,6S,13aS,14aR,16aS)-2-(3,9-difluorophenanthridin-6-yloxy)-12,12-difluoro-6-(1-methyl-1H-pyrazole-3-carboxamido)-N-(1-methylcyclopropylsulfonyl)-5,16-dioxooctadecahydrocyclopropa[e]pyrrolo[1,2-a][1,4]diazacyclopentadecine-14a-carboxamide
N-((2R,6S,13aS,14aR,16aS)-12,12-difluoro-2-(3-methoxyphenanthridin-6-yloxy)-14a-(1-methylcyclopropylsulfonylcarbamoyl)-5,16-dioxooctadecahydrocyclopropa[e]pyrrolo[1,2-a][1,4]diazacyclopentadecin-6-yl)-5-methylisoxazole-3-carboxamide
N-((2R,6S,13aS,14aR,16aS)-2-(3,9-difluorophenanthridin-6-yloxy)-12,12-difluoro-14a-(1-methylcyclopropylsulfonylcarbamoyl)-5,16-dioxooctadecahydrocyclopropa[e]pyrrolo[1,2-a][1,4]diazacyclopentadecin-6-yl)-5-methylisoxazole-3-carboxamide
sulfonylcarbamoyl)-12,12-difluoro-5,16-dioxo-2-(3-(trifluoromethyl)phenanthridin-6-yloxy)octadecahydrocyclopropa[e]pyrrolo[1,2-a][1,4]diazacyclopentadecin-6-yl)-5-methylisoxazole-3-carboxamide
(2R,6S,13aS,14aR,16aS)-N-(cyclopropylsulfonyl)-12,12-difluoro-2-(3-methoxyphenanthridin-6-yloxy)-6-(1-methyl-1H-pyrazole-3-carboxamido)-5,16-dioxooctadecahydrocyclopropa[e]pyrrolo[1,2-a][1,4]diazacyclopentadecine-14a-carboxamide
(2R,6S,13aS,14aR,16aS)-N-(cyclopropylsulfonyl)-2-(3,9-difluorophenanthridin-6-yloxy)-12,12-difluoro-6-(1-methyl-1H-pyrazole-3-carboxamido)-5,16-dioxooctadecahydrocyclopropa[e]pyrrolo[1,2-a][1,4]diazacyclopentadecine-14a-carboxamide
N-((2R,6S,13aS,14aR,16aS)-14a-(cyclopropylsulfonylcarbamoyl)-12,12-difluoro-2-(3-methoxyphenanthridin-6-yloxy)-5,16-dioxooctadecahydrocyclopropa[e]pyrrolo[1,2-a][1,4]diazacyclopentadecin-6-yl)-5-methylisoxazole-3-carboxamide
N-((2R,6S,13aS,14aR,16aS)-14a-(cyclopropylsulfonylcarbamoyl)-2-(3,9-difluorophenanthridin-6-yloxy)-12,12-difluoro-5,16-dioxooctadecahydrocyclopropa[e]pyrrolo[1,2-a][1,4]diazacyclopentadecin-6-yl)-5-methylisoxazole-3-carboxamide It is understood that the embodiments of the invention discussed below with respect to the preferred variable selections can be taken alone or in combination with one or more of the other embodiments, or preferred variable selections, of the invention, as if each combination were explicitly listed herein.

In other aspects, the invention provides a pharmaceutical composition comprising a therapeutically effective amount of a compound of the invention (e.g., a compound of formula I, or any formulae as described herein), or a pharmaceutically acceptable salt, ester, or prodrug thereof, in combination with a pharmaceutically acceptable carrier or excipient.

In another aspect, the invention provides a pharmaceutical composition comprising a therapeutically effective amount of a compound described herein, or an embodiment or example described herein, or a pharmaceutically acceptable salt, ester, hydrate, solvate, polymorph, or prodrug thereof, in combination with a pharmaceutically acceptable carrier or excipient.

According to another embodiment, the pharmaceutical compositions of the present invention may further contain one or more other anti-HCV agents. Examples of anti-HCV agents include, but are not limited to, α-interferon; β-interferon; pegylated interferon-α; pegylated interferon-lambda; ribavirin; viramidine; R-5158; nitazoxanide; amantadine; Debio-025, NIM-811; HCV polymerase inhibitors such as R7128, R1626, R4048, T-1106, PSI-7851, PF-00868554, ANA-598, IDX184, IDX102, IDX375, GS-9190, VCH-759, VCH-916, MK-3281, BCX-4678, MK-3281, VBY708, ANA598, GL59728 or GL60667; BMS-790052; BMS-791325; BMS-650032; HCV entry, helicase or internal ribosome entry site inhibitors; HCV NS5A inhibitors; or other HCV replication inhibitors such as GS-9132, ACH-1095, AP-H005, A-831, A-689, AZD2836. For further details see S. Tan, A. Pause, Y. Shi, N. Sonenberg, Hepatitis C Therapeutics: Current Status and Emerging Strategies, *Nature Rev. Drug Discov.*, 1, 867-881 (2002); WO 00/59929 (2000); WO 99/07733 (1999); WO 00/09543 (2000); WO 99/50230 (1999); U.S. Pat. No. 5,861,297 (1999); and US2002/0037998 (2002).

According to an additional embodiment, the pharmaceutical compositions of the present invention may further contain another HCV protease inhibitor, such as telaprevir, boceprevir, ITMN-191, BI-201335, TMC-435, MK-7009, VBY-376, VX-500, VX-813, PHX-B, ACH-1625, IDX136, or IDX316.

In other embodiments, the invention provides a pharmaceutical composition further comprising pegylated interferon, another anti-viral, anti-bacterial, anti-fungal or anti-cancer agent, or an immune modulator, and/or further comprising a cytochrome P450 monooxygenase inhibitor or a pharmaceutically acceptable salt thereof. In certain embodiments, the cytochrome P450 monooxygenase inhibitor is ritonavir.

In another aspect, the invention provides for the use of a compound of the invention to manufacture an agent for preventing or treating viral infection. In another aspect, the invention provides for the use of a compound of the invention to manufacture an agent for preventing or treating hepatitis C viral infection. The present invention also contemplates the use of a solvate (e.g., hydrate) of a compound of the invention to manufacture pharmaceutical compositions for preventing or treating hepatitis C infection. As used herein, "solvate" refers to the physical association of a compound of the invention with one or more solvent molecule, whether organic or inorganic. This physical association often includes hydrogen bonding. In certain instances, the solvate is capable of isolation, for example, when one or more solvate molecules are incorporated in the crystal lattice of the crystalline solid.

In another embodiment, the compounds or pharmaceutical compositions of the invention are administered with ritonavir, either simultaneously or sequentially. In certain embodiments, a compound or a pharmaceutical composition of the invention is administered in the same composition as ritonavir. In another embodiment, a compound or a pharmaceutical composition thereof of the invention is administered in a different composition than ritonavir.

According to yet another embodiment, the pharmaceutical compositions of the present invention may further comprise inhibitor(s) of other targets in the HCV life cycle, including, but not limited to, helicase, polymerase, metalloprotease, CD81, NS5A, cyclophilin, and internal ribosome entry site (IRES).

In one aspect, the invention provides a method of treating a viral infection in a subject, comprising administering to the subject a therapeutically effective amount of a compound of the invention (e.g., a compound of formula I or I' described herein), or a pharmaceutically acceptable salt, ester or prodrug thereof, or a pharmaceutical composition comprising the same.

According to a further embodiment, the present invention includes methods of treating hepatitis C infections in a subject in need of such treatment by administering to said subject an anti-HCV virally effective amount or an inhibitory amount of the compounds or pharmaceutical compositions of the present invention.

According to another embodiment, the present invention includes methods of treating hepatitis C infections in a subject in need of such treatment by administering to said subject a compound or a pharmaceutical composition of the present invention. The methods can further include administration of an additional therapeutic agent, including another antiviral agent or an anti-HCV agent as described hereinabove. The additional agent can be co-administered (such as concurrently administered or sequentially administered) with a compound (a pharmaceutically acceptable salt, ester or prodrug thereof) or a pharmaceutical composition of the present invention. The additional agent(s) and a compound (or a pharmaceutically acceptable salt, ester or prodrug thereof) of the present invention can be formulated in the same composition, or in different compositions but co-administered concurrently or sequentially. The methods herein can further include the step of identifying that the subject is in need of treatment for hepatitis C infection. The identification can be by subjective (e.g., health care provider determination) or objective (e.g., diagnostic test) means.

In one aspect, the invention provides a method of inhibiting the replication of hepatitis C virus, the method comprising contacting a hepatitis C virus with an effective amount of a compound or pharmaceutical composition of the invention.

In another embodiment, the invention provides a method as described above, further comprising administering an additional anti-hepatitis C virus agent. Examples of anti-hepatitis C virus agents include, but are not limited to, α-interferon; β-interferon; pegylated interferon-α; pegylated interferon-lambda; ribavirin; viramidine; R-5158; nitazoxanide; amantadine; Debio-025, NIM-811; HCV polymerase inhibitors such as R7128, R1626, R4048, T-1106, PSI-7851, PF-00868554, ANA-598, IDX184, IDX102, IDX375, GS-9190, VCH-759, VCH-916, MK-3281, BCX-4678, MK-3281, VBY708, ANA598, GL59728 or GL60667; BMS-790052; BMS-791325; BMS-650032; HCV entry, helicase or internal ribosome entry site inhibitors; or other HCV replication inhibitors such as GS-9132, ACH-1095, AP-H005, A-831, A-689, AZD2836. For further details see S. Tan, A. Pause, Y. Shi, N. Sonenberg, Hepatitis C Therapeutics: Current Status and Emerging Strategies, *Nature Rev. Drug Discov.*, 1, 867-881 (2002); WO 00/59929 (2000); WO 99/07733 (1999); WO 00/09543 (2000); WO 99/50230 (1999); U.S. Pat. No. 5,861,297 (1999); and US2002/0037998 (2002). Preferably, a compound or a pharmaceutical composition of the present invention is co-administered with, or used in combination with, pegylated interferon (e.g., pegylated interferon alpha-2a or 2b) and ribavirin. Ritonavir or another cytochrome P450 monooxygenase inhibitor can also be used to enhance the pharmacokinetics of the compound of the present invention. The patient being treated is preferably infected with HCV genotype-1 (e.g., genotype 1a or 1b). Patients infected with other HCV genotypes, such as genotypes 2, 3, 4, 5 or 6, can also be treated with a compound or a pharmaceutical composition of the present invention.

In another embodiment, the invention provides a method as described above, further comprising administering another HCV protease inhibitor, an HCV polymerase inhibitor, an HCV helicase inhibitor, or an internal ribosome entry site (IRES) inhibitor, such as telaprevir, boceprevir, ITMN-191, BI-201335, TMC-435, MK-7009, VBY-376, VX-500, VX-813, PHX-B, ACH-1625, IDX136, IDX316, pegylated interferon, another anti-viral, anti-bacterial, anti-fungal or anti-cancer agent, or an immune modulator, and/or further comprising a cytochrome P450 monooxygenase inhibitor or a pharmaceutically acceptable salt thereof. In certain embodiments, the cytochrome P450 monooxygenase inhibitor is ritonavir.

An additional embodiment of the present invention includes methods of treating biological samples by contacting the biological samples with the compounds of the present invention.

Yet another aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group. The number of carbon atoms in a hydrocarbyl substituent can be indicated by the prefix "$C_x$-$C_y$," where x is the minimum and y is the maximum number of carbon atoms in the substituent. Likewise, a $C_x$ chain means a hydrocarbyl chain containing x carbon atoms.

The prefix "halo" indicates that the substituent to which the prefix is attached is substituted with one or more independently selected halogen radicals. For example, "$C_1$-$C_8$haloalkyl" means a $C_1$-$C_8$ alkyl substituent wherein at least one hydrogen radical is replaced with a halogen radical.

If a linking element in a depicted structure is "absent", then the left element in the depicted structure is directly linked to the right element in the depicted structure. For example, if a chemical structure is depicted as X-(L)$_n$-Y wherein L is absent or n is 0, then the chemical structure is X—Y.

The term "alkyl" as used herein, refers to a saturated, straight- or branched-chain hydrocarbon radical preferably containing one to eight carbon atoms ($C_1$-$C_8$ alkyl). Examples of alkyl radicals include, but are not limited to, methyl, ethyl, propyl, isopropyl, n-butyl, tert-butyl, neopentyl, n-hexyl, heptyl, octyl radicals and the like.

The term "alkenyl" as used herein, denotes a straight- or branched-chain hydrocarbon radical containing one or more double bonds and preferably containing two to eight carbon atoms ($C_2$-$C_8$ alkenyl). Alkenyl groups include, but are not limited to, for example, ethenyl, propenyl, butenyl, 1-methyl-2-buten-1-yl, heptenyl, octenyl and the like.

The term "alkynyl" as used herein, denotes a straight- or branched-chain hydrocarbon radical containing one or more triple bonds and preferably containing two to eight carbon atoms ($C_2$-$C_8$ alkynyl). Representative alkynyl groups include, but are not limited to, for example, ethynyl, 1-propynyl, 1-butynyl, heptynyl, octynyl and the like.

The term "cycloalkyl" denotes a monovalent group derived from a monocyclic or polycyclic saturated carbocyclic ring compound and preferably containing 3 to 14 carbon ring atoms ($C_3$-$C_{14}$ cycloalkyl). Examples of cycloalkyl include, but not limited to, cyclopropyl, cyclobutyl, cyclopentyl, cyclohexyl, bicycle [2.2.1] heptyl, and bicycle [2.2.2] octyl and the like.

The terms "carbocycle" or "carbocyclic" or "carbocyclyl" refer to a saturated (e.g., "cycloalkyl"), partially saturated (e.g., "cycloalkenyl" or "cycloalkynyl") or completely unsaturated (e.g., "aryl") ring system containing zero heteroatom ring atom and preferably containing 3 to 14 carbon ring atoms ($C_3$-$C_{14}$carbocyclyl, such as $C_3$-$C_{14}$cycloalkyl). A carbocyclyl may be, without limitation, a single ring, or two or more fused or covalently linked rings, or bridged or spiro rings. A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, fluorenyl, indanyl, 1,2,3,4-tetrahydro-naphthyl, indenyl, isoindenyl, bicyclodecanyl, anthracenyl, phenanthrene, benzonaphthenyl (also known as "phenalenyl"), decalinyl, and norpinanyl and the like. A carbocyclyl group can be attached to the parent molecular moiety through any substitutable carbon atom of the group.

The term "aryl" refers to an aromatic carbocyclyl containing from 6 to 14 carbon ring atoms. Non-limiting examples of aryls include phenyl, naphthalenyl, anthracenyl, and indenyl and the like. An aryl group can be connected to the parent molecular moiety through any substitutable carbon atom of the group.

The term "heteroaryl" means an aromatic heterocyclyl typically containing from 5 to 14 ring atoms. Non-limiting examples of five-membered heteroaryls include imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; and isothiazolyl. Non-limiting examples of six-membered heteroaryls include pyridinyl; pyrazinyl; pyrimidinyl; pyridazinyl; and 1,3,5-, 1,2,4-, and 1,2,3-triazinyl. Non-limiting examples of 6/5-membered fused ring heteroaryls include benzothiofuranyl, isobenzothiofuranyl, benzisoxazolyl, benzoxazolyl, purinyl, and anthranilyl. Non-limiting examples of 6/6-membered fused ring heteroaryls include quinolinyl; isoquinolinyl; and benzoxazinyl (including cinnolinyl and quinazolinyl).

The term "heterocycloalkyl" refers to a non-aromatic 3-, 4-, 5-, 6- or 7-membered ring or a bi- or tri-cyclic group fused system, where at least one of the ring atoms is a heteroatom, and where (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl and the like.

The terms "heterocyclic" or "heterocycle" or "heterocyclyl" refer to a saturated (e.g., "heterocycloalkyl"), partially unsaturated (e.g., "heterocycloalkenyl" or "heterocycloalkynyl") or completely unsaturated (e.g., "heteroaryl") ring system preferably containing 3 to 14 ring atoms, where at least one of the ring atoms is a heteroatom (i.e., nitrogen, oxygen or sulfur), with the remaining ring atoms being independently selected from the group consisting of carbon, nitrogen, oxygen and sulfur. A heterocyclic or heterocycle or heterocyclyl may be, without limitation, a single ring, or two or more fused or covalently linked rings, or bridged or spiro rings. A heterocyclyl group can be linked to the parent molecular moiety via any substitutable carbon or nitrogen atom in the group, provided that a stable molecule results. A heterocyclyl may be, without limitation, a single ring. Non-limiting examples of single-ring heterocyclyls include furanyl, dihydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazoly, pyranyl, dihydropyranyl, pyridinyl, piperidinyl, pyridazinyl, pyrimidinyl, pyrazinyl, piperazinyl, triazinyl, isoxazinyl, oxazolidinyl, isoxazolidinyl, oxathiazinyl, oxadiazinyl, morpholinyl, azepinyl, oxepinyl, thiepinyl, or diazepinyl. A heterocyclyl may also include, without limitation, two or more rings fused together, such as, for example, naphthyridinyl, thiazolpyrimidinyl, thienopyrimidinyl, pyrimidopyrimidinyl, or pyridopyrimidinyl. A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

The terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I,

—OH, protected hydroxy, alkoxy, oxo, thiooxo,

—$NO_2$, —CN, $CF_3$, $N_3$,

—$NH_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-carbocyclyl, —C(O)-aryl, —C(O)-heteroaryl, —C(O)-heterocyclyl, —$CONH_2$, —CONH-alkyl, —CONH-alkenyl, —CONH-alkynyl, —CONH-carbocyclyl, —CONH-aryl, —CONH-heteroaryl, —CONH-heterocyclyl, —$OCO_2$-alkyl, —$OCO_2$-alkenyl, —$OCO_2$-alkynyl, —$OCO_2$-carbocyclyl, —$OCO_2$-aryl, —$OCO_2$-heteroaryl, —$OCO_2$-heterocyclyl, —$OCONH_2$, —OCONH-alkyl, —OCONH-alkenyl, —OCONH-alkynyl, —OCONH-carbocyclyl, —OCONH-aryl, —OCONH-heteroaryl, —OCONH-heterocyclyl, —NHC(O)-alkyl, —NHC(O)-alkenyl, —NHC(O)-alkynyl, —NHC(O)-carbocyclyl, —NHC(O)-aryl, —NHC(O)-heteroaryl, —NHC(O)-heterocyclyl, —$NHCO_2$-alkyl, —$NHCO_2$-alkenyl, —$NHCO_2$-alkynyl, —$NHCO_2$-carbocyclyl, —$NHCO_2$-aryl, —$NHCO_2$-heteroaryl, —$NHCO_2$-heterocyclyl, —NHC(O)$NH_2$, —NHC(O)NH-alkyl, —NHC(O)NH-alkenyl, —NHC(O)NH-alkenyl, —NHC(O)NH-carbocyclyl, —NHC(O)NH-aryl, —NHC(O)NH-heteroaryl, —NHC(O)NH-heterocyclyl, NHC(S)NH$_2$, —NHC(S)NH-alkyl, —NHC(S)NH-alkenyl, —NHC(S)NH-alkynyl, —NHC(S)NH-carbocyclyl, —NHC(S)NH-aryl, —NHC(S)NH-heteroaryl, —NHC(S)NH-heterocyclyl, —NHC(NH)NH$_2$, —NHC(NH)NH-alkyl, —NHC(NH)NH-alkenyl, —NHC(NH)NH-alkenyl, —NHC(NH)NH-carbocyclyl, —NHC(NH)NH-aryl, —NHC(NH)NH-heteroaryl, —NHC(NH)NH-heterocyclyl, —NHC(NH)-alkyl, —NHC(NH)-alkenyl, —NHC(NH)-alkenyl, —NHC(NH)-carbocyclyl, —NHC(NH)-aryl, —NHC(NH)-heteroaryl, —NHC(NH)-heterocyclyl, —C(NH)NH-alkyl, —C(NH)NH-alkenyl, —C(NH)NH-alkynyl, —C(NH)NH-carbocyclyl, —C(NH)NH-aryl, —C(NH)NH-heteroaryl, —C(NH)NH-heterocyclyl, —S(O)-alkyl, —S(O)-alkenyl, —S(O)-alkynyl, —S(O)-carbocyclyl, —S(O)-aryl, —S(O)-heteroaryl, —S(O)-heterocyclyl —SO$_2$NH$_2$, —SO$_2$NH-alkyl, —SO$_2$NH-alkenyl, —SO$_2$NH-alkynyl, —SO$_2$NH-carbocyclyl, —SO$_2$NH-aryl, —SO$_2$NH-heteroaryl, —SO$_2$NH-heterocyclyl, —NHSO$_2$-alkyl, —NHSO$_2$-alkenyl, —NHSO$_2$-alkynyl, —NHSO$_2$-carbocyclyl, —NHSO$_2$-aryl, —NHSO$_2$-heteroaryl, —NHSO$_2$-heterocyclyl,

—CH$_2$NH$_2$, —CH$_2$SO$_2$CH$_3$,

-alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S-alkyl, —S-alkenyl, —S-alkynyl, —S-carbocyclyl, —S-aryl, —S-heteroaryl, —S-heterocyclyl, or methylthiomethyl.

It is understood that the aryls, heteroaryls, carbocycles, heterocycles, alkyls, and the like can be further substituted.

The terms "halo" and "halogen," as used herein, refer to an atom selected from fluorine, chlorine, bromine and iodine.

Any divalent group having two points of connection to two other groups may be aligned in either direction, e.g., the term "—C(O)O—" is interpreted to include both —C(O)O— and —OC(O)—.

The term "subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

The term "leaving group," or "LG", as used herein, refers to any group that leaves in the course of a chemical reaction involving the group and includes but is not limited to halogen, brosylate, mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, Protective Groups in Organic Synthesis, 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilylethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, Protective Groups in Organic Synthesis, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "alkylamino" refers to a group having the structure —N(R$_a$R$_b$), where R$_a$ and R$_b$ are independent H or alkyl.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups, and elixirs. In addition to the active compounds, the liquid dosage forms may contain inert diluents commonly used in the art such as, for example, water, alcohol or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, polysorbate, dimethylformamide, oils (in particular, cottonseed, groundnut, corn, germ, olive, castor, and sesame oils), mono- or di-glycerides, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, antioxidants, sweetening, flavoring, and perfuming agents. The liquid dosage form can also be encapsulated in a gelatin capsule, wherein a compound of the present invention can be dissolved in a pharmaceutically acceptable carrier containing, for example, one or more solubilizating agents (e.g., polysorbate 80 and mono and diglycerides), and other suitable excipients (e.g., an antioxidants such as ascorbyl palmitate, or a sweetening or flavoring agent).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Immediate release forms are also contemplated by the present invention.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Preferably, a compound of the invention is formulated in a solid dispersion, where the compound can be molecularly dispersed in a matrix which comprises a pharmaceutically acceptable, hydrophilic polymer. The matrix may also contain a pharmaceutically acceptable surfactant. Suitable solid dispersion technology for formulating a compound of the invention includes, but is not limited to, melt extrusion, spray drying, or solvent evaporization.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, viral infections are treated or prevented in a subject, such as a human or another animal, by administering to the subject a therapeutically effective amount of a compound of the invention (or a pharmaceutically acceptable salt, ester or prodrug thereof), in such amounts and for such time as is necessary to achieve the desired result. The term "therapeutically effective amount" of a compound of the invention, as used herein, means a sufficient amount of the compound so as to decrease the viral load in a subject and/or decrease the subject's HCV symptoms. As is well understood in the medical arts a therapeutically effective amount of a compound of this invention will be at a reasonable benefit/risk ratio applicable to any medical treatment.

Antiviral Activity

An inhibitory amount or dose of the compounds of the present invention may range from about 0.1 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a subject such as a human or lower mammal by administering to the subject an anti-hepatitis C virally effective amount or an inhibitory amount of a compound of the present invention, in such amounts and for such time as is necessary to achieve the desired result. An additional method of the present invention is the treatment of biological samples with an inhibitory amount of a compound of composition of the present invention in such amounts and for such time as is necessary to achieve the desired result.

The term "anti-hepatitis C virally effective amount" of a compound of the invention, as used herein, means a sufficient amount of the compound so as to decrease the viral load in a biological sample or in a subject. As well understood in the medical arts, an anti-hepatitis C virally effective amount of a compound of this invention will be at a reasonable benefit/risk ratio applicable to any medical treatment.

The term "inhibitory amount" of a compound of the present invention means a sufficient amount to decrease the hepatitis C viral load in a biological sample or a subject. It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin, which may be intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof; or stem cells. Thus, another embodiment of the present invention is a method of treating a biological sample by contacting said biological sample with an inhibitory amount of a compound or pharmaceutical composition of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present invention comprise administration to a patient in need of such treatment from about 10 mg to about 1000 mg of the compound(s) of this invention per day in single or multiple doses. In another embodiment, the treatment regimen comprises administration to a patient in need of such treatment from about 25 mg to about 6000 mg of a compound(s) of this invention per day in single or multiple doses, either with or without a cytochrome P450 monooxygenase inhibitor such as ritonavir. The suitable daily dose for the co-administered cytochrome P450 monooxygenase inhibitor (e.g., ritonavir) can range, without limitation, from 10 to 200 mg. Preferably, a compound(s) of the present invention, or a combination of a compound(s) of the invention and ritonavir, is administered once daily or twice daily to achieve the desired daily dose amount. For instance, when used without ritonavir, a compound of the present invention can be administered to a patient twice a day with a total daily dose of 4000, 4200, 4400, 4600, 4800 or 5000 mg. For another instance, when used in combination with ritonavir, a compound of the present invention can be administered to a patient once or twice a day with a total daily dose of 200, 400, 600 or 800 mg, where the amount of ritonavir can be 25, 50 or 100 mg per administration.

Synthetic Methods

The compounds and processes of the present invention will be better understood in connection with the following synthetic examples that illustrate the methods by which the compounds of the invention may be prepared.

Definitions of variables in the structures in the schemes herein are commensurate with those of corresponding positions in the formulae delineated herein.

The compounds described herein contain one or more asymmetric centers and thus give rise to enantiomers, diastereomers, and other stereoisomeric forms that may be defined, in terms of absolute stereochemistry, as (R)— or (S)—, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXAMPLES

The compounds and processes of the present invention will be better understood in connection with the following examples, which are intended as an illustration only and not to limit the scope of the invention. The following examples can be prepared according to the schemes as described above, or according to the synthetic steps as described below. Various changes and modifications to the disclosed embodiments will be apparent to those skilled in the art and such changes and modifications including, without limitation, those relating to the chemical structures, substituents, derivatives, formulations and/or methods of the invention may be made

Example 1 tert-butyl(2R,6S,13aS,14aR,16aS)-14a-(cyclopropyl-
sulfonylcarbamoyl)-12,12-difluoro-5,16-dioxo-2-
(quinoxalin-2-yloxy)octadecahydrocyclopropa[e]
pyrrolo[1,2-a][1,4]diazacyclopentadecin-6-
ylcarbamate

Example 1a (2S,6S,13aS,14aR,16aS,Z)-ethyl 2-(benzoyloxy)-6-
(tert-butoxycarbonylamino)-5, 16-dioxo-1,2,3,5,6,7,
8,9,10,11,13a,14,14a,15,16,16a-hexadecahydrocy-
clopropa[e]pyrrolo[1,2-a][1,4]
diazacyclopentadecine-14a-carboxylate To a solution of (2S,6S,13aS,14aR,16aS,Z)-ethyl 6-(tert-butoxycarbonylamino)-2-hydroxy-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (2.0 g, 4.1 mmol) in dichloromethane (4.1 ml) cooled to 0° C. was added N-ethyl-N-isopropylpropan-2-amine (2.83 ml, 16.2 mmol) and 1-methylimidazole (0.097 ml, 1.2 mmol) followed by benzoic anhydride (1.83 g, 8.10 mmol). The solution was stirred at room temperature for 16 h, DMAP (9.3 mg, 0.076 mmol) was added and the reaction mixture stirred

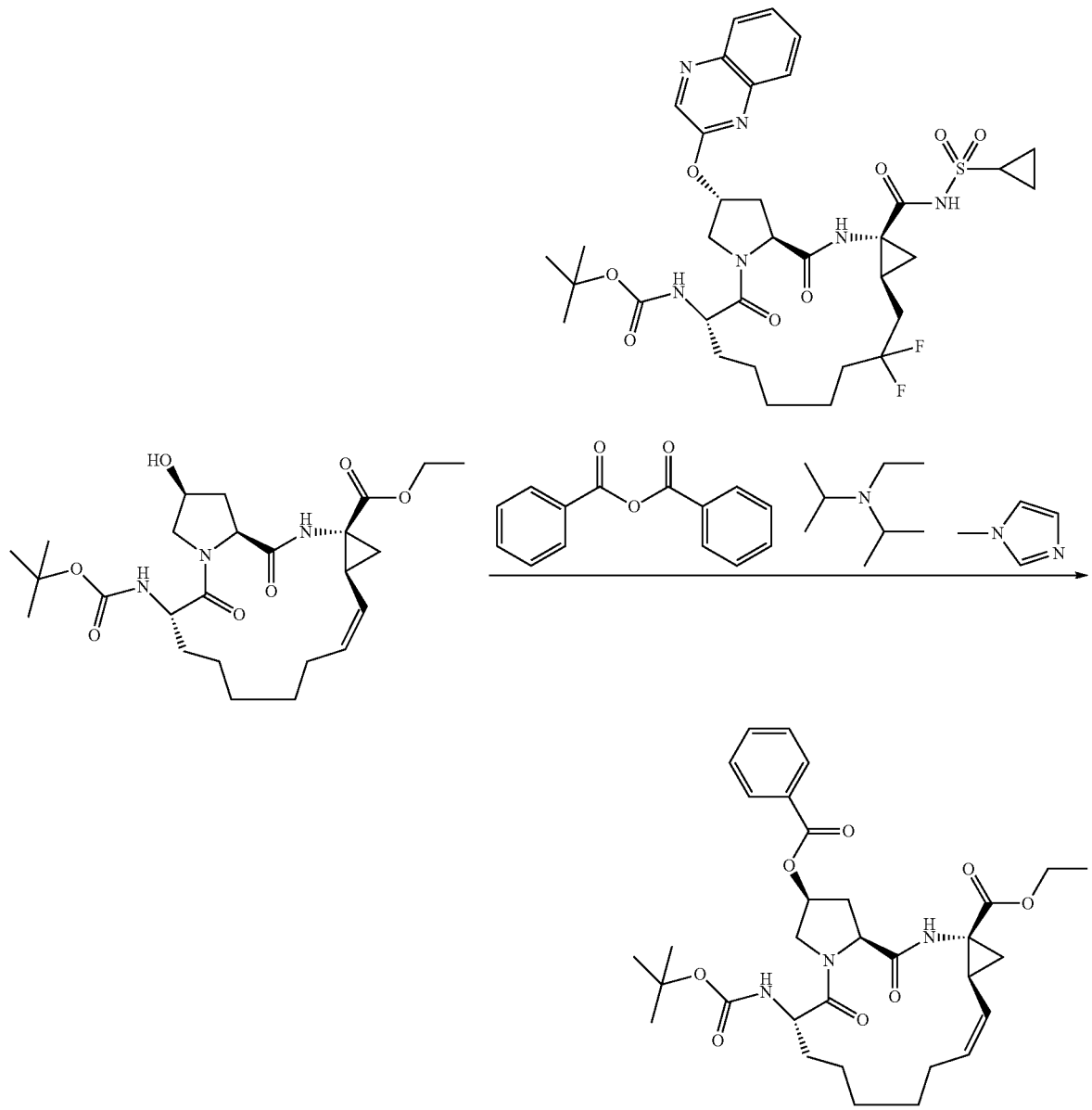

for 2.5 h. The reaction mixture was diluted with ethyl acetate (150 ml) and washed with HCl (1 N, 50 ml×2), water and brine. The organic layer was dried (anhydrous sodium sulfate), concentrated and purified by flash chromatography on silica gel (dichloromethane/methanol=40/1) to provide the title compound (2.06 g, 83% yield) as a foamy white solid.

Example 1b (2S,6S,12S,13aS,14aR,16aS)-ethyl 2-(benzoyloxy)-6-(tert-butoxycarbonylamino)-12-hydroxy-5,16-dioxooctadecahydrocyclopropa[e]pyrrolo[1,2-a][1,4]diazacyclopentadecine-14a-carboxylate

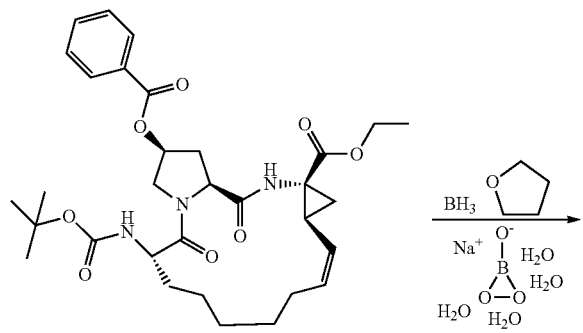

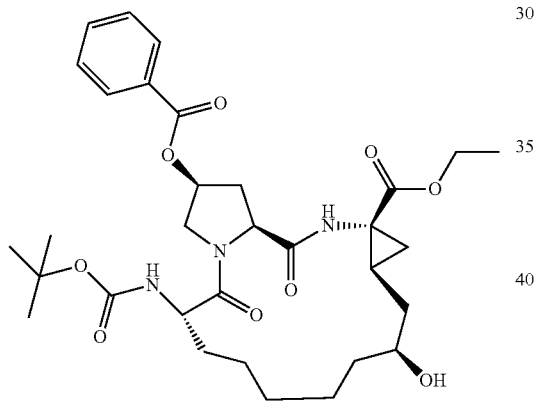

To a solution of (2S,6S,13aS,14aR,16aS,Z)-ethyl 2-(benzoyloxy)-6-(tert-butoxycarbonylamino)-5, 16-dioxo-1,2,3,5,6,7,8,9,10,11,13a,14,14a,15,16,16a-hexadecahydrocyclopropa[e]pyrrolo[1,2-a][1, 4]diazacyclopentadecine-14a-carboxylate (2.06 g, 3.45 mmol) in tetrahydrofuran (34 ml) was added borane-tetrahydrofuran complex (19 ml, 1M, 19.00 mmol) in one portion at 0° C. The mixture was stirred at 0° C. for 20 min and then at room temperature for 20 min. The reaction mixture was quenched by adding water (70 ml) dropwise at 0° C. followed by the addition of sodium perborate tetrahydrate (2.92 g, 19.0 mmol). The mixture was stirred at room temperature overnight. The reaction mixture was diluted with ethyl acetate (300 ml) and washed with water (50 ml×2) and brine (50 ml). The combined aqueous layer was back-extracted with ethyl acetate (75 ml×2). The organic layers were dried (anhydrous sodium sulfate) and concentrated to give a white foamy solid (3.2 g). The residue was purified by flash chromatography on silica gel (dichloromethane/methanol=40/1, 30/1) followed by a second purification by reverse phase HPLC (acetonitrile/water (0.1% TFA)=30/70 to 100/0, 15 min) to provide (2S,6S,12S,13aS,14aR,16aS)-ethyl 2-(benzoyloxy)-6-(tert-butoxycarbonylamino)-12-hydroxy-5,16-dioxooctadecahydrocyclopropa[e]pyrrolo[1,2-a][1,4]diazacyclopentadecine-14a-carboxylate (0.43 g, 0.70 mmol, 20% yield).

Example 1c (2S,6S,13aS,14aR,16aS)-ethyl 2-(benzoyloxy)-6-(tert-butoxycarbonylamino)-5, 2, 16-trioxooctadecahydrocyclopropa[e]pyrrolo[1,2-a][1,4]diazacyclopentadecine-14a-carboxylate

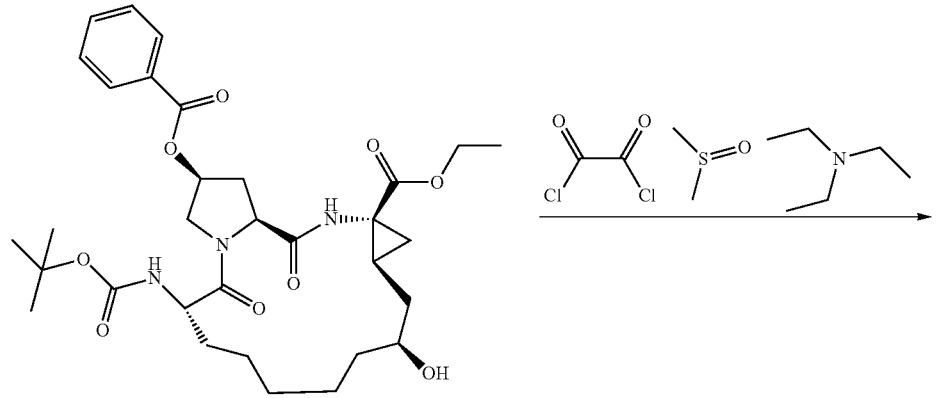

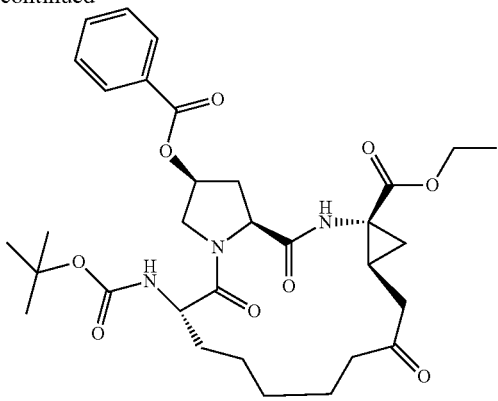

To a solution of oxalyl chloride (0.092 ml, 1.05 mmol) in dichloromethane (1.75 ml) at −78° C. was added dropwise DMSO (0.149 ml, 2.10 mmol). The reaction mixture was stirred for 10 min and then a solution of (2S,6S,12S,13aS,14aR,16aS)-ethyl 2-(benzoyloxy)-6-(tert-butoxycarbonylamino)-12-hydroxy-5,16-dioxooctadecahydrocyclopropa[e]pyrrolo[1,2-a][1,4]diazacyclopentadecine-14a-carboxylate (Example 1b, 0.43 g, 0.698 mmol) in dichloromethane (4 ml) was added dropwise. The reaction mixture was stirred at −78° C. for 30 min and triethylamine (0.730 ml, 5.24 mmol) was added dropwise. The reaction mixture was stirred at −78° C. for 15 min and warmed to room temperature and stirred for 1.5 hr. The reaction mixture was quenched with water, stirred for 30 min and extracted with dichloromethane and the organic layer dried over anhydrous sodium sulfate, filtered, and evaporated under reduced pressure. The residue was purified by flash chromatography on silica gel (dichloromethane/methanol=40/1) to provide the title compound (2S,6S,13aS,14aR,16aS)-ethyl 2-(benzoyloxy)-6-(tert-butoxycarbonylamino)-5,12,16-trioxooctadecahydrocyclopropa[e]pyrrolo[1,2-a][1,4]diazacyclopentadecine-14a-carboxylate (0.36 g, 0.59 mmol, 84% yield).

Example 1d (2S,6S,13aS,14aR,16aS)-ethyl 2-(benzoyloxy)-6-(tert-butoxycarbonylamino)-12, 2-difluoro-5,16-dioxooctadecahydrocyclopropa[e]pyrrolo [1,2-a][1,4]diazacyclopentadecine-14a-carboxylate

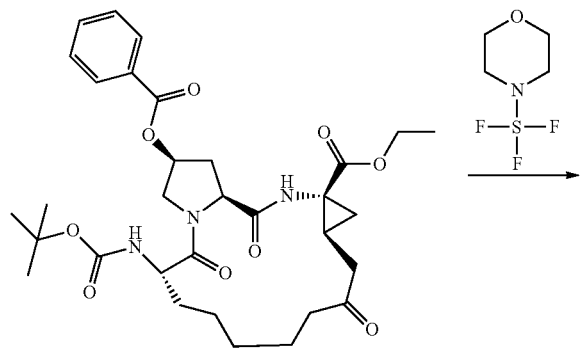

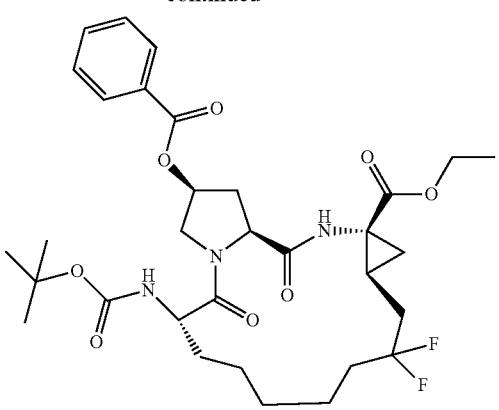

To (2S,6S,13aS,14aR,16aS)-ethyl 2-(benzoyloxy)-6-(tert-butoxycarbonylamino)-5, 12, 16-trioxooctadecahydrocyclopropa[e]pyrrolo[1,2-a][1,4]diazacyclopentadecine-14a-carboxylate (Example 1c, 307 mg, 0.500 mmol) was added MORPHOLINOSULFUR TRIFLUORIDE (2.44 mL, 20.0 mmol). The mixture was sonicated to dissolve all solids. The solution was stirred at room temperature for 16 h., diluted with ethyl acetate, and added dropwise to a mixture of ice and aq. sodium carbonate (10%, 5 ml). The layers were separated, and the aqueous layer was back-extracted with ethyl acetate (10 ml×2). The combined organic layer was washed with 50% brine and dried over anhydrous sodium sulfate, filtered, and evaporated under reduced pressure to give a light yellow oil (75 mg). This material was purified by reverse phase HPLC (acetonitrile/water (0.1% TFA)=50/50 to 100/0, 15 min) to provide the title compound (2S,6S,13aS,14aR,16aS)-ethyl 2-(benzoyloxy)-6-(tert-butoxycarbonylamino)-12,12-difluoro-5,16-dioxooctadecahydrocyclopropa[e]pyrrolo[1,2-a][1,4]diazacyclopentadecine-14a-carboxylate (64.9 mg, 0.102 mmol, 20.4% yield).

Example 1e (2S,6S,13aS,14aR,16aS)-ethyl 6-(tert-butoxycarbonylamino)-12,12-difluoro-2-hydroxy-5,16-dioxooctadecahydrocyclopropa[e]pyrrolo[1,2-a][1,4]diazacyclopentadecine-14a-carboxylate

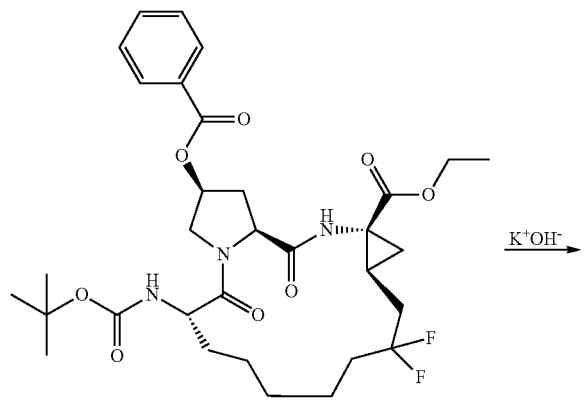

To a solution of (2S,6S,13aS,14aR,16aS)-ethyl 2-(benzoyloxy)-6-(tert-butoxycarbonylamino)-12,12-difluoro-5,16-dioxooctadecahydrocyclopropa[e]pyrrolo[1,2-a][1,4]diazacyclopentadecine-14a-carboxylate (Example 1d, 94.75 mg, 0.149 mmol) in ethanol (0.414 ml) at 0° C. was added dropwise a solution of KOH (0.25 ml, 0.250 mmol, 1 N in ethanol). The solution was stirred at 0° C. for 50 min and LC/MS showed completion. The reaction mixture was quenched by dropwise addition of HCl (1 N in dioxane/ethyl acetate, 0.25 ml) at 0° C. Another portion of (2S,6S,13aS,14aR,16aS)-ethyl 2-(benzoyloxy)-6-(tert-butoxycarbonylamino)-12,12-difluoro-5,16-dioxooctadecahydrocyclopropa[e]pyrrolo[1,2-a][1,4]diazacyclopentadecine-14a-carboxylate (14.36 mg) was reacted under similar condition. Materials from these two reactions were combined and purified by reverse phase HPLC (acetonitrile/water (0.1% TFA)=30/70 to 100/0, 15 min) to provide the title compound (2S,6S,13aS,14aR,16aS)-ethyl 6-(tert-butoxycarbonylamino)-12,12-difluoro-2-hydroxy-5,16-dioxooctadecahydrocyclopropa[e]pyrrolo[1,2-a][1,4]diazacyclopentadecine-14a-carboxylate (91.3 mg) MS (ESI): m/z=532.2 [M+H].

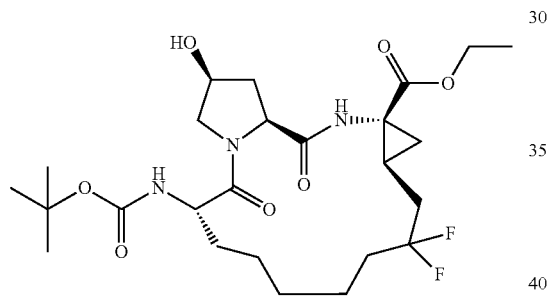

Example 1f (2R,6S,13aS,14aR,16aS)-ethyl 6-(tert-butoxycarbonylamino)-12,12-difluoro-5,16-dioxo-2-(quinoxalin-2-yloxy)octadecahydrocyclopropa[e]pyrrolo[1,2-a][1,4]diazacyclopentadecine-14a-carboxylate

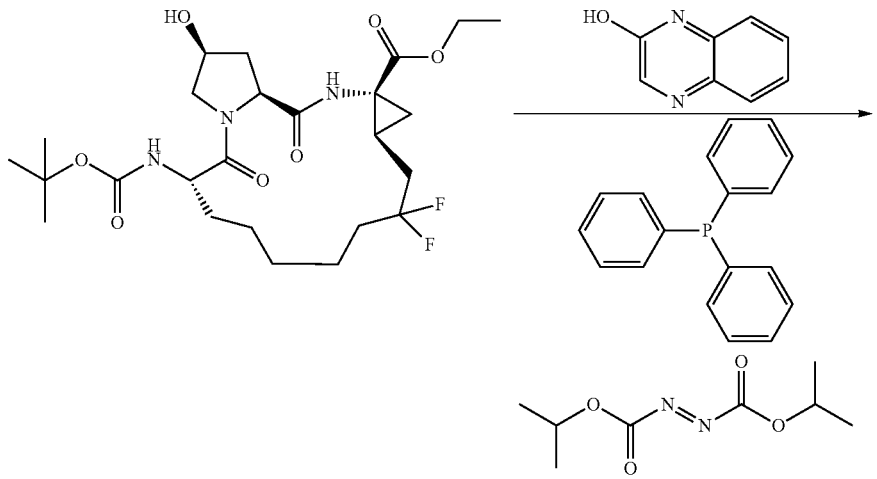

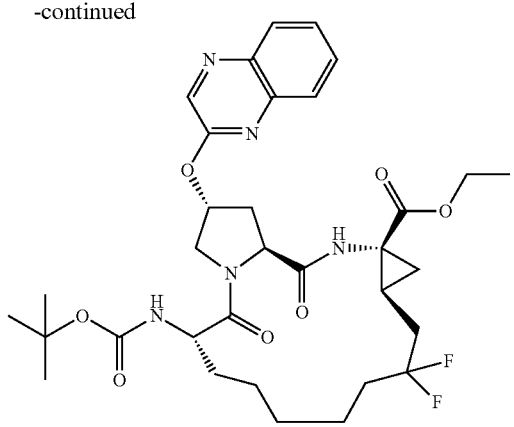

To (2S,6S,13aS,14aR,16aS)-ethyl 6-(tert-butoxycarbonylamino)-12,12-difluoro-2-hydroxy-5,16-dioxooctadecahydrocyclopropa[e]pyrrolo[1,2-a][1,4]diazacyclopentadecine-14a-carboxylate (Example 1e, 19 mg, 0.036 mmol) was added 2-hydroxyquinoxaline (8.06 mg, 0.055 mmol) followed by tetrahydrofuran (357 µl). Triphenylphosphine (15.23 mg, 0.058 mmol) was added and the solution was cooled to 0° C. DIAD (10.5 µl, 0.054 mmol) was added dropwise and the mixture was stirred at 0° C. for 15 min and at room temperature for 20 hr. The reaction mixture was diluted with dichloromethane and filtered through Celite. The solvent was evaporated under reduced pressure and the residue was purified by prep-TLC (dichloromethane/ethyl acetate=3/2, 2×) to provide the title compound (2R,6S,13aS,14aR,16aS)-ethyl 6-(tert-butoxycarbonylamino)-12,12-difluoro-5,16-dioxo-2-(quinoxalin-2-yloxy)octadecahydrocyclopropa[e]pyrrolo [1,2-a][1,4]diazacyclopentadecine-14a-carboxylate (14.6 mg, 61.8% yield).

Example 1g (2R,6S,13aS,14aR,16aS)-6-(tert-butoxycarbonylamino)-12,12-difluoro-5,16-dioxo-2-(quinoxalin-2-yloxy)octadecahydrocyclopropa[e]pyrrolo[1,2-a][1,4]diazacyclopentadecine-14a-carboxylic acid

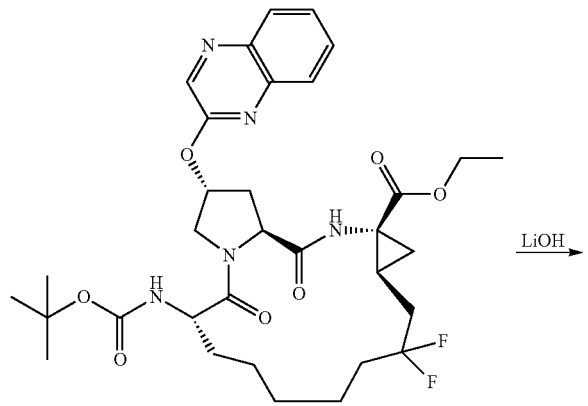

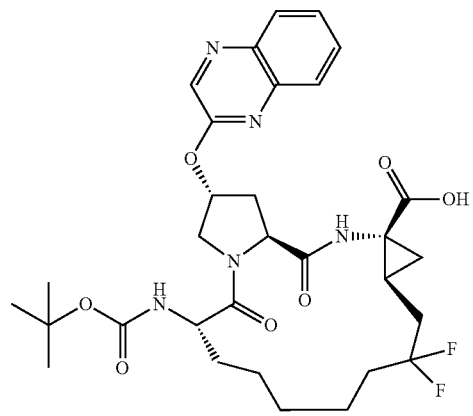

To a solution of (2R,6S,13aS,14aR,16aS)-ethyl 6-(tert-butoxycarbonylamino)-12,12-difluoro-5,16-dioxo-2-(quinoxalin-2-yloxy)octadecahydrocyclopropa[e]pyrrolo [1,2-a][1,4] diazacyclopentadecine-14a-carboxylate (Example 1h, 14.6 mg, 0.022 mmol) in tetrahydrofuran (55.3 µl), ethanol (27.6 µl) and Water (27.6 µl) was added lithium hydroxide monohydrate (4.19 mg, 0.100 mmol). The reaction mixture was stirred at room temperature overnight, diluted with ethyl acetate and cooled to 0° C. The reaction mixture was neutralized with HCl (4 N in dioxane, 25 µl; diluted with ethyl acetate), stirred at room temperature and dried over anhydrous sodium sulfate. The mixture was filtered and evaporated under reduced pressure and the residue was purified by prep-TLC (elute with dichloromethane/methanol=5/1) to provide the title compound (2R,6S,13aS,14aR,16aS)-6-(tert-butoxycarbonylamino)-12,12-difluoro-5,16-dioxo-2-(quinoxalin-2-yloxy)octadecahydrocyclopropa[e]pyrrolo[1,2-a][1,4]diazacyclopentadecine-14a-carboxylic acid (11.04 mg, 0.017 mmol, 79% yield).

Example 1 tert-butyl(2R,6S,13aS,14aR,16aS)-14a-(cyclopropyl-
sulfonylcarbamoyl)-12,12-difluoro-5,16-dioxo-2-
(quinoxalin-2-yloxy)octadecahydrocyclopropa[e]
pyrrolo[1,2-a][1,4]diazacyclopentadecin-6-
ylcarbamate

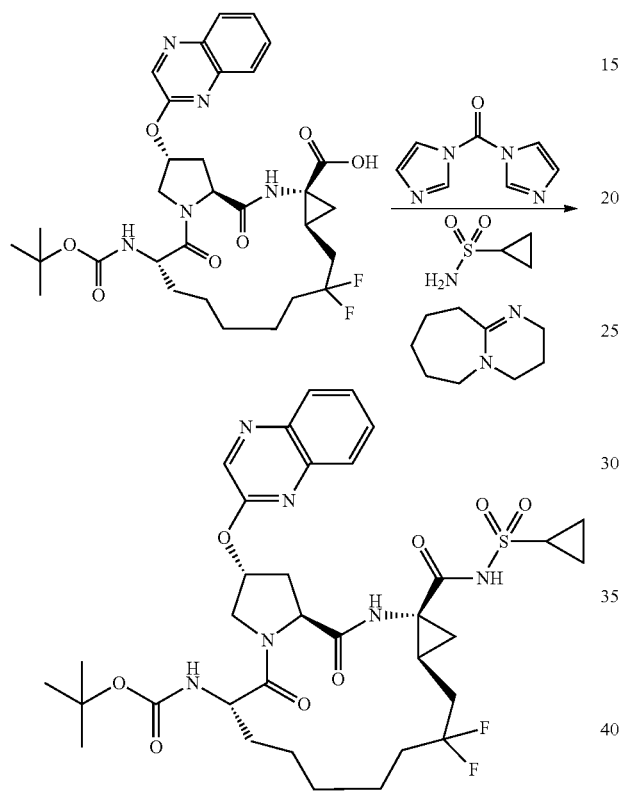

To a solution of (2R,6S,13aS,14aR,16aS)-6-(tert-butoxycarbonylamino)-12,12-difluoro-5,16-dioxo-2-(quinoxalin-2-yloxy)octadecahydrocyclopropa[e]pyrrolo[1,2-a][1,4]diazacyclopenta decine-14a-carboxylic acid (Example 1g, 11.0 mg, 0.017 mmol) in dichloroethane (175 µl) was added molecular sieves (3 Å) and carbonyl diimidazole (4.65 mg, 0.029 mmol). The reaction mixture was stirred at 40° C. for 1.5 hr and cooled to room temperature. Cyclopropanesulfonamide (4.24 mg, 0.035 mmol) was added followed by DBU (5.5 µl, 0.036 mmol). The mixture was stirred at room temperature for 2 hr, diluted with dichloromethane, cooled to 0° C., and neutralized with HCl (23.5 µl of 4 N in dioxane and diluted with ethyl acetate). The mixture was filtered to remove sieves and the filtrate was concentrated under reduced pressure. The residue was purified by prep-TLC (dichloromethane/methanol=20/1) to give a white solid (12 mg, 100% yield). This material was repurified by prep-TLC (dichloromethane/ethyl acetate/methanol=1/1/0.02) to provide the title compound tert-butyl (2R,6S,13aS,14aR,16aS)-14a-(cyclopropylsulfonylcarbamoyl)-12,12-difluoro-5,16-dioxo-2-(quinoxalin-2-yloxy)octadecahydrocyclopropa[e]pyrrolo[1,2-a][1,4]diazacyclopentadecin-6-ylcarbamate (10.3 mg, 0.014 mmol, 80% yield) MS (ESI): m/z=735.4 [M+H].

Example 1 provided an $IC_{50}$ of >1.0 nM in a 1a enzyme assay; an $IC_{50}$ of >1.0 nM in a 1b enzyme assay; and a HLM stability value of between 50-100 µl/min/mg.

Example 2

N-((2R,6S,13aS,14aR,16aS)-14a-(cyclopropylsulfonylcarbamoyl)-12,12-difluoro-5,16-dioxo-2-(quinoxalin-2-yloxy)octadecahydrocyclopropa[e]pyrrolo[1,2-a][1,4]diazacyclopentadecin-6-yl)-5-methylisoxazole-3-carboxamide

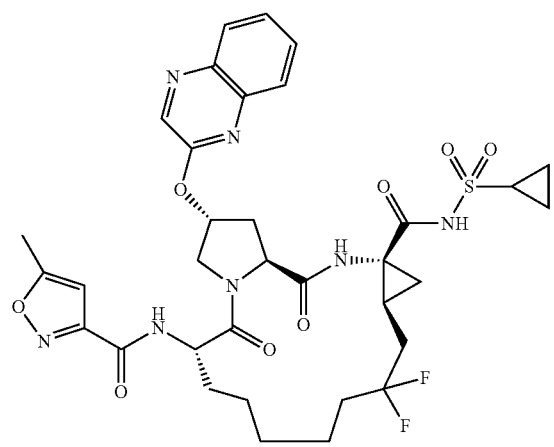 [SMILES: Cc1cc(C(=O)N[C@H]2CCCCCC(F)(F)C[C@@H]3C[C@@]3(C(=O)NS(=O)(=O)C3CC3)NC(=O)[C@@H]3C[C@@H](Oc4cnc5ccccc5n4)CN3C2=O)no1]

Example 2a (2R,6S,13aS,14aR,16aS)-6-amino-N-(cyclopropylsulfonyl)-12,12-difluoro-5,16-dioxo-2-(quinoxalin-2-yloxy)octadecahydrocyclopropa[e]pyrrolo[1,2-a][1,4]diazacyclopenta decine-14a-carboxamide

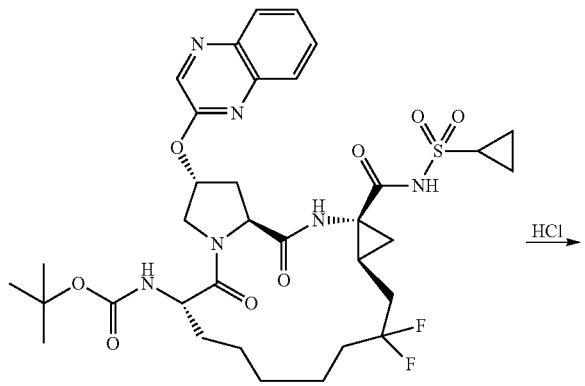

51
-continued

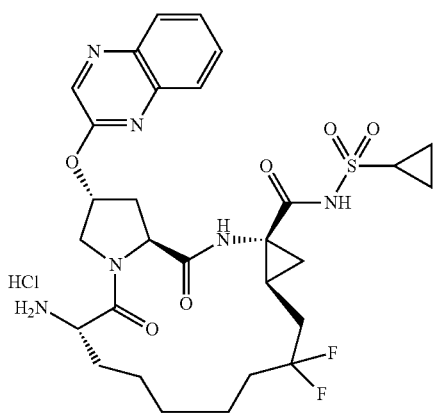

To tert-butyl (2R,6S,13aS,14aR,16aS)-14a-(cyclopropyl-sulfonylcarbamoyl)-12,12-difluoro-5,16-dioxo-2-(quinoxa-lin-2-yloxy)octadecahydrocyclopropa[e]pyrrolo[1,2-a][1,4]

52 diazacyclopentadecin-6-ylcarbamate (Example 1, 8.81 mg, 0.012 mmol) was added ethyl acetate (60 µl) followed by HCl (4 N in dioxane, 60 µl, 0.240 mmol). The solution was stirred at room temperature for 4 hr (a solid appeared), and LC/MS showed completion. The reaction mixture was concentrated to give the title compound (2R,6S,13aS,14aR,16aS)-6-amino-N-(cyclopropylsulfonyl)-12,12-difluoro-5,16-dioxo-2-(quinoxalin-2-yloxy)octadecahydrocyclo propa[e]pyrrolo[1,2-a][1,4]diazacyclopentadecine-14a-carboxamide, hydrochloric acid (8.05 mg, quantitative yield).

Example 2

N-((2R,6S,13aS,14aR,16aS)-14a-(cyclopropylsulfo-nylcarbamoyl)-12,12-difluoro-5,16-dioxo-2-(qui-noxalin-2-yloxy)octadecahydrocyclopropa[e]pyrrolo[1,2-a][1,4]diazacyclopentadecin-6-yl)-5-methylisoxazole-3-carboxamide

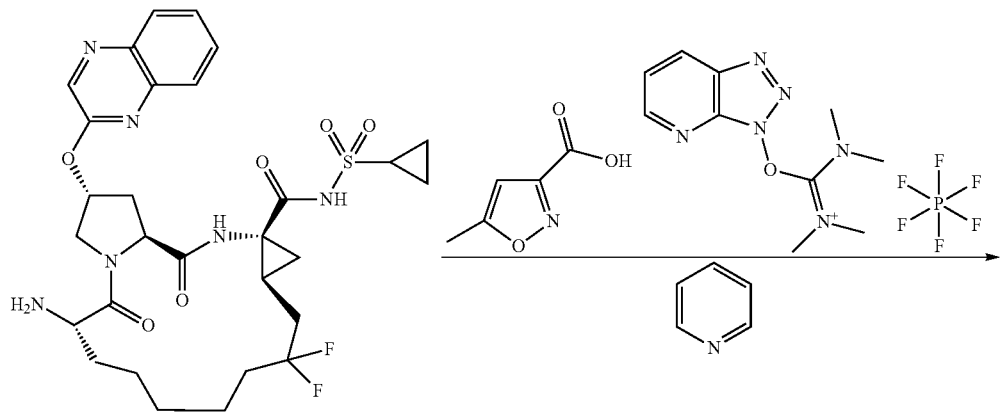

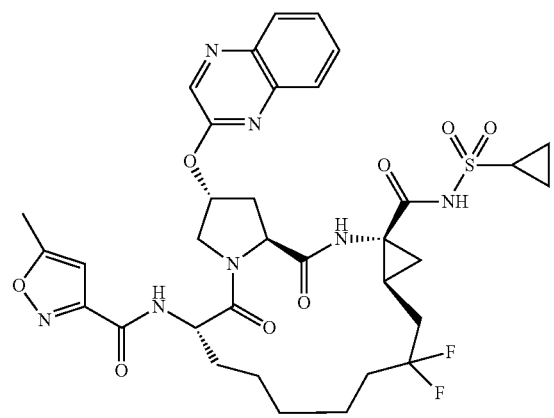

To a solution of (2R,6S,13aS,14aR,16aS)-6-amino-N-(cyclopropylsulfonyl)-12,12-difluoro-5,16-dioxo-2-(quinoxalin-2-yloxy)octadecahydrocyclopropa[e]pyrrolo[1,2-a][1,4]diazacyclopentadecine-14a-carboxamide, Hydrochloric Acid (Example 2a, 8.05 mg, 0.012 mmol) in DMF (120 μl) was added pyridine (7 μl, 0.087 mmol) followed by 5-methylisoxazole-3-carboxylic acid (2.28 mg, 0.018 mmol) and then HATU (7.04 mg, 0.019 mmol). The reaction mixture was stirred at room temperature overnight, diluted with ethyl acetate, cooled to 0° C. and neutralized with HCl (4 N in dioxane, 22 μl; diluted with ethyl acetate). The mixture was concentrated and purified by prep-TLC (ethyl acetate) to provide the title compound N-((2R,6S,13aS,14aR,16aS)-14a-(cyclopropylsulfonylcarbamoyl)-12,12-difluoro-5,16-dioxo-2-(quinoxalin-2-yloxy)octadecahydrocyclopropa[e]pyrrolo[1,2-a][1,4]diazacyclopentadecin-6-yl)-5-methylisoxazole-3-carboxamide (7.65 mg, 10.29 μmol, 86% yield) MS (ESI): m/z=744.3 [M+H].

Example 2 provided an $IC_{50}$ of >1.0 nM in a 1a enzyme assay; an $IC_{50}$ of >1.0 nM in a 1b enzyme assay; a HLM stability value of <50 μl/min/mg; an $EC_{50}$ of >5.0 nM in a replicon cell line assay in a 1a-H77 background, and an $EC_{50}$ of >5.0 nM in a replicon cell line assay in a 1b-con1 background.

Example 3

Tert-butyl(2R,6S,13aS,14aR,16aS)-14a-(cyclopropylsulfonylcarbamoyl)-12,12-difluoro-2-(3-methylquinoxalin-2-yloxy)-5,16-dioxooctadecahydrocyclopropa[e]pyrrolo[1,2-a][1,4]diazacyclopentadecin-6-ylcarbamate

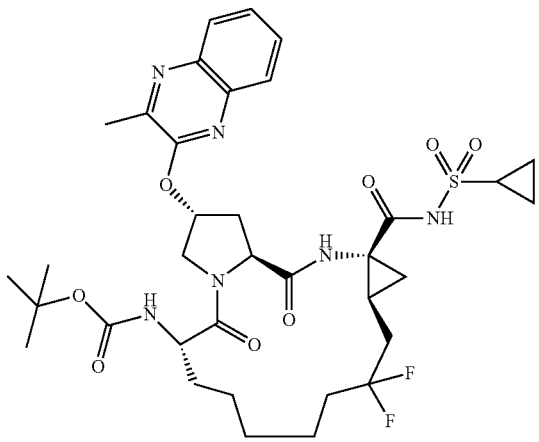 [SMILES: Cc1nc2ccccc2nc1O[C@@H]1C[C@H]2C(=O)N[C@]3(C(=O)NS(=O)(=O)C4CC4)C[C@H]3CC(F)(F)CCCCC[C@H](NC(=O)OC(C)(C)C)C(=O)N2C1]

Example 3a (2R,6S,13aS,14aR,16aS)-ethyl 6-(tert-butoxycarbonylamino)-12,12-difluoro-2-(3-methylquinoxalin-2-yloxy)-5,16-dioxooctadecahydrocyclopropa[e]pyrrolo[1,2-a][1,4]diazacyclopentadecine-14a-carboxylate

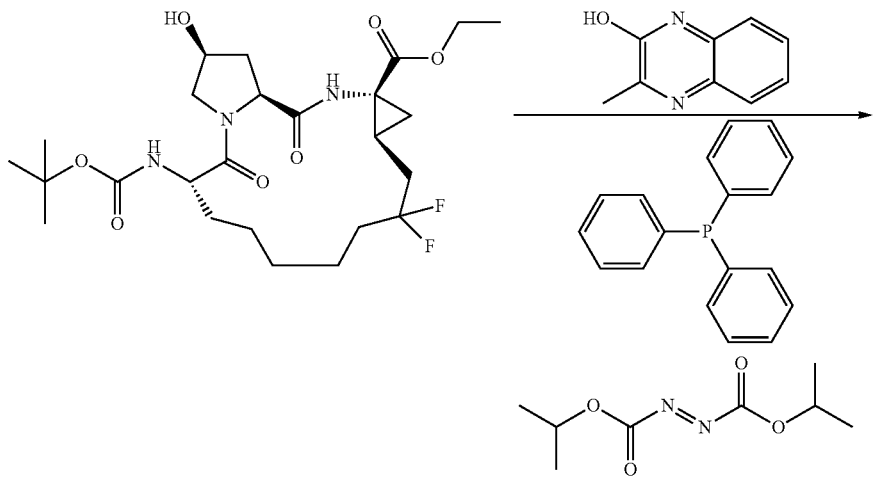

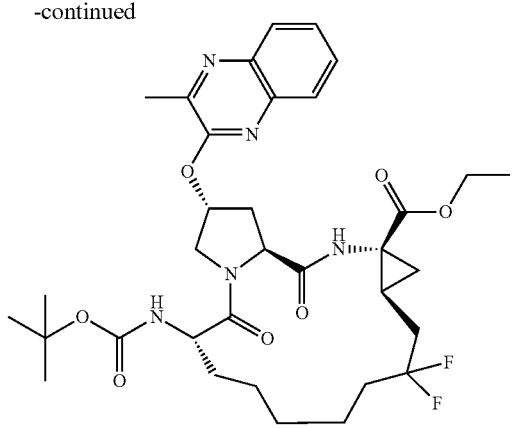

Example 3a was prepared according to the procedure utilized for the preparation of Example 1f, replacing 2-quinoxalinol with 3-methyl-2-quinoxalinol.

Example 3b (2R,6S,13aS,14aR,16aS)-6-(tert-butoxycarbonylamino)-12,12-difluoro-2-(3-methylquinoxalin-2-yloxy)-5,16-dioxooctadecahydrocyclopropa[e]pyrrolo[1,2-a][1,4]diazacyclopentadecine-14a-carboxylic acid Example 3b was prepared according to the procedure utilized for the preparation of Example 1 g, replacing the product of Example 1f with the product of Example 3a.

Example 3 tert-butyl (2R,6S,13aS,14aR,16aS)-14a-(cyclopropylsulfonylcarbamoyl)-12,12-difluoro-2-(3-methylquinoxalin-2-yloxy)-5,16-dioxooctadecahydrocyclopropa[e]pyrrolo[1,2-a][1,4]diazacyclopentadecin-6-ylcarbamate

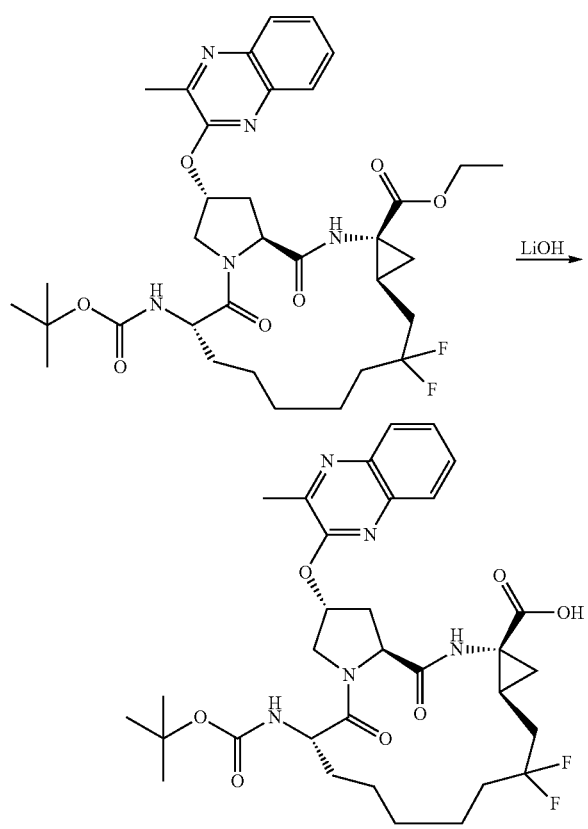

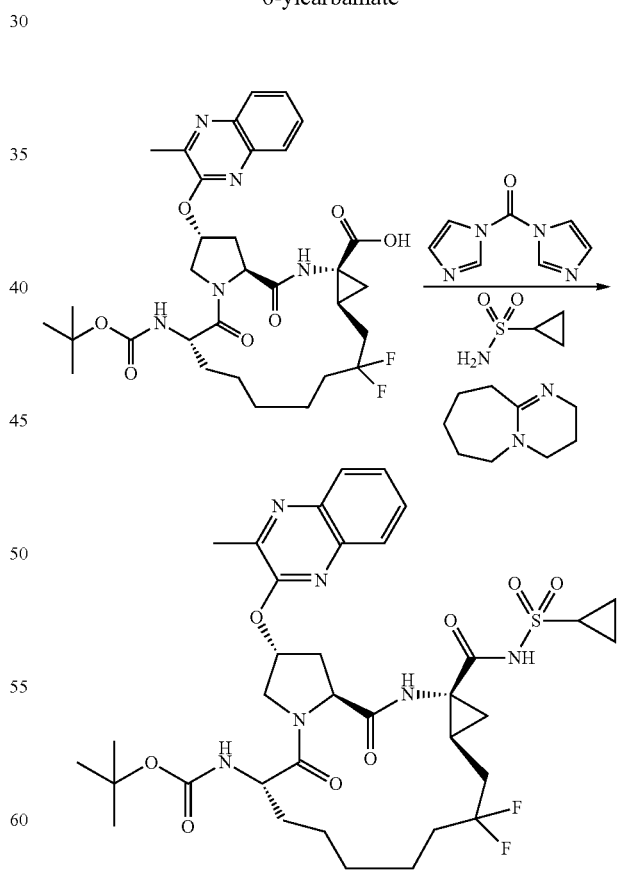

Example 3 was prepared according to the procedure utilized for the preparation of Example 1, replacing the product of Example 1 g with the product of Example 3b. MS (ESI): m/z=749.3 [M+H].

Example 3 provided an IC$_{50}$ of between 0.1 and 0.5 nM in a 1a enzyme assay; and an IC$_{50}$ of between 0.1 and 0.5 nM in a 1b enzyme assay.

Example 4

N-((2R,6S,13aS,14aR,16aS)-14a-(cyclopropylsulfonylcarbamoyl)-12,12-difluoro-2-(3-methylquinoxalin-2-yloxy)-5,16-dioxooctadecahydrocyclopropa[e]pyrrolo[1,2-a][1,4]diazacyclopentadecin-6-yl)-5-methylisoxazole-3-carboxamide

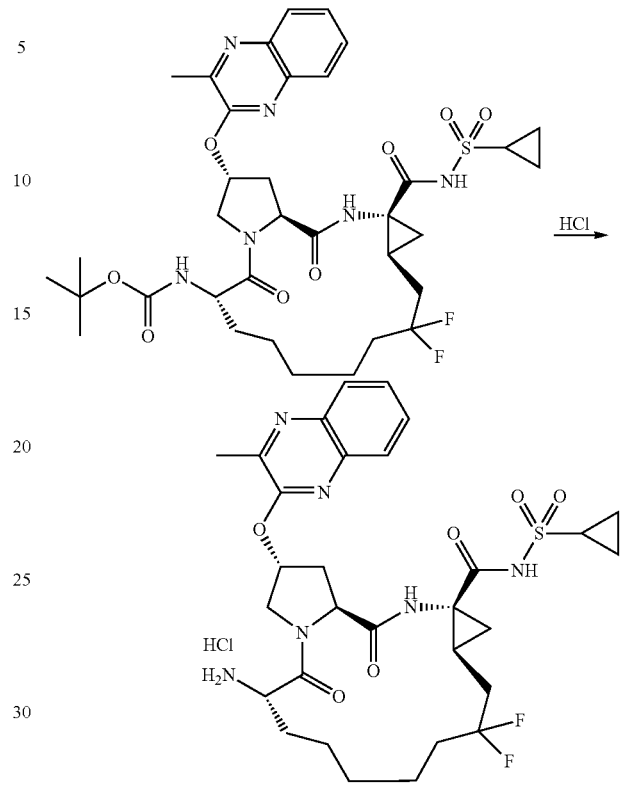

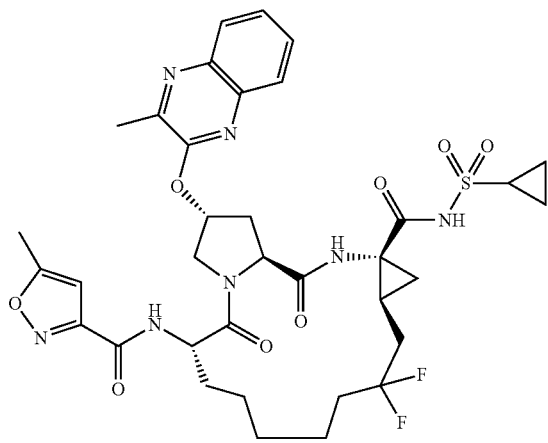 [SMILES: Cc1cc(C(=O)N[C@H]2CCCCCC(F)(F)C[C@@H]3C[C@@]3(C(=O)NS(=O)(=O)C3CC3)NC(=O)[C@@H]3C[C@@H](Oc4nc5ccccc5nc4C)CN3C2=O)no1]

Example 4a (2R,6S,13aS,14aR,16aS)-6-amino-N-(cyclopropylsulfonyl)-12,12-difluoro-2-(3-methylquinoxalin-2-yloxy)-5,16-dioxooctadecahydrocyclopropa[e]pyrrolo[1,2-a][1,4]diazacyclopentadecine-14a-carboxamide hydrochloride Example 4a was prepared according to the procedure utilized for the preparation of Example 2a, replacing the product of Example 1 with the product of Example 3.

Example 4

N-((2R,6S,13aS,14aR,16aS)-14a-(cyclopropylsulfonylcarbamoyl)-12,12-difluoro-2-(3-methylquinoxalin-2-yloxy)-5,16-dioxooctadecahydrocyclopropa[e]pyrrolo[1,2-a][1,4]diazacyclopentadecin-6-yl)-5-methylisoxazole-3-carboxamide

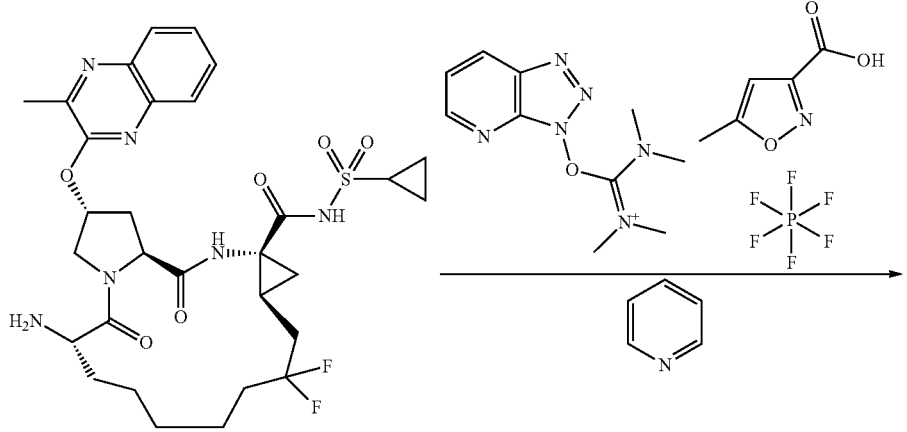

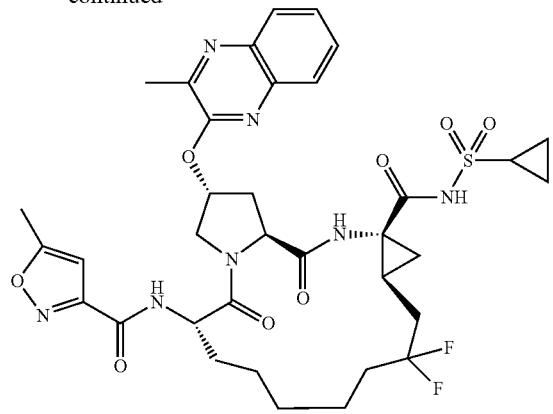

Example 4 was prepared according to the procedure utilized for the preparation of Example 2, replacing the product of Example 2a with the product of Example 4a. MS (ESI): m/z=758.3 [M+H].

Example 4 provided an $IC_{50}$ of between 0.1 and 0.5 nM in a 1a enzyme assay; an $IC_{50}$ of between 0.5 and 1.0 nM in a 1b enzyme assay; a HLM stability value of <50 μl/min/mg; an $EC_{50}$ of >5.0 nM in a replicon cell line assay in a 1a-H77 background, and an $EC_{50}$ of between 1.0 and 2.0 nM in a replicon cell line assay in a 1b-con1 background.

Example 5 tert-butyl (2R,6S,13aS,14aR,16aS)-14a-(cyclopropylsulfonylcarbamoyl)-12,12-difluoro-5,16-dioxo-2-(3-phenylquinoxalin-2-yloxy)octadecahydrocyclopropa[e]pyrrolo[1,2-a][1,4]diazacyclopentadecin-6-ylcarbamate

Example 5a (2R,6S,13aS,14aR,16aS)-ethyl 6-(tert-butoxycarbonylamino)-12,12-difluo-5,16-dioxo-2-(3-phenylquinoxalin-2-yloxy)octadecahydrocyclopropa[e]pyrrolo[1,2-a][1,4]diazacyclopentadecine-14a-carboxylate

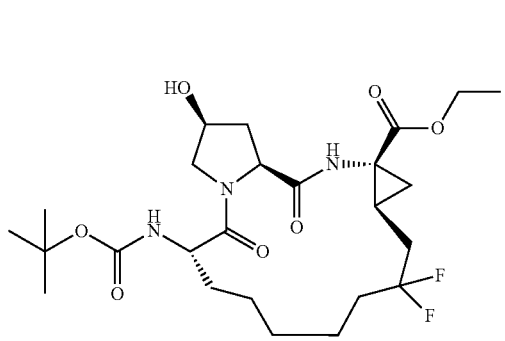
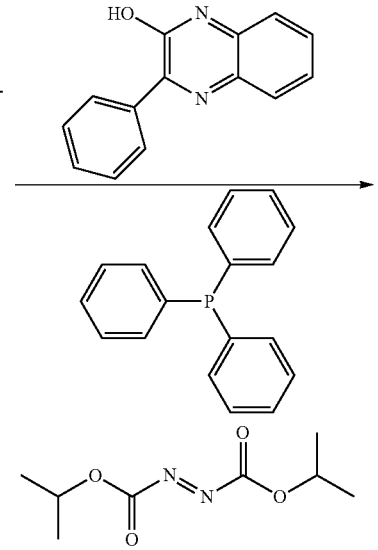

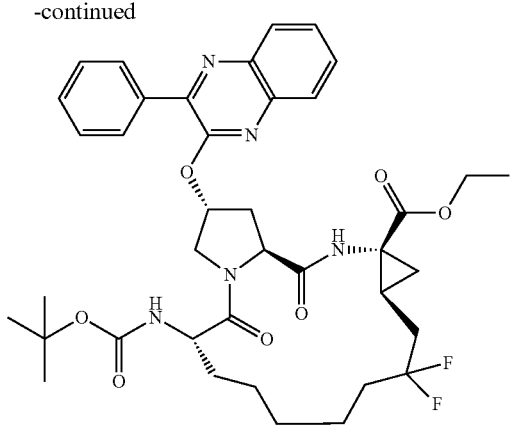

Example 5a was prepared according to the procedure utilized for the preparation of Example 1f, replacing 2-quinoxalinol with 3-phenyl-2-quinoxalinol.

Example 5b was prepared according to the procedure utilized for the preparation of Example 1g, replacing the product of Example 1f with the product of Example 5a.

Example 5b (2R,6S,13aS,14aR,16aS)-6-(tert-butoxycarbonylamino)-12,12-difluoro-5,16-dioxo-2-(3-phenylquinoxalin-2-yloxy)octadecahydrocyclopropa[e]pyrrolo[1,2-a][1,4]diazacyclopentadecine-14a-carboxylic acid Example 5 tert-butyl (2R,6S,13aS,14aR,16aS)-14a-(cyclopropylsulfonylcarbamoyl)-12,12-difluoro-5,16-dioxo-2-(3-phenylquinoxalin-2-yloxy)octadecahydrocyclopropa[e]pyrrolo[1,2-a][1,4]diazacyclopentadecin-6-ylcarbamate

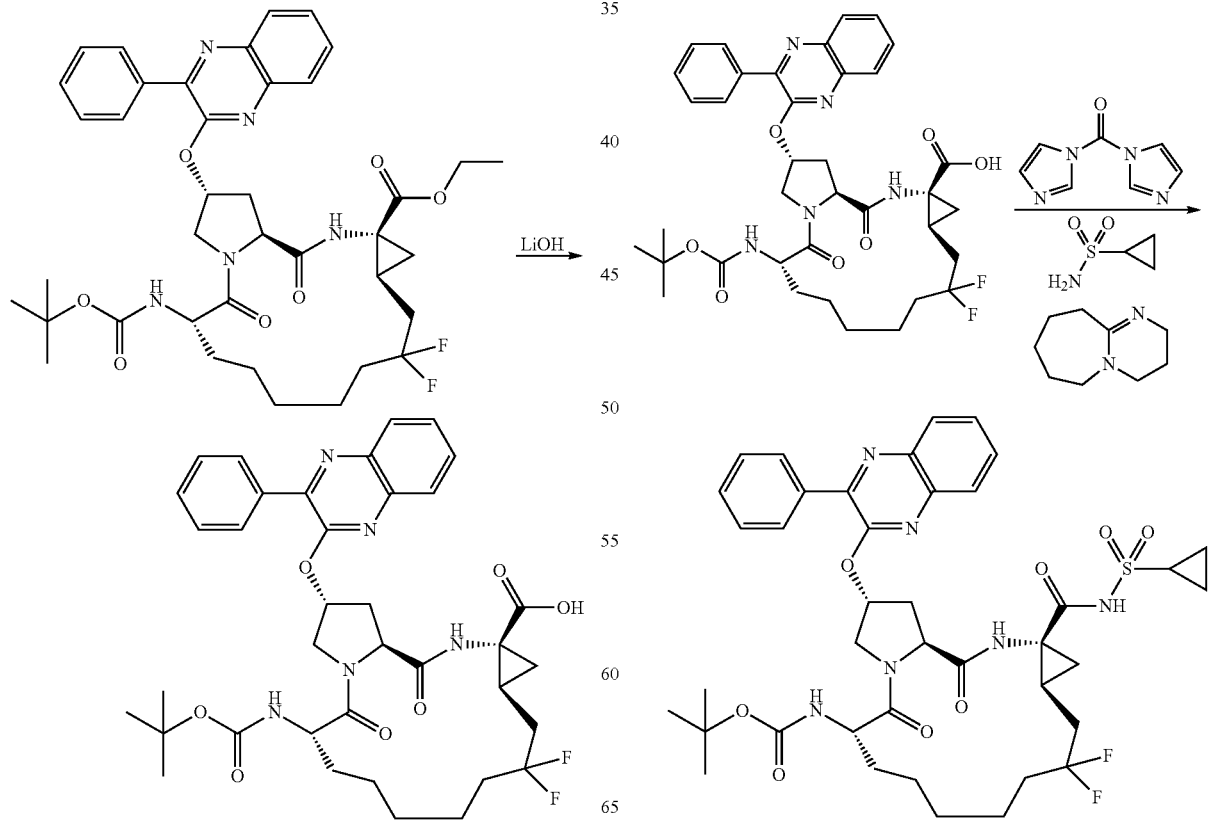

Example 5 provided an IC$_{50}$ of between 0.5 and 1.0 nM in a 1a enzyme assay; and an IC$_{50}$ of between 0.5 and 1.0 nM in a 1b enzyme assay.

Example 6

N-((2R,6S,13aS,14aR,16aS)-14a-(cyclopropylsulfonylcarbamoyl)-12,12-difluoro-5,16-dioxo-2-(3-phenylquinoxalin-2-yloxy)octadecahydrocyclopropa[e]pyrrolo[1,2-a][1,4]diazacyclopentadecin-6-yl)-5-methylisoxazole-3-carboxamide

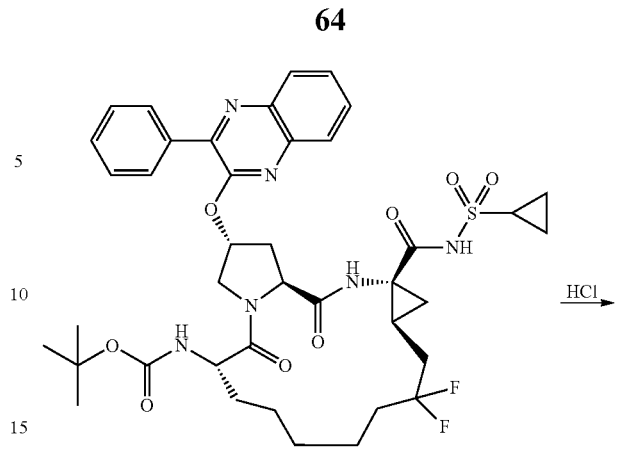

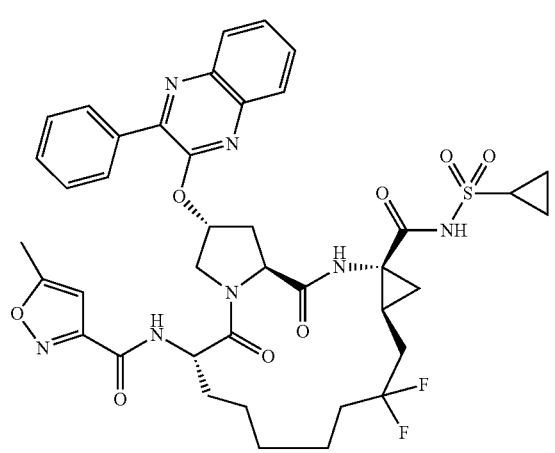 [SMILES: Cc1cc(C(=O)N[C@H]2CCCCCC(F)(F)C[C@@H]3C[C@@]3(C(=O)NS(=O)(=O)C3CC3)NC(=O)[C@@H]3C[C@@H](Oc4nc5ccccc5nc4-c4ccccc4)CN3C2=O)no1]

Example 6a (2R,6S,13aS,14aR,16aS)-6-amino-N-(cyclopropylsulfonyl)-12,12-difluoro-5,16-dioxo-2-(3-phenylquinoxalin-2-yloxy)octadecahydrocyclopropa[e]pyrrolo[1,2-a][1,4]diazacyclopentadecine-14a-carboxamide

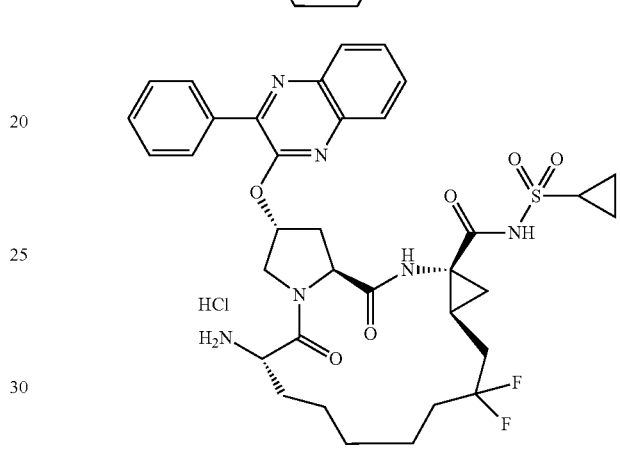

Example 6a was prepared according to the procedure utilized for the preparation of Example 2a, replacing the product of Example 1 with the product of Example 5.

Example 6

N-((2R,6S,13aS,14aR,16aS)-14a-(cyclopropylsulfonylcarbamoyl)-12,12-difluoro-5,16-dioxo-2-(3-phenylquinoxalin-2-yloxy)octadecahydrocyclopropa[e]pyrrolo[1,2-a][1,4]diazacyclopentadecin-6-yl)-5-methylisoxazole-3-carboxamide

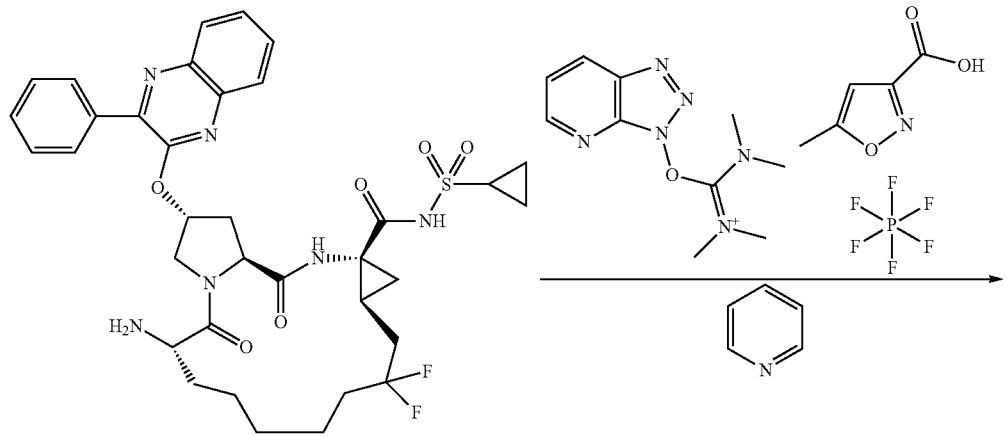

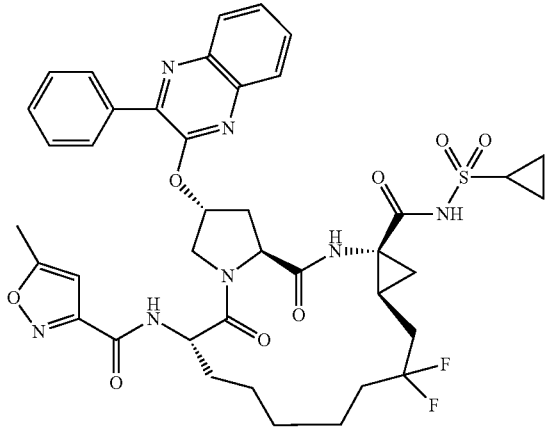

Example 6 was prepared according to the procedure utilized for the preparation of Example 2, replacing the product of Example 2a with the product of Example 6a. MS (ESI): m/z=820.3 [M+H].

Example 6 provided an $IC_{50}$ of <0.1 nM in a 1a enzyme assay; an $IC_{50}$ of between 0.1 and 0.5 nM in a 1b enzyme assay; a HLM stability value of <50 μl/min/mg; an $EC_{50}$ of between 2.0 and 5.0 nM in a replicon cell line assay in a 1a-H77 background, and an $EC_{50}$ of between 1.0 and 2.0 nM in a replicon cell line assay in a 1-con1 background.

Example 7 tert-butyl (2R,6S,13aS,14aR,16aS)-14a-(cyclopropylsulfonyl-2-yloxy)-12,12-difluoro-5,16-dioxooctadecahydrocyclopropa[e]pyrrolo[1,2-a][1,4]diazacyclopentadecin-6-yl-carbamate

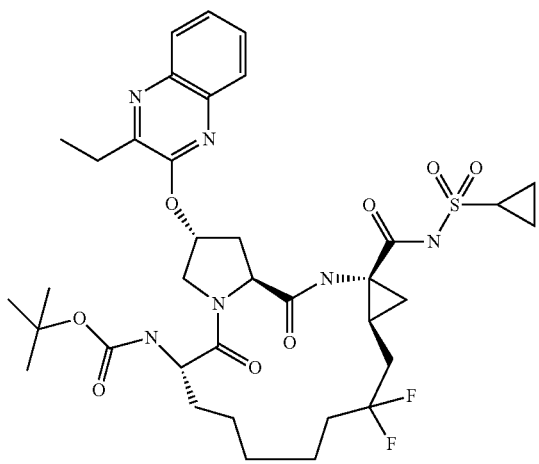 [SMILES: CCc1nc2ccccc2nc1O[C@@H]1C[C@H]2C(=O)N[C@]3(C(=O)NS(=O)(=O)C4CC4)C[C@H]3CC(F)(F)CCCCC[C@H](NC(=O)OC(C)(C)C)C(=O)N2C1]

Example 7a (1R,2S)-ethyl 1-(bis(tert-butoxycarbonyl)amino)-2-(2-hydroxyethyl)cyclopropane carboxylate

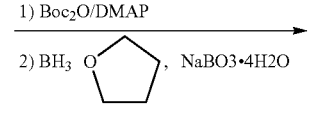

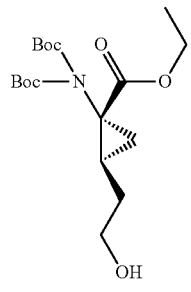

Example 7a

To (1R,2S)-ethyl 1-(tert-butoxycarbonylamino)-2-vinylcyclopropanecarboxylate (10 g, 39.2 mmol) and Boc anhydride (22.73 mL, 98 mmol) dissolved in tetrahydrofuran (25 mL) at room temperature was added portionwise DMAP (3.83 g, 31.3 mmol) and the mixture was stirred for 3 h. The mixture was quenched with water and extracted with ethyl acetate. The organic layer was washed with 0.1 N HCl followed by saturated aqueous sodium chloride solution, separated, dried over anhydrous magnesium sulfate, filtered, and evaporated under reduced pressure. The residual oil was purified by flash chromatography on silica gel eluting with a 5-15% ethyl acetate/hexane gradient to provide (1R,2S)-ethyl 1-(bis(tert-butoxycarbonyl)amino)-2-vinylcyclopropanecarboxylate (13.2 g, 37.1 mmol, 95% yield) as a clear oil. MS (ESI): m/z=378.0 [M+Na].

To a solution of (1R,2S)-ethyl 1-(bis(tert-butoxycarbonyl)amino)-2-vinylcyclopropane carboxylate (13.2 g, 37.1 mmol) in tetrahydrofuran (50 mL) at -15° C. was added dropwise 1 N borane tetrahydrofuran complex (74.3 mL, 74.3 mmol) and the mixture was stirred for 2 h at −15° C. To the resulting mixture stirring at 0° C. was added dropwise water (100 mL) followed by sodium perborate tetrahydrate (11.43 g, 74.3 mmol), and the mixture was stirred for 16 hr at rt. The reaction mixture was diluted with ethyl acetate and water, and the resulting organic layer was washed with saturated aqueous sodium chloride solution, separated, dried over anhydrous magnesium sulfate, filtered, and the solvent evaporated under reduced pressure. The residue was purified via flash chromatography on silica gel (10-20% acetone/hex). The resulting impure material was repurified by flash chromatography on silica gel (eluting with a 25%-50% ethyl acetate/hexane gradient) to give (1R,2S)-ethyl 1-(bis(tert-butoxycarbonyl)amino)-2-(2-hydroxyethyl)cyclopropanecarboxylate (9.15 g, 24.50 mmol, 66.0% yield) as an oil. MS (ESI): m/z=396.0 [M+Na].

Example 7b (1R,2S)-ethyl 1-(bis(tert-butoxycarbonyl)amino)-2-(2-hydroxyhex-5-enyl)cyclopropanecarboxylate

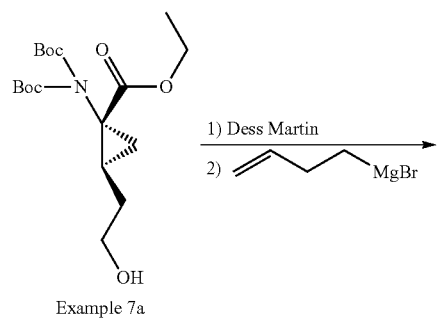

Example 7a

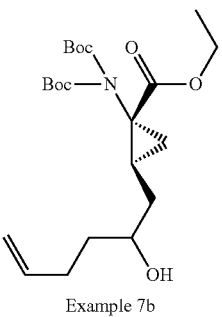

Example 7b

To a solution of (1R,2S)-ethyl 1-(bis(tert-butoxycarbonyl)amino)-2-(2-hydroxyethyl)cyclopropanecarboxylate (8.65 g, 23.2 mmol) in dichloromethane (116 ml) at 25° C. was added Dess-Martin Periodinane (13.8 g, 32.4 mmol). The mixture was stirred for 3 h and quenched with 1 N sodium thiosulfate (70 mL) and aqueous saturated sodium bicarbonate solution (30 mL), and stirred for 1 h. The organic layer was separated, dried over anhydrous sodium sulfate, filtered, and evaporated under reduced pressure. This material was purified by flash chromatography on silica gel (eluted with 25% ethyl acetate/hexane) to yield (1R,2S)-ethyl 1-(bis(tert-butoxycarbonyl)amino)-2-(2-oxoethyl)cyclopropanecarboxylate (7.05 g, 82% yield) as an oil. MS (ESI): m/z=394.1 [M+Na].
To (1R,2S)-ethyl 1-(bis(tert-butoxycarbonyl)amino)-2-(2-oxoethyl)cyclopropanecarboxylate (7.05 g, 19.0 mmol) in tetrahydrofuran (60 mL) at −78° C. was added but-3-enyl-magnesium bromide (45.6 mL, 22.78 mmol) and the reaction mixture was stirred for 30 min. The mixture was then quenched with saturated aqueous ammonium chloride and extracted with ethyl acetate. The organic layer was separated, dried over anhydrous magnesium sulfate, filtered, and evaporated under reduced pressure. The residual oil was purified via flash chromatography on silica gel (25% hexane/ethyl acetate) to provide the title compound (2.75 g, 34%) as an oil, along with recovered starting material (2.89 g, 41%). MS (ESI): m/z=450.1 [M+Na].

Example 7c (1R,2S)-ethyl 1-(bis(tert-butoxycarbonyl)amino)-2-(2-oxohex-5-enyl)cyclopropane carboxylate

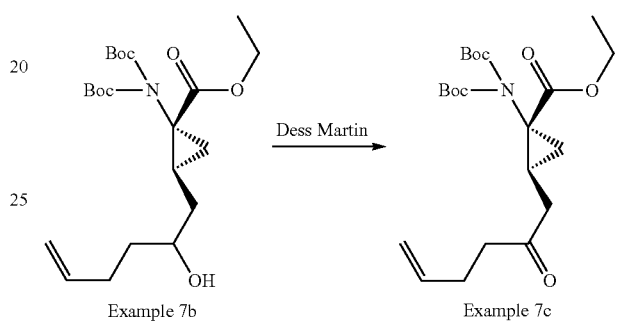

Example 7b      Example 7c

To a solution of (1R,2S)-ethyl 1-(bis(tert-butoxycarbonyl)amino)-2-(2-hydroxyhex-5-enyl)cyclopropanecarboxylate (4.3 g, 10 mmol) in dichloromethane (50 ml) at 25° C. was added Dess-Martin Periodinane (5.97 g, 14.1 mmol). The reaction mixture was stirred for 3 h and quenched with 1 N aqueous sodium thiosulfate solution (50 mL) and saturated aqueous sodium bicarbonate solution (15 mL), and the reaction mixture stirred for 1 h. The organic layer was separated, dried over anhydrous sodium sulfate, filtered, and evaporated under reduced. The crude product was purified by flash chromatography on silica gel (15% ethyl acetate/hexane) to provide (1R,2S)-ethyl 1-(bis(tert-butoxycarbonyl)amino)-2-(2-oxohex-5-enyl)cyclopropane carboxylate (3.8 g, 88% yield) as an oil. MS (ESI): m/z=448.1 [M+Na].

Example 7d (1R,2S)-ethyl 1-(bis(tert-butoxycarbonyl)amino)-2-(2,2-difluorohex-5-enyl)cyclo propanecarboxylate

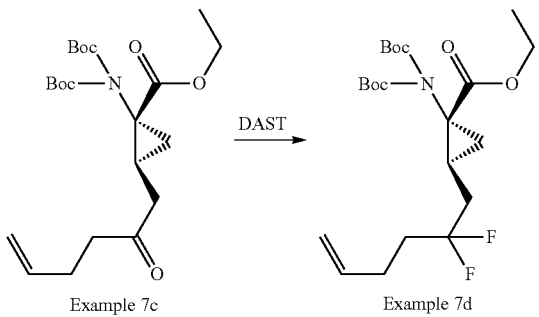

Example 7c      Example 7d

A solution of (1R,2S)-ethyl 1-(bis(tert-butoxycarbonyl)amino)-2-(2-oxohex-5-enyl)cyclopropanecarboxylate (3.78 g, 8.88 mmol) in DAST (5.87 ml, 44.4 mmol) was stirred at room temperature for 3 days The reaction mixture was cooled to −78° C., diluted with 50 mL dichloromethane and added in a stream to a 0° C. solution of saturated aqueous sodium bicarbonate solution (200 mL). The reaction mixture was stirred for 30 min and the organic layer was separated, dried over anhydrous sodium sulfate, filtered, and evaporated under reduced pressure. The crude material was purified by flash chromatography on silica gel (10-15% ethyl acetate/hexane gradient) to provide the title compound (1.95 g, 49%) as an oil. MS (ESI): m/z=470.1 [M+Na].

Example 7e (1R,2S)-ethyl 1-amino-2-(2,2-difluorohex-5-enyl)cyclopropanecarboxylate hydrochloride

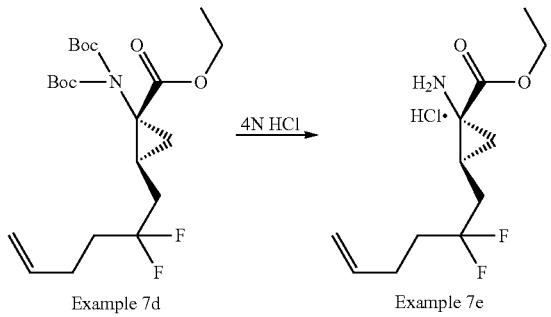

A solution of (1R,2S)-ethyl 1-(bis(tert-butoxycarbonyl)amino)-2-(2,2-difluorohex-5-enyl)cyclopropanecarboxylate (2.45 g, 5.47 mmol) in 1,4-dioxane (6 mL) and 4 N HCl (11.6 mL, 46.5 mmol) was stirred at room temperature for 3 h. The mixture was evaporated and eluted through a silica gel (50 mL) column with 4-10% methanol/dichloromethane to give (1R,2S)-ethyl 1-amino-2-(2,2-difluorohex-5-enyl)cyclopropanecarboxylate, hydrochloric acid salt (1.4 g, 4.93 mmol, 90% yield) as a yellow oil. MS (ESI): m/z=247.9 [M+H].

Example 7f (2S,4R)-1-(S)-2-(tert-butoxycarbonylamino)pent-4-enoyl)-4-hydroxypyrrolidine-2-carboxylic acid

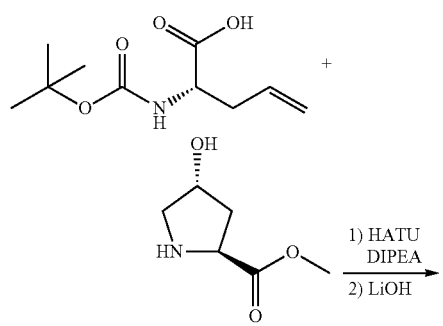

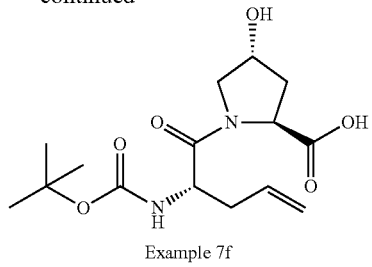

Example 7f

A mixture of (S)-2-(tert-butoxycarbonylamino)pent-4-enoic acid (3.0 g, 13.9 mmol), and 2-(3H-[1,2,3]triazolo [4,5-b]pyridin-3-yl)-1,1,3,3-tetramethylisouronium hexafluorophosphate(V) (5.83 g, 15.3 mmol) in DMF (15 ml) was stirred for 5 min at room temperature. To this mixture was added (2S,4R)-methyl 4-hydroxypyrrolidine-2-carboxylate, hydrochloric acid salt (2.78 g, 15.33 mmol) followed by the dropwise addition of N-ethyl-N-isopropylpropan-2-amine (8.52 ml, 48.8 mmol), and the reaction mixture was stirred 16 h at room temperature. The mixture was diluted with ethyl acetate, washed with 1 N aqueous sodium bicarbonate solution followed by 0.1 N HCl, and the organic layer was separated, dried over anhydrous magnesium sulfate, filtered, and evaporated under reduced pressure. The oily residue after was purified by flash chromatography on silica gel (4% methanol/dichloromethane) to provide the title compound as an oil (2S,4R)-methyl 1-((S)-2-(tert-butoxycarbonylamino)pent-4-enoyl)-4-hydroxypyrrolidine-2-carboxylate (3.0 g, 8.76 mmol, 62.9% yield). MS (ESI): m/z=342.9 [M+H].

To a solution of (2S,4R)-methyl 1-((S)-2-(tert-butoxycarbonylamino)pent-4-enoyl)-4-hydroxypyrrolidine-2-carboxylate (3.0 g, 8.76 mmol) in tetrahydrofuran (29.2 ml), water (14.6 ml), and ethanol (14.6 ml) stirring at room temperature was added lithium hydroxide monohydrate (2.39 g, 57.0 mmol). The mixture was stirred for 16 h, the organic solvent was evaporated under reduced pressure, and the aqueous layer was extracted once with dichloromethane. The aqueous layer was cooled in an ice bath, acidified with 68 mL of 1N HCl, saturated with sodium chloride, and extracted with ethyl acetate. The organic layer was dried (anhydrous sodium sulfate), filtered, and evaporated to a provide the title compound as a white foam (2.83 g, 8.62 mmol, 98% yield). MS (ESI): m/z=329.0 [M+H].

Example 7g (1R,2S)-ethyl 1-((2S,4R)-1-((S)-2-(tert-butoxycarbonylamino)pent-4-enoyl)-a-hydroxypyrrolidine-2-carboxamido)-2-(2,2-difluorohex-5-enyl)cyclopropanecarboxylate

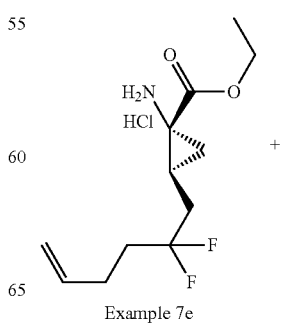

Example 7e

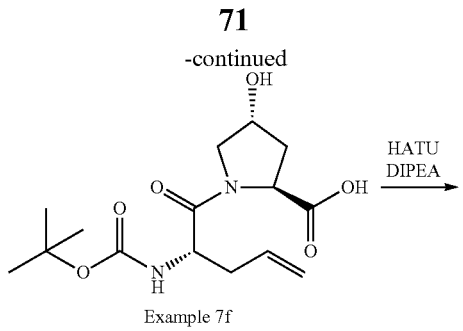

Example 7f

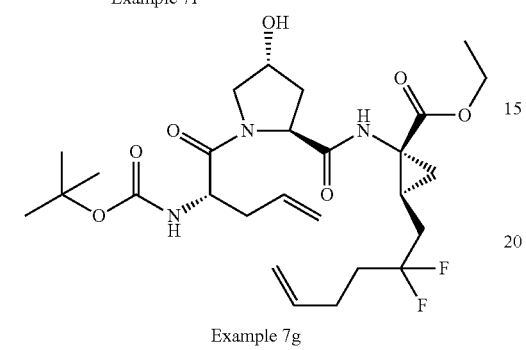

Example 7g

To a mixture of (2S,4R)-1-((S)-2-(tert-butoxycarbonylamino)pent-4-enoyl)-4-hydroxypyrrolidine-2-carboxylic acid (1.78 g, 5.43 mmol), (1R,2S)-ethyl 1-amino-2-(2,2-difluorohex-5-enyl)cyclopropanecarboxylate (1.4 g, 4.9 mmol) and 2-(3H41,2,3]triazolo[4,5-b]pyridin-3-yl)-1,1,3,3-tetramethylisouronium hexafluorophosphate(V) (2.06 g, 5.43 mmol) in dichloromethane (22 mL) was added N-ethyl-N-isopropylpropan-2-amine (3.02 mL, 17.3 mmol), and the mixture was stirred 3 h at room temperature. The reaction mixture was washed with 1 N aqueous sodium bicarbonate solution followed by 1 N HCl and organic layer was separated, dried over anhydrous sodium sulfate, filtered and evaporated under reduced pressure. The residue was purified by flash chromatography on silica gel (5% methanol/dichloromethane). Fractions containing the title compound were evaporated to a yellow oil and repurified by flash chromatography on silica gel (40% acetone/hexane) to give provide the title compound (1R,2S)-ethyl 1-((2S,4R)-14(5)-2-(tert-butoxycarbonylamino)pent-4-enoyl)-4-hydroxypyrrolidine-2-carboxamido)-2-(2,2-difluorohex-5-enyl)cyclopropanecarboxylate (2.31 g, 84% yield) as a foam. MS (ESI): m/z=558.3 [M+H].

Example 7h (2R,6S,13aS,14aR,16aS)-ethyl 6-(tert-butoxycarbonylamino)-12,12-difluoro-2-hydroxy-5,16-dioxo-1,2,3,5,6,7,10,11,12,13,13a,14,14a,15,16,16a-hexadecahydrocyclopropa[e]pyrrolo [1,2-a][1,4]diazacyclopentadecine-14a-carboxylate

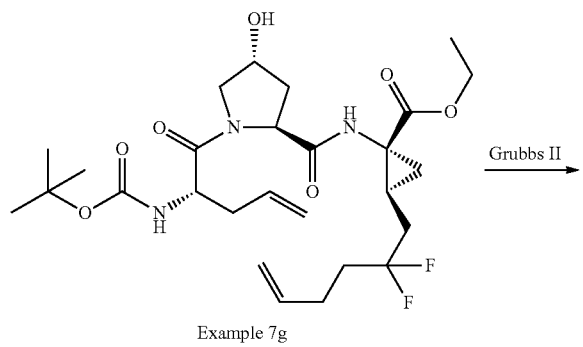

Example 7g

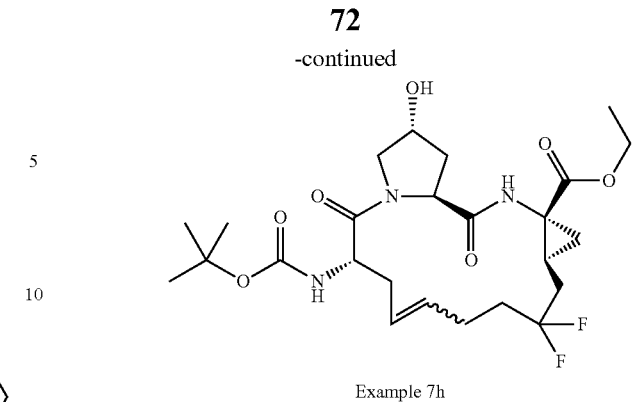

Example 7h

To a solution of(1R,2S)-ethyl 1-((2S,4R)-1-(5)-2-(tert-butoxycarbonylamino)pent-4-enoyl)-4-hydroxypyrrolidine-2-carboxamido)-2-(2,2-difluorohex-5-enyl)cyclopropanecarboxylate (1.95 g, 3.50 mmol) in dichloroethane (583 ml) which was degassed by bubbling with nitrogen for 45 min was added Grubb II catalyst (66 mg, 0.03 eq). The solution was heated at 60° C. for 2 h. Another aliquot of catalyst was added (22 mg, 0.01 eq) and the reaction mixture was heated for an additional 1.5 h. Another aliquot of catalyst (11 mg, 0.005 eq) was added and the reaction mixture was heated for an additional 1 h. The reaction mixture was quenched by the addition of 2-mercaptonicotinic acid (390 mg, 0.74 eq) and stirred at 60° C. for 45 m. The reaction mixture was cooled to 0° C. and 140 mL saturated sodium bicarbonate solution and 280 mL of water was added, and the reaction mixture was stirred for 45 min. The organic layer was separated, dried over anhydrous magnesium sulfate, filtered, and evaporated under reduced pressure. The resulting residue was purified by flash chromatography on silica gel (5% methanol/dichloromethane) to provide (2R,6S,13aS,14aR,16aS,E)-ethyl 6-(tert-butoxycarbonylamino)-12,12-difluoro-2-hydroxy-5,16-dioxo-1,2,3,5,6,7,10,11,12,13,13a,14,14a,15,16,16a-hexadecahydrocyclopropa[e]pyrrolo[1,2-a][1,4]diazacyclopentadecine-14a-carboxylate (0.94 g, 1.775 mmol, 50.8% yield) as a white solid. MS (ESI): m/z=530.2 [M+H].

Example 7i (2R,6S,13aS,14aR,16aS)-ethyl 6-(tert-butoxycarbonylamino)-12,12-difluoro-2-hydroxy-5,16-dioxooctadecahydrocyclopropa[e]pyrrolo [1,2-a][1,4]diazacyclopentadecine-14a-carboxylate

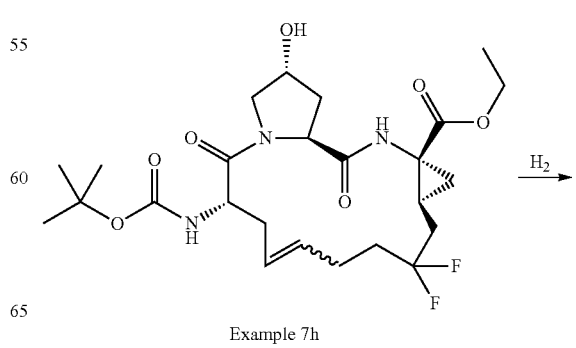

Example 7h

-continued

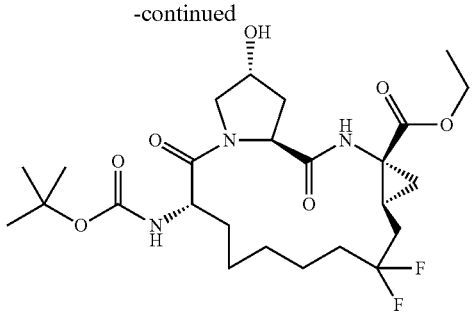

Example 7i

A solution of (2R,6S,13aS,14aR,16aS,E)-ethyl 6-(tert-butoxycarbonylamino)-12,12-difluoro-2-hydroxy-5,16-dioxo-1,2,3,5,6,7,10,11,12,13,13a,14,14a,15,16,16a-hexadecahydrocyclopropa[e]pyrrolo[1,2-a][1,4]diazacyclopentadecine-14a-carboxylate (Example 7h, 1.06 g, 2.002 mmol) in ethyl acetate (50 ml) at 25° C. was added 10% palladium/carbon (0.170 g, 0.160 mmol). The reaction mixture was stirred under a balloon of hydrogen for 2 days. The reaction mixture was filtered through a small plug of silica gel and eluted with ethyl acetate then methanol. The solvent was evaporated under reduced pressure and the resulting solid was purified by flash chromatography on silica gel (40% ethyl acetate/dichloromethane, then ethyl acetate) to provide (2R,6S,13aS,14aR,16aS)-ethyl 6-(tert-butoxycarbonylamino)-12,12-difluoro-2-hydroxy-5,16-dioxooctadecahydrocyclopropa[e]pyrrolo[1,2-a][1,4]diazacyclopentadecine-14a-carboxylate (1.01 g, 1.900 mmol, 95% yield) as a white solid. MS (ESI): m/z=532.3 [M+H].

Example 7j (2R,6S,13aS,14aR,16aS)-6-(tert-butoxycarbonylamino)-12,12-difluoro-2-hydroxy-5,16-dioxooctadecahydrocyclopropa[e]pyrrolo[1,2-a][1,4]diazacyclopentadecine-14a-carboxylic acid

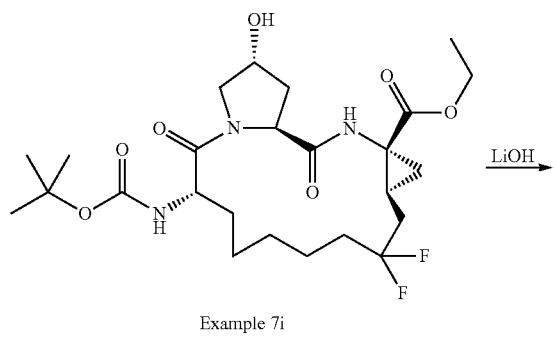

Example 7i

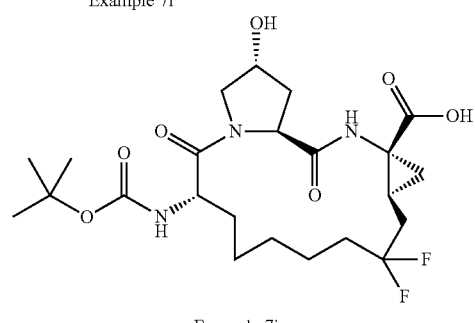

Example 7j

To (2R,6S,13aS,14aR,16aS)-ethyl 6-(tert-butoxycarbonylamino)-12,12-difluoro-2-hydroxy-5,16-dioxooctadecahydrocyclopropa[e]pyrrolo[1,2-a][1,4]diazacyclopentadecine-14a-carboxylate (Example 7i, 900 mg, 1.693 mmol) was added tetrahydrofuran (5.6 ml), methanol (2.80 ml) and water (2.80 ml). Lithium hydroxide monohydrate (145.44 mg, 3.47 mmol) was added at room temperature, and the reaction mixture was stirred at 40° C. for 16 h. The reaction mixture was diluted with CH3CN and neutralized with HCl (2 N, 1.7 ml). The mixture was concentrated under reduced pressure and azeotroped with chloroform followed by ethyl acetate and dried overnight at reduced pressure to provide the title compound (850 mg, quantitative yield). This material was utilized in subsequent reactions without additional purification.

Example 7k (2R,6S,13aS,14aR,16aS)-6-(tert-butoxycarbonylamino)-2-(3-ethylquinoxalin-2-yloxy)-12,12-difluoro-5,16-dioxooctadecahydrocyclopropa[e]pyrrolo[1,2-a][1,4]diazacyclopentadecine-14a-carboxylic acid

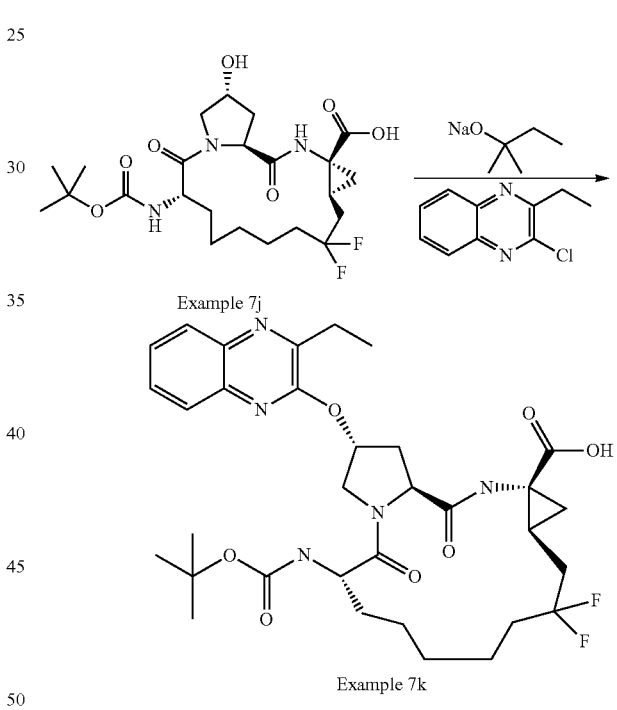

Example 7k

To (2R,6S,13aS,14aR,16aS)-6-(tert-butoxycarbonylamino)-12,12-difluoro-2-hydroxy-5,16-dioxooctadecahydrocyclopropa[e]pyrrolo[1,2-a][1,4]diazacyclopentadecine-14a-carboxylic acid (Example 7j, 87.4 mg, 0.174 mmol) was added 2-chloro-3-ethylquinoxaline (47.7 mg, 0.247 mmol) and DMF (868 µl). To this solution was added sodium tert-pentoxide (48.9 mg, 0.444 mmol) at room temperature, and the mixture turned dark purple (slightly exothermic). The reaction mixture was stirred at room temperature for 17 h. Additional 2-chloro-3-ethylquinoxaline (18.1 mg, 0.094 mmol) and sodium tert-pentoxide (24.2 mg, 0.202 mmol) were added, and the reaction mixture was stirred for 22 h. The reaction mixture was diluted with CH3CN and neutralized with HCl (1 N, 0.7 ml) and evaporated under reduced pressure. The residue was purified by reverse phase HPLC (CH3CN/H2O (0.1%TFA), gradient=20/80-85/15) to provide the title compound as a light brown solid, (2R,6S,13aS, 14aR,16aS)-6-(tert-butoxycarbonylamino)-2-(3-ethylquinoxalin-2-yloxy)-12,12-difluoro-5,16-dioxooctadecahydrocyclopropa[e]pyrrolo[1,2-a][1,4]diazacyclopentadecine-14a-carboxylic acid (66 mg, 57% yield).

Example 7 tert-butyl (2R,6S,13aS,14aR,16aS)-14a-(cyclopropylsulfonylcarbamoyl)-2-(3-ethylquinoxalin-2-yloxy)-12,12-difluoro-5,16-dioxooctadecahydrocyclopropa[e]pyrrolo [1,2-a][1,4]diazacyclopentadecin-6-ylcarbamate

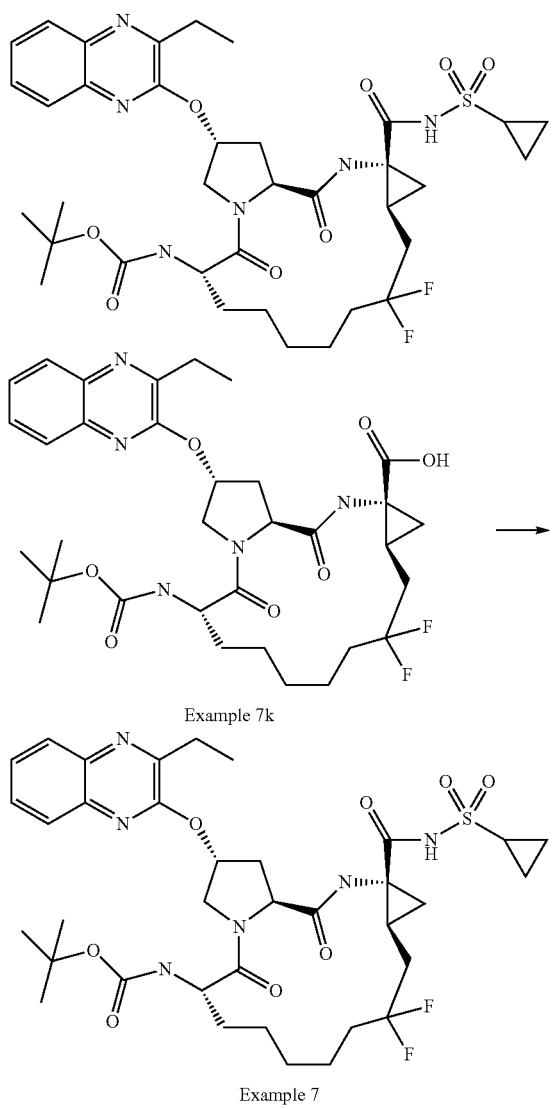

To (2R,6S,13aS,14aR,16aS)-6-(tert-butoxycarbonylamino)-2-(3-ethylquinoxalin-2-yloxy)-12,12-difluoro-5,16-dioxooctadecahydrocyclopropa[e]pyrrolo [1,2-a][1,4]diazacyclopentadecine-14a-carboxylic acid (Example 7k, 26.2 mg, 0.040 mmol) was added sieves (4 A) and dichloroethane (397 μl). To this mixture was added carbonyldiimidazole (13.5 mg, 0.083 mmol), and the reaction mixture was stirred at 40° C. for 2 hr. The reaction mixture was then cooled to room temperature and cyclopropanesulfonamide (12.4 mg, 0.103 mmol) was added followed by DBU (15 μl, 0.100 mmol). The reaction mixture was stirred at room temperature for 16 h, diluted with dichloromethane and cooled to 0° C. This mixture was neutralized with HCl (4 N in dioxane, 67 μl), and the mixture was filtered to remove sieves. The eluant was concentrated under reduced pressure and the residue was purified by reverse phase HPLC (CH3CN/H2O (0.1% TFA) gradient =45/55-85/15) to provide tert-butyl (2R,6S,13aS, 14aR,16aS)-14a-(cyclopropylsulfonylcarbamoyl)-2-(3-ethylquinoxalin-2-yloxy)-12,12-difluoro-5,16-dioxooctadecahydrocyclopropa[e]pyrrolo [1,2-a][1,4] diazacyclopentadecin-6-ylcarbamate (25.8 mg, 85% yield) as a light yellow solid. MS (ESI): m/z=763.0 [M+H], 761.3 [M–H]. Example 7 provided an $IC_{50}$ of between 0.5 and 1.0 nM in a 1a enzyme assay; an $IC_{50}$ of between 0.1 and 0.5 nM in a 1b enzyme assay; a HLM stability value of >100 μl/min/mg; an $EC_{50}$ of between 2.0 and 5.0 nM in a replicon cell line assay in a 1a-H77 background, and an $EC_{50}$ of between 1.0 and 2.0 nM in a replicon cell line assay in a 1b-con1 background.

Example 8 tert-butyl (2R,6S,13aS,14aR,16aS)-2-(3-ethylquinoxalin-2-yloxy)-12,12-difluoro-14a-(1-methylcyclopropylsulfonylcarbamoyl)-5,16-dioxooctadecahydrocyclopropa[e]pyrrolo[1,2-a][1,4] diazacyclopentadecin-6-ylcarbamate

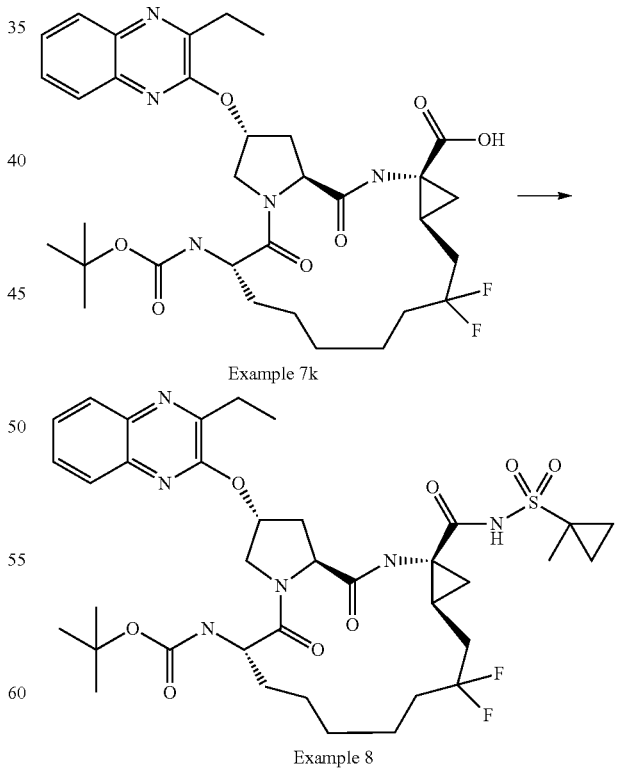

Example 8 was prepared according to the procedure utilized for the preparation of Example 7 from Example 7k, replacing cyclopropanesulfonamide with 1-methylcyclopropane-1- sulfonamide. Yield=67%. MS (ESI): m/z=777.2 [M+H], 775.4 [M−H]. Example 8 provided an IC$_{50}$ of between 0.1 to 0.5 nM in a 1a enzyme assay; an IC$_{50}$ of between 0.1 to 0.5 nM in a 1b enzyme assay; a HLM stability value of >100 µl/min/mg; an EC$_{50}$ of between 2.0 and 5.0 nM in a replicon cell line assay in a 1a-H77 background, and an EC$_{50}$ of between 1.0 and 2.0 nM in a replicon cell line assay in a 1b-con1 background.

Example 9

N-((2R,6S,13aS,14aR,16aS)-14a-(cyclopropylsulfonylcarbamoyl)-2-(3-ethylquinoxalin-2-yloxy)-12,12-difluoro-5,16-dioxooctadecahydrocyclopropa[e]pyrrolo[1,2-a][1,4]diazacyclopentadecin-6-yl)-5-methylisoxazole-3-carboxamide

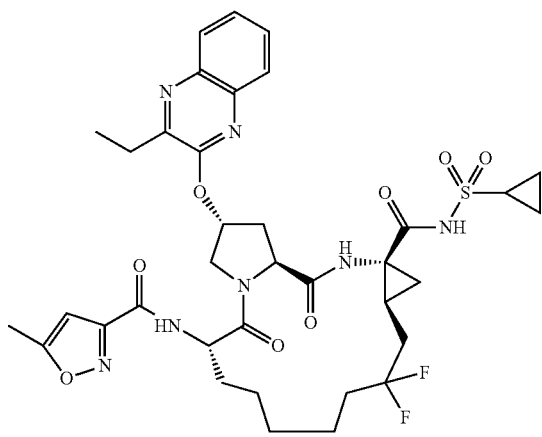 [SMILES: CCc1nc2ccccc2nc1O[C@@H]1C[C@H]2C(=O)N[C@]3(C(=O)NS(=O)(=O)C4CC4)C[C@H]3CC(F)(F)CCCCC[C@H](NC(=O)c3cc(C)on3)C(=O)N2C1]

Example 9a (2R,6S,13aS,14aR,16aS)-6-amino-N-(cyclopropylsulfonyl)-2-(3-ethylquinoxalin-2-yloxy)-12,12-difluoro-5,16-dioxooctadecahydrocyclopropa[e]pyrrolo[1,2-a][1,4]diazacyclopentadecine-14a-carboxamide hydrochloride

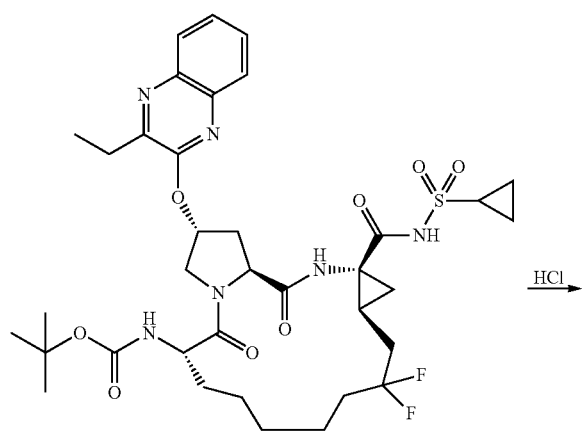

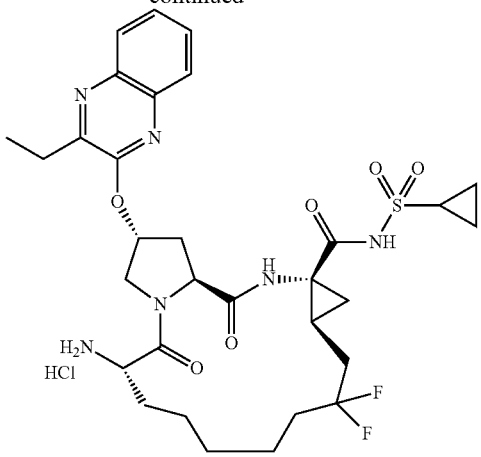

Example 9a was prepared according to the procedure utilized for the preparation of Example 2a, replacing the product of Example 1 with the product of Example 7.

Example 9

N-((2R,6S,13aS,14aR,16aS)-14a-(cyclopropylsulfonylcarbamoyl)-2-(3-ethylquinoxalin-2-yloxy)-12,12-difluoro-5,16-dioxooctadecahydrocyclopropa[e]pyrrolo[1,2-a][1,4]diazacyclopentadecin-6-yl)-5-methylisoxazole-3-carboxamide

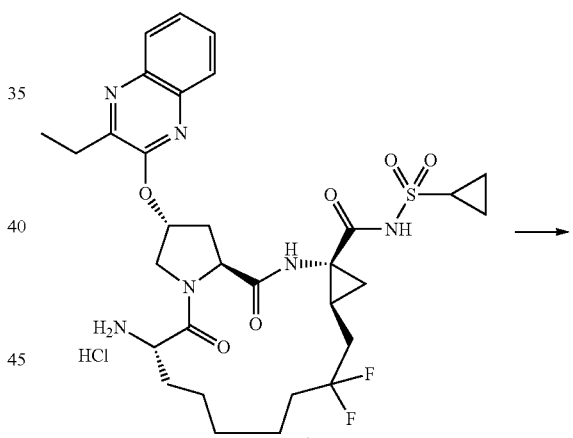

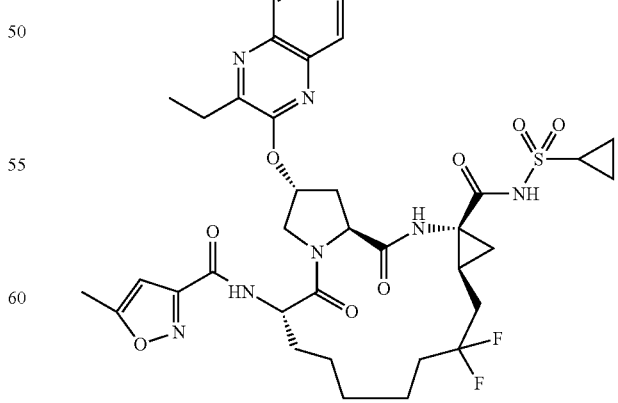

Example 9 was prepared according to the procedure utilized for the preparation of Example 2, replacing the product of Example 2a with the product of Example 9a. Yield=74%. MS (ESI): m/z=772.3 [M+H], 770.4 [M−H].

Example 9 provided an $IC_{50}$ of between 0.5 and 1.0 nM in a 1a enzyme assay; an $IC_{50}$ of between 0.1 and 0.5 nM in a 1b enzyme assay; a HLM stability value of <50 μl/min/mg; an $EC_{50}$ of between 2.0 and 5.0 nM in a replicon cell line assay in a 1a-H77 background, and an $EC_{50}$ of between 1.0 and 2.0 nM in a replicon cell line assay in a 1b-con1 background.

Example 10

N-((2R,6S,13aS,14aR,16aS)-2-(3-ethylquinoxalin-2-yloxy)-12,12-difluoro-14a-(1-methylcyclopropylsulfonylcarbamoyl)-5,16-dioxooctadecahydrocyclopropa[e]pyrrolo [1,2-a][1,4]diazacyclopentadecin-6-yl)-5-methylisoxazole-3-carboxamide

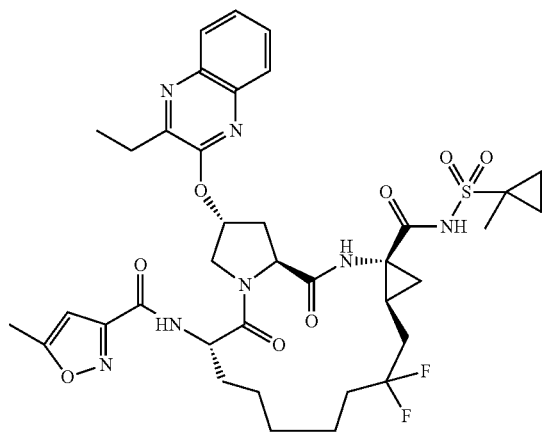 [SMILES: CCc1nc2ccccc2nc1O[C@@H]1C[C@H]2C(=O)N[C@]3(C(=O)NS(=O)(=O)C4(C)CC4)C[C@H]3CC(F)(F)CCCCC[C@H](NC(=O)c3cc(C)on3)C(=O)N2C1]

Example 10a (2R,6S,13aS,14aR,16aS)-6-amino-2-(3-ethylquinoxalin-2-yloxy)-12,12-difluoro-N-(1-methylcyclopropylsulfonyl)-5,16-dioxooctadecahydrocyclopropa[e]pyrrolo [1,2-a][1,4]diazacyclopentadecine-14a-carboxamide hydrochloride

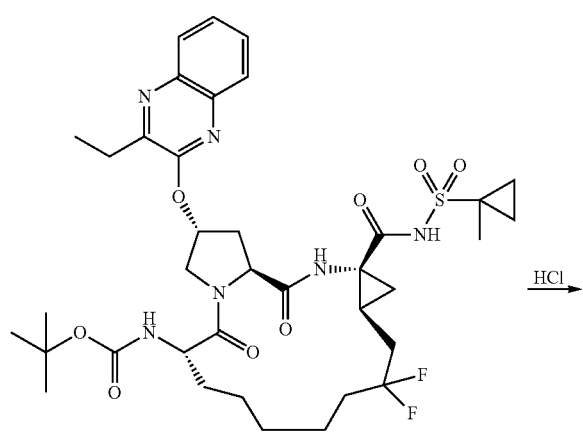

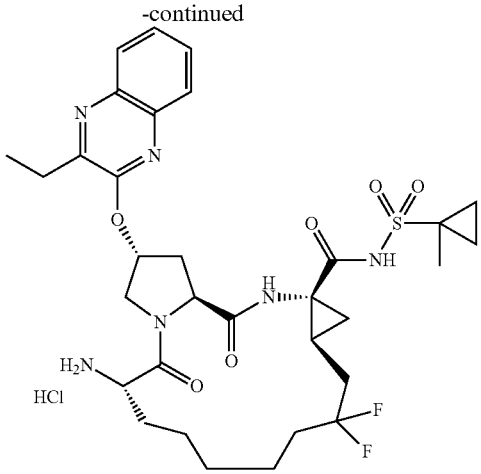

Example 10a was prepared according to the procedure utilized for the preparation of Example 2a, replacing the product of Example 1 with the product of Example 8.

Example 10

N-((2R,6S,13aS,14aR,16aS)-2-(3-ethylquinoxalin-2-yloxy)-12,12-difluoro-14a-(1-methylcyclopropylsulfonylcarbamoyl)-5,16-dioxooctadecahydrocyclopropa[e]pyrrolo[1,2-a][1,4]diazacyclopentadecin-6-yl)-5-methylisoxazole-3-carboxamide

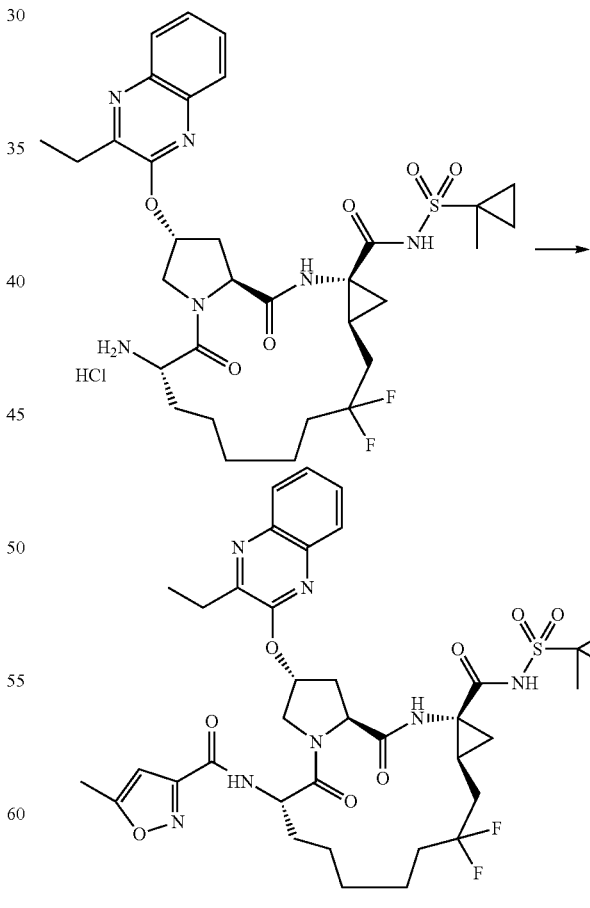

Example 10 was prepared according to the procedure utilized for the preparation of Example 2, replacing the product of Example 2a with the product of Example 10a. Yield=83%. MS (ESI): m/z=786.3 [M+H], 784.3 [M−H].

Example 10 provided a HLM stability value of <50 μl/min/mg; an $EC_{50}$ of between 2.0 and 5.0 nM in a replicon cell line assay in a 1a-H77 background, and an $EC_{50}$ of between 1.0 and 2.0 nM in a replicon cell line assay in a 1b-con1 background.

Example 11

N-((2R,6S,13aS,14aR,16aS)-14a-(cyclopropylsulfonylcarbamoyl)-2-(3-ethylquinoxalin-2-yloxy)-12,12-difluoro-5,16-dioxooctadecahydrocyclopropa[e]pyrrolo[1,2-a][1,4]diazacyclopentadecin-6-yl)isoxazole-3-carboxamide

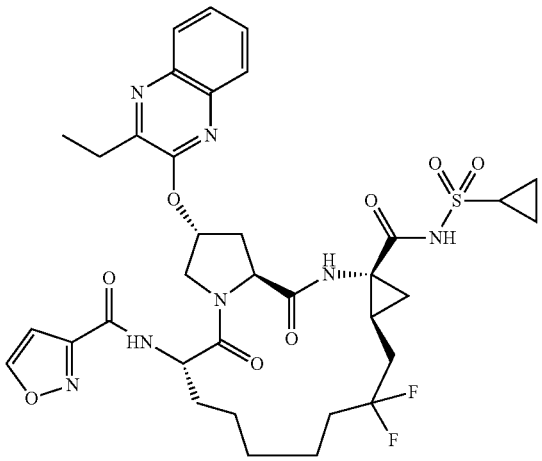 [SMILES: CCc1nc2ccccc2nc1O[C@@H]1C[C@H]2C(=O)N[C@]3(C(=O)NS(=O)(=O)C4CC4)C[C@H]3CC(F)(F)CCCCC[C@H](NC(=O)c3ccon3)C(=O)N2C1]

Example 11 was prepared according to the procedure utilized for the preparation of Example 9, replacing 5-methylisoxazole-3-carboxylic acid with isoxazole-3-carboxylic acid. Yield=74%. MS (ESI): m/z=758.6 [M+H], 756.4 [M−H]. Example 11 provided an $IC_{50}$ of between 0.1 and 0.5 nM in a 1a enzyme assay; an $IC_{50}$ of between 0.1 and 0.5 nM in a 1b enzyme assay; a HLM stability value of <50 μl/min/mg; an $EC_{50}$ of >5.0 nM in a replicon cell line assay in a 1a-H77 background, and an $EC_{50}$ of between 2.0 and 5.0 nM in a replicon cell line assay in a 1b-con1 background.

Example 12

(2R,6S,13aS,14aR,16a5)-N-(cyclopropylsulfonyl)-2-(3-ethylquinoxalin-2-yloxy)-12,12-difluoro-5,16-dioxo-6-pivalamidooctadecahydrocyclopropa[e]pyrrolo[1,2-a][1,4]diazacyclopentadecine-14a-carboxamide

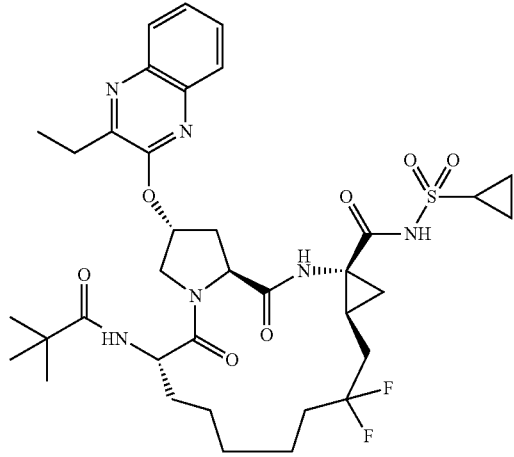 [SMILES: CCc1nc2ccccc2nc1O[C@@H]1C[C@H]2C(=O)N[C@]3(C(=O)NS(=O)(=O)C4CC4)C[C@H]3CC(F)(F)CCCCC[C@H](NC(=O)C(C)(C)C)C(=O)N2C1]

Example 12 was prepared according to the procedure utilized for the preparation of Example 9, replacing 5-methylisoxazole-3-carboxylic acid with pivalic acid. Yield=85%. MS (ESI): m/z=747.3 [M+H], 745.4 [M−H].

Example 12 provided an $IC_{50}$ of between 0.5 and 1.0 nM in a 1a enzyme assay; an $IC_{50}$ of between 0.5 and 1.0 nM in a 1b enzyme assay; a HLM stability value of <50 μl/min/mg; an $EC_{50}$ of >5.0 nM in a replicon cell line assay in a 1a-H77 background, and an $EC_{50}$ of >5.0 nM in a replicon cell line assay in a 1-con1 background.

Example 13 tert-butyl (2R,6S,13aS,14aR,16aS)-2-(3-(benzo[d]thiazol-2-yl)quinoxalin-2-yloxy)-14a-(cyclopropylsulfonylcarbamoyl)-12,12-difluoro-5,16-dioxooctadecahydrocyclopropa[e]pyrrolo [1,2-a][1,4]diazacyclopentadecin-6-ylcarbamate

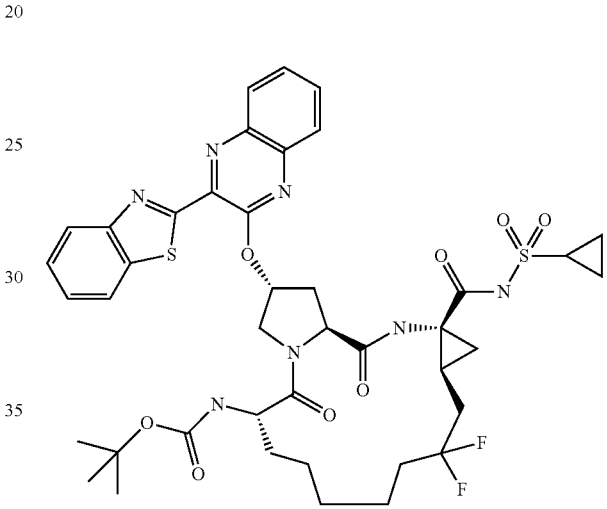

Example 13a ethyl 2-(benzo[d]thiazol-2-yl)-2-oxoacetate

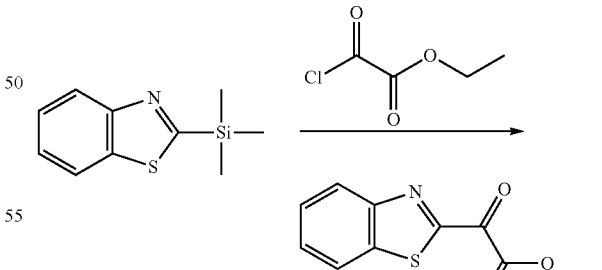

Example 13a

To a solution of ethyl oxalyl chloride (0.537 ml, 4.82 mmol) in dichloromethane (2.411 ml) was added slowly a solution of 2-(trimethylsilyl)benzothiazole (0.945 ml, 4.82 mmol) in dichloromethane (2.4 ml) stirring at 0° C. The reaction mixture was stirred at 0° C. for 30 min allowed to warm slowly to room temperature with stirring over 16 h. The reaction mixture was evaporated under reduced pressure and purified by flash chromatography on silica gel (hex/EA/dichloromethane=8/1/1) to provide the title compound (ethyl 2-(benzo[d]thiazol-2-yl)-2-oxoacetate, 116.2 mg, 10% yield) as an oil.

Example 13b 3-(benzo[d]thiazol-2-yl)quinoxalin-2-ol

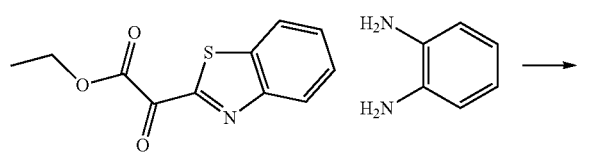

Example 13a

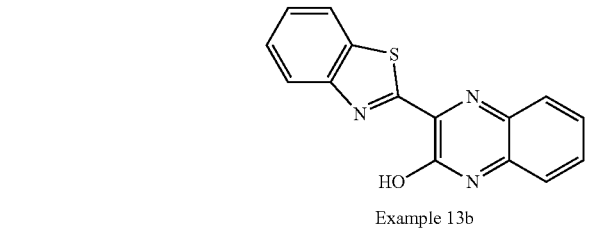

Example 13b

To a solution of ethyl 2-(benzo[d]thiazol-2-yl)-2-oxoacetate (Example 13a, 655 mg, 2.78 mmol) in EtOH (5.6 mL) was added o-phenylenediamine (300 mg, 2.78 mmol). The reaction mixture was heated with stirring at 90° C. for 1 hr (a yellow/green solid appeared quickly), cooled to 0° C., and the solid filtered and rinsed with cold EtOH. The solid was dried under vacuum overnight to provide the title compound (3-(benzo[d]thiazol-2-yl)quinoxalin-2-ol, 313 mg, 40% yield) as a yellow green solid.

Example 13c 2-(3-chloroquinoxalin-2-yl)benzo[d]thiazole

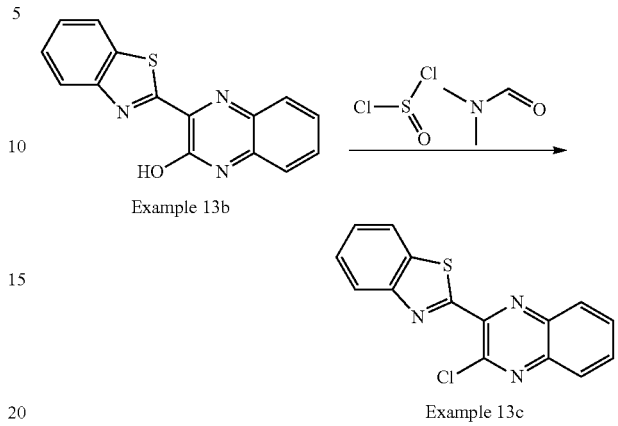

Example 13c

To a suspension of 3-(benzo[d]thiazol-2-yl)quinoxalin-2-ol (251 mg, 0.900 mmol) in toluene (4500 μl) was added thionyl chloride (131 μl, 1.800 mmol) followed by DMF (69.7 μl, 0.900 mmol). The green mixture was stirred at 110° C. for 3 hr. The reaction mixture was evaporated under reduced pressure and the resulting solid was diluted with CHCl3 (30-40 ml) and the insoluble solid filtered and rinsed with CHCl3. The filtrate was evaporated under reduced pressure and the residue purified by flash chromatography on silica gel (eluted with chloroform, then dichloromethane) to provide the title compound as a light yellow solid.

Example 13d (2R,6S,13aS,14aR,16aS)-2-(3-(benzo[d]thiazol-2-yl)quinoxalin-2-yloxy)-6-(tert-butoxycarbonylamino)-12,12-difluoro-5,16-dioxooctadecahydrocyclopropa[e]pyrrolo[1,2-a][1,4]diazacyclopentadecine-14a-carboxylic acid

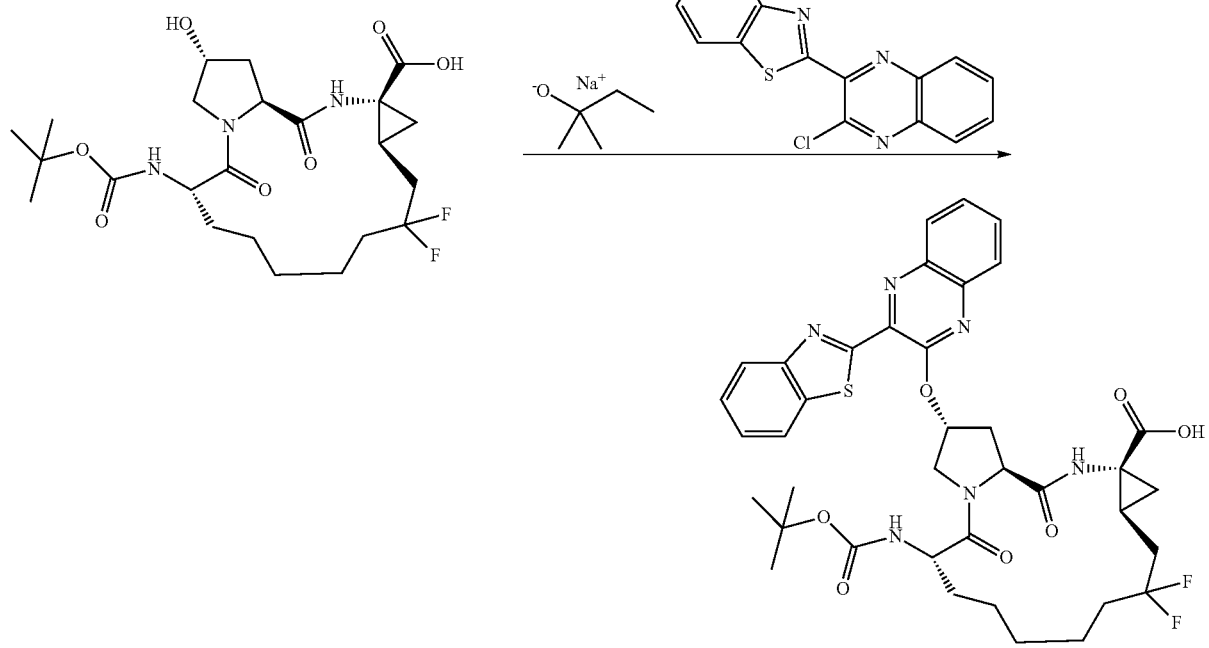

To (2R,6S,13aS,14aR,16aS)-6-(tert-butoxycarbonylamino)-12,12-difluoro-2-hydroxy-5,16-dioxooctadecahydrocyclopropa[e]pyrrolo[1,2-a][1,4]diazacyclopentadecine-14a-carboxylic a (Example 13c, 13 mg, 0.026 mmol) was added DMF (129 µl). Sodium tert-pentoxide (6.28 mg, 0.057 mmol) was added in one portion at room temperature and the mixture was stirred at room temperature for 45 minutes. 2-(3-Chloroquinoxalin-2-yl)benzo[d]thiazole (9.13 mg, 0.031 mmol) was added at room temperature. The resulting yellow mixture was stirred at room temperature for 22 hr. The reaction mixture was diluted with CH3CN, neutralized with HCl (2 N, 15 µl), and evaporated under reduced pressure. The solid was diluted with CH3CN/H2O (0.1% TFA)/DMSO and filtered to remove insoluble yellow solid. The filtrate was purified by reverse phase HPLC (C18, CH3CN/H2O (0.1% TFA)=30/70 to 100/0, 15 min) to provide the title compound (5.2 mg, 26% yield).

Example 13
tert-butyl (2R,6S,13aS,14aR,16aS)-2-(3-(benzo[d]thiazol-2-yl)quinoxalin-2-yloxy)-14a-(cyclopropylsulfonylcarbamoyl)-12,12-difluoro-5,16-dioxooctadecahydrocyclopropa[e]pyrrolo[1,2-a][1,4]diazacyclopentadecin-6-ylcarbamate To a solution of (2R,6S,13aS,14aR,16aS)-2-(3-(benzo[d]thiazol-2-yl)quinoxalin-2-yloxy)-6-(tert-butoxycarbonylamino)-12,12-difluoro-5,16-dioxooctadecahydrocyclopropa[e]pyrrolo[1,2-a][1,4]diazacyclopentadecine-14a-carboxylic acid (Example 13d, 6.22 mg, 8.13 µmol) was added molecular sieves and DCE (81 µl). CDI (2.91 mg, 0.018 mmol) was added, and the mixture was stirred at 40° C. for 2 h. The reaction mixture was cooled to rt and cyclopropanesulfonamide (2.4 mg, 0.020 mmol) was added followed by DBU (3 µl, 0.020 mmol). The mixture was stirred at rt for 2.5 h, diluted with dichloromethane and cooled to 0° C. The mixture was neutralized with HCl (14 µl, 4 N in dioxane, diluted with EA) and stirred for 5 min at 0° C., and evaporated under reduced pressure. The residue was purified by silica gel prep-TLC (dichloromethane/EA =1/1) to provide the title compound as a yellow solid, (5.2 mg, 74% yield). MS (ESI): m/z=868.3 [M+H], 866.3 [M−H].

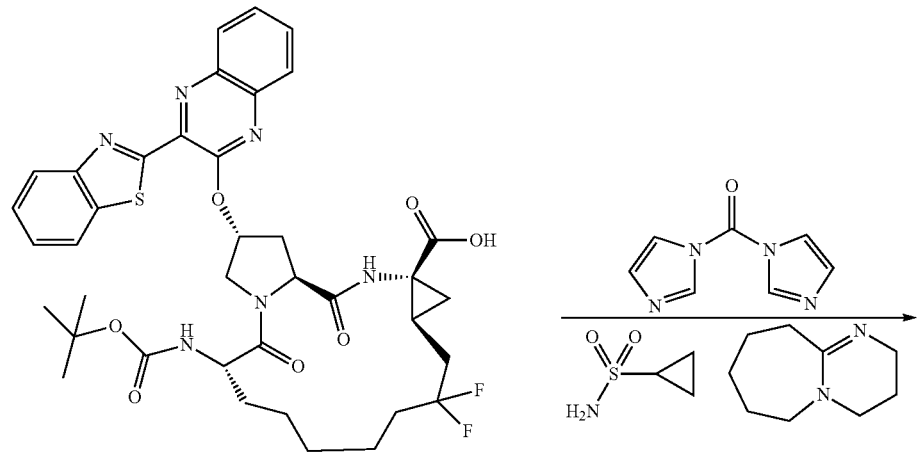

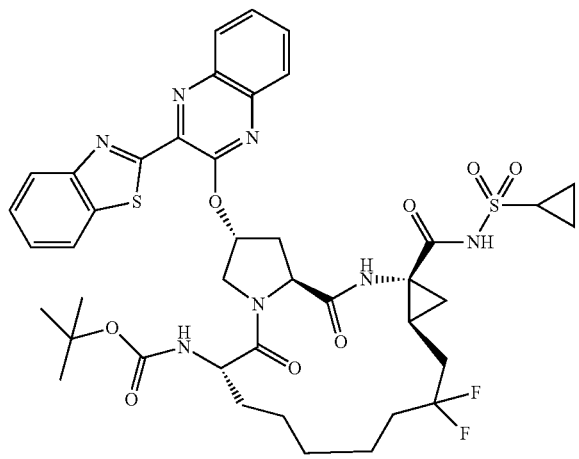

Example 14

N-((2R,6S,13aS,14aR,16aS)-2-(3-(benzo [d]thiazol-2-yl)quinoxalin-2-yloxy)-14a-(cyclopropylsulfonylcarbamoyl)-12,12-difluoro-5,16-dioxooctadecahydrocyclopropa[e]pyrrolo[1,2-a][1,4]diazacyclopentadecin-6-yl)-5-methylisoxazole-3-carboxamide

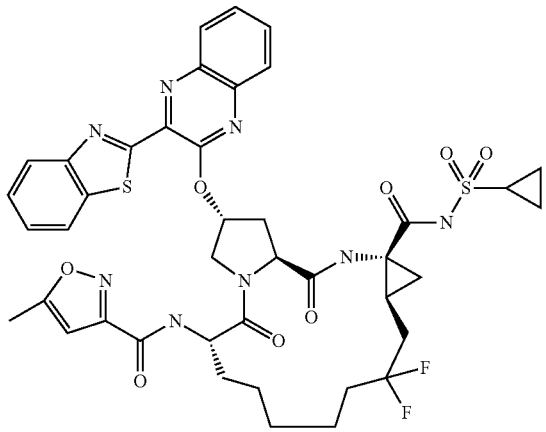 [SMILES: Cc1cc(C(=O)N[C@H]2CCCCCC(F)(F)C[C@@H]3C[C@@]3(C(=O)NS(=O)(=O)C3CC3)NC(=O)[C@@H]3C[C@@H](Oc4nc5ccccc5nc4-c4nc5ccccc5s4)CN3C2=O)no1]

Example 14a (2R,6S,13aS,14aR,16aS)-6-amino-2-(3-(benzo[d]thiazol-2-yl)quinoxalin-2-yloxy)-N-(cyclopropylsulfonyl)-12,12-difluoro-5,16-dioxooctadecahydrocyclopropa[e]pyrrolo [1,2-a][1,4]diazacyclopentadecine-14a-carboxamide hydrochloride

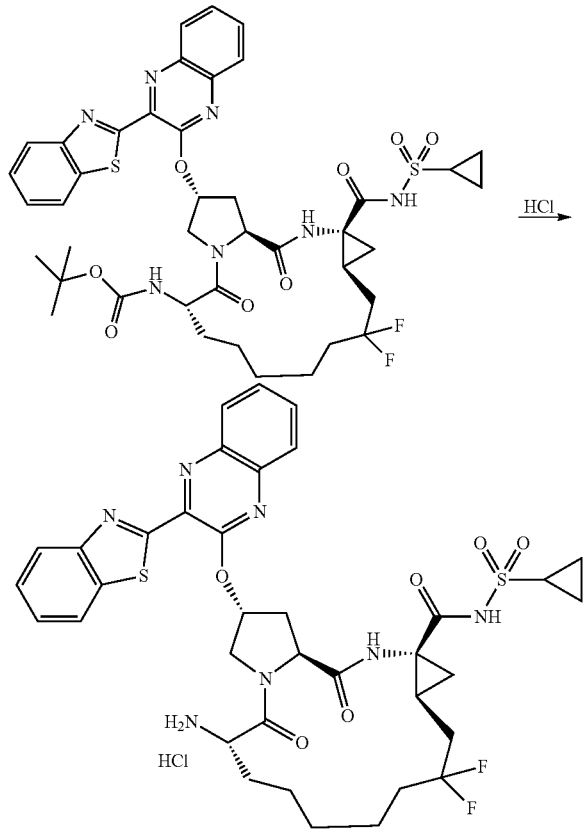

To a solution of tert-butyl (2R,6S,13aS,14aR,16aS)-2-(3-(benzo [d]thiazol-2-yl)quinoxalin-2-yloxy)-14a-(cyclopropylsulfonylcarbamoyl)-12,12-difluoro-5,16-dioxooctadecahydro cyclopropa[e]pyrrolo[1,2-a][1,4]diazacyclopentadecin-6-ylcarbamate (Example 13, 17.4 mg, 0.020 mmol) in ethyl acetate (100 µl) was added HCl (4 M in dioxane, 100 µl, 0.401 mmol) at rt. The mixture was stirred at rt for 16 h, and more HCl (100 µl, 0.401 mmol) was added, and the reaction mixture stirred for 6 hr. The reaction mixture was concentrated under reduced pressure and azeotroped with EA to provide the title compound as a yellow solid which was used without further purification.

Example 14

N-((2R,6S,13aS,14aR,16aS)-2-(3-(benzo[d]thiazol-2-yl)quinoxalin-2-yloxy)-14a-(cyclopropylsulfonylcarbamoyl)-12,12-difluoro-5,16-dioxooctadecahydrocyclopropa[e]pyrrolo [1,2-a][1,4]diazacyclopentadecin-6-yl)-5-methylisoxazole-3-carboxamide

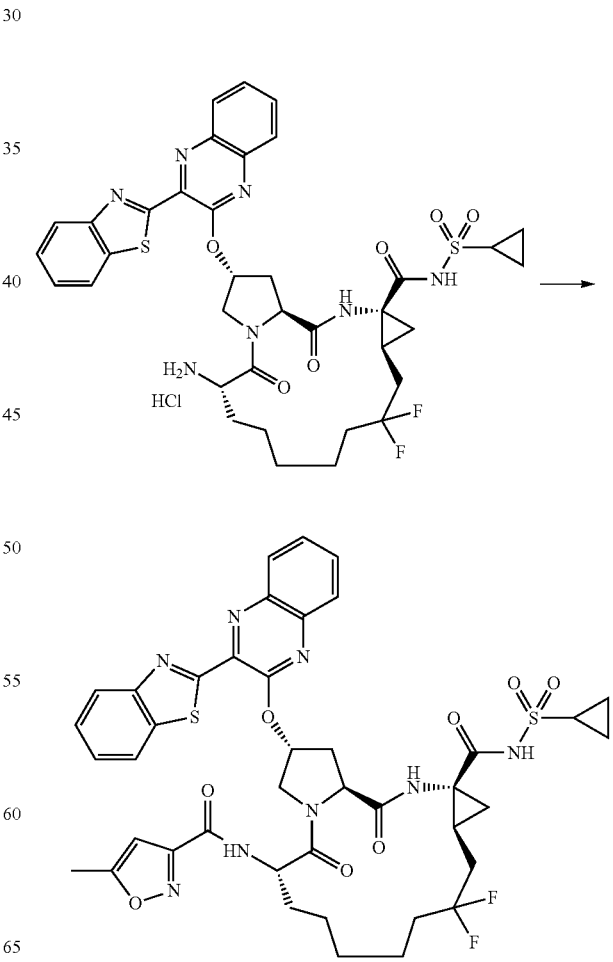

To (2R,6S,13aS,14aR,16aS)-6-amino-2-(3-(benzo [d]thia-zol-2-yl)quinoxalin-2-yloxy)-N-(cyclopropylsulfonyl)-12, 12-difluoro-5,16-dioxooctadecahydrocyclopropa[e]pyrrolo[1,2-a][1,4]diazacyclopentadecine-14a-carboxamide, Hydrochloric Acid (Example 14a, 16.1 mg, 0.020 mmol) was added DMF (200 μl) and diisopropylethylamine (25 μl, 0.14 mmol). To the yellow solution was added 5-methylisoxazole-3-carboxylic acid (3.85 mg, 0.030 mmol) followed by HATU (13.89 mg, 0.037 mmol). The reaction mixture was stirred at rt 2 h, cooled to 0° C. and neutralized with HCl (4 N in dioxane, 36 μl, diluted with EA). The solution was concentrated under reduced pressure and purified by prep-TLC (dichloromethane/EA=1/1, 2×) to provide the title compound N-((2R,6S,13aS,14aR,16aS)-2-(3-(benzo [d]thiazol-2-yl)quinoxalin-2- yloxy)-14a-(cyclopropylsulfonylcarbamoyl)-12,12-difluoro-5,16-dioxooctadecahydrocyclopropa[e]pyrrolo[1,2-a][1,4]diazacyclopentadecin-6-yl)-5-methylisoxazole-3-carboxamide (14.3 mg, 81% yield). MS (ESI): m/z=877.1 [M+H], 875.2 [M−H]. Example 14 provided an $IC_{50}$ of between 0.1 and 0.5 nM in a 1a enzyme assay; an $IC_{50}$ of between 0.1 and 0.5 nM in a 1b enzyme assay; a HLM stability value of <50 μl/min/mg; an $EC_{50}$ of between 2.0 and 5.0 nM in a replicon cell line assay in a 1a-H77 background, and an $EC_{50}$ of between 1.0 and 2.0 nM in a replicon cell line assay in a 1-con1 background.

Example 15 tert-butyl (2R,6S,13aS,14aR,16aS)-2-(3-(benzofuran-2-yl)quinoxalin-2-yloxy)-14a-(cyclopropylsulfonylcarbamoyl)-12,12-difluoro-5,16-dioxooctadecahydrocyclopropa[e]pyrrolo[1,2-a][1,4]diazacyclopentadecin-6-ylcarbamate

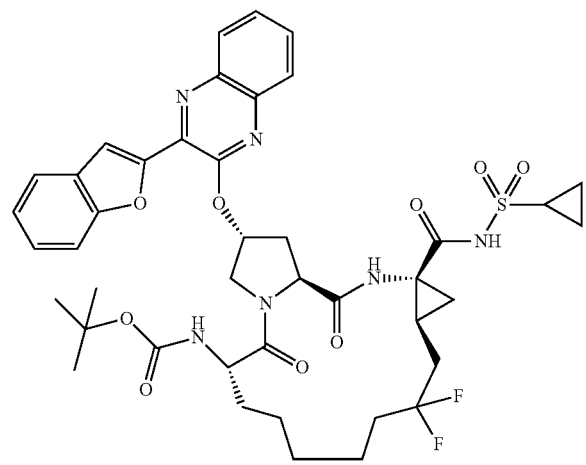 [SMILES: CC(C)(C)OC(=O)N[C@H]1CCCCCC(F)(F)C[C@@H]2C[C@@]2(C(=O)NS(=O)(=O)C2CC2)NC(=O)[C@@H]2C[C@@H](Oc3nc4ccccc4nc3-c3cc4ccccc4o3)CN2C1=O]

Example 15a ethyl 2-(benzofuran-2-yl)-2-oxoacetate

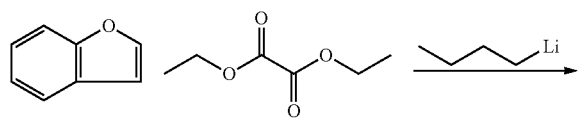

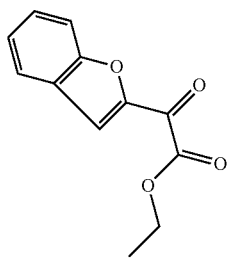

To a solution of benzofuran (0.250 mL, 2.32 mmol) in tetrahydrofuran (12.5 mL) stirring at −100° C. ($CO_2$, ether bath) was added n-BuLi (1.377 mL, 2.203 mmol, 1.6 M in hexanes). The reaction was stirred for 30 min (yellow color) and added dropwise via a canulated into a solution of diethyl oxalate (0.314 mL, 2.32 mmol) in tetrahydrofuran (7 mL) stirring at −100° C. The reaction mixture was stirred for 1 h and then quenched with saturated aqueous ammonium chloride solution. The mixture was warmed to rt, diluted with dichloromethane, and washed with 0.1 N HCl. The organic layer was separated, dried over anhydrous magnesium sulfate, filtered, and evaporated under reduced pressure. The residue was purified by flash chromatography on silica gel (eluted with dichloromethane). The fractions containing the title compound were collected and repurified by flash chromatography on silica gel (25% acetone/hexane) to provide the title compound (ethyl 2-(benzofuran-2-yl)-2-oxoacetate, 237 mg, 47% yield).

Example 15b 3-(benzofuran-2-yl)quinoxalin-2-ol

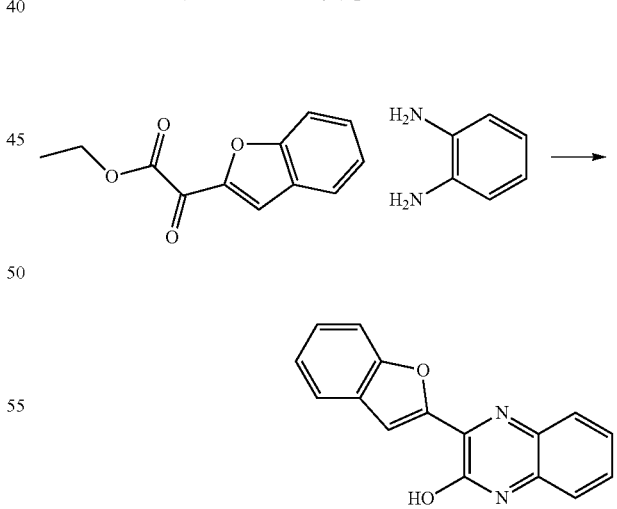

To a solution of ethyl 2-(benzofuran-2-yl)-2-oxoacetate (Example 15a, 237 mg, 1.09 mmol) in EtOH (2.7 mL) was added o-phenylenediamine (117 mg, 1.09 mmol). The reaction mixture was stirred at 90° C. for 16 h (a yellow solid appeared quickly). The mixture was cooled to 0° C., filtered, and the solid rinsed with cold EtOH. The yellow solid was azeotroped with CHCl3 and benzene and dried to provide the title compound (268 mg, 94% yield).

Example 15c 2-(benzofuran-2-yl)-3-chloroquinoxaline

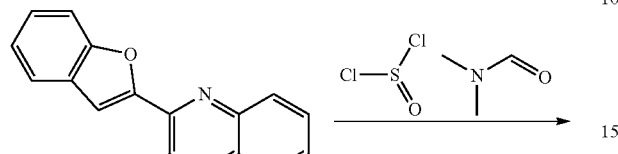

To a suspension of 3-(benzofuran-2-yl)quinoxalin-2-ol (Example 15b, 268 mg, 1.02 mmol) in Toluene (5.1 mL) was added thionyl chloride (0.30 mL, 4.1 mmol) followed by DMF (238 µl, 3.07 mmol). The yellow reaction mixture was stirred at 110° C. for 2 h, cooled to room temperature, and evaporated under reduced pressure to gave a yellow solid. The solid was suspended in dichloromethane (20 ml) and purified by flash chromatography on silica gel (dichloromethane) to give the title compound, 2-(benzofuran-2-yl)-3-chloroquinoxaline (297 mg, quantitative yield), as a yellow solid.

Example 15d (2R,6S,13aS,14aR,16aS)-2-(3-(benzofuran-2-yl)quinoxalin-2-yloxy)-6-(tert-butoxycarbonylamino)-12,12-difluoro-5,16-dioxooctadecahydrocyclopropa[e]pyrrolo[1,2-a][1,4]diazacyclopentadecine-14a-carboxylic acid

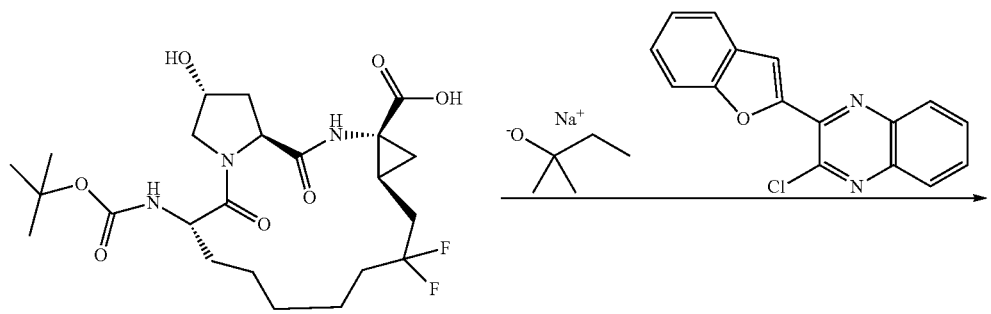

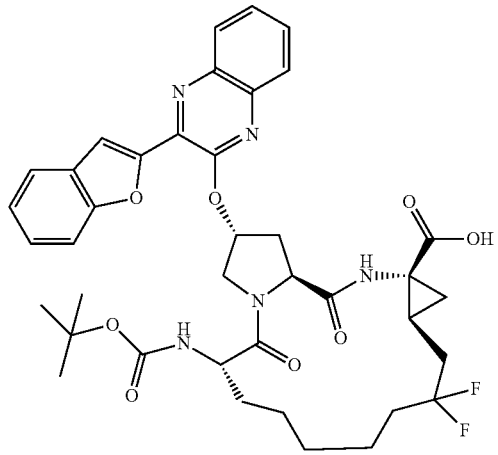

The title compound was prepared according to the procedure utilized for the preparation of Example 13d, replacing the product of Example 13c with the product of Example 15c. Yield=66%.

Example 15
tert-butyl (2R,6S,13aS,14aR,16aS)-2-(3-(benzofuran-2-yl)quinoxalin-2-yloxy)-14a-(cyclopropylsulfonylcarbamoyl)-12,12-difluoro-5,16-dioxooctadecahydrocyclopropa[e]pyrrolo [1,2-a][1,4]diazacyclopentadecin-6-ylcarbamate

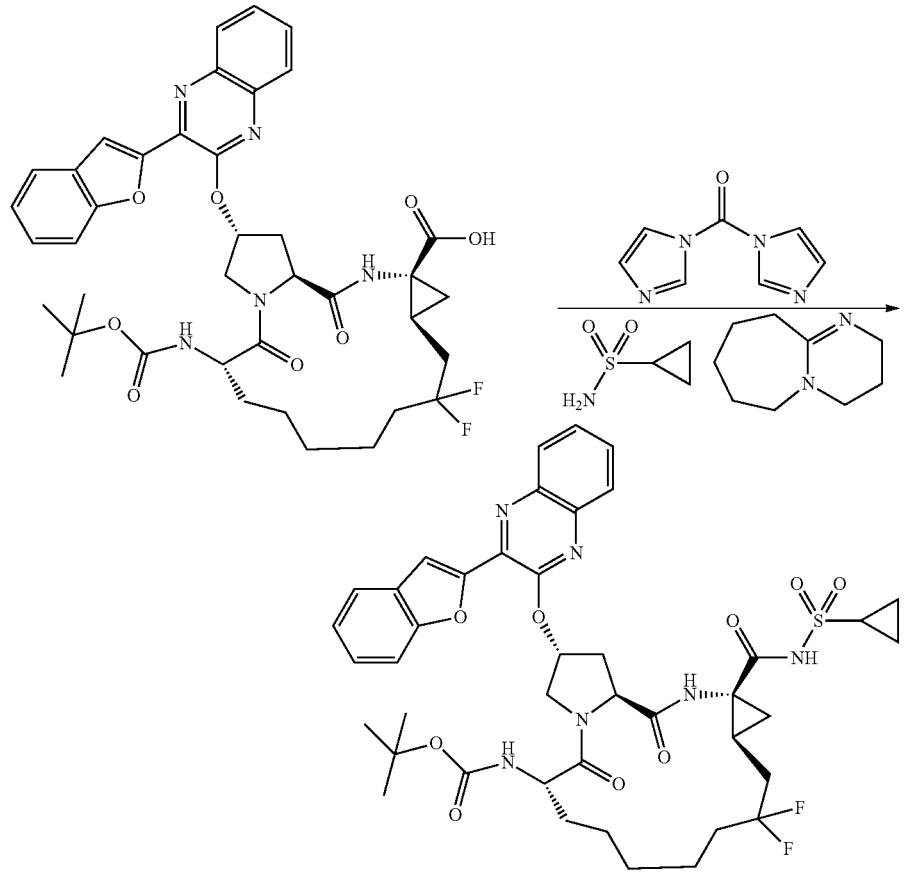

The title compound was prepared according to the procedure utilized for the preparation of Example 13, replacing the product of Example 13d with the product of Example 15d. (91% yield). MS (ESI): m/z=803.6 [M+H].

Example 16
N-((2R,6S,13aS,14aR,16aS)-2-(3-(benzofuran-2-yl)quinoxalin-2-yloxy)-14a-(cyclopropylsulfonylcarbamoyl)-12,12-difluoro-5,16-dioxooctadecahydrocyclopropa[e]pyrrolo [1,2-a][1,4]diazacyclopentadecin-6-yl)-5-methylisoxazole-3-carboxamide

Example 16a
(2R,6S,13aS,14aR,16aS)-6-amino-2-(3-(benzofuran-2-yl)quinoxaline-2-yloxy)-N-(cyclopropylsulfonyl)-12,12-difluoro-5,16-dioxooctadecahydrocyclopropa[e]pyrrolo[1,2-a][1,4]diazacyclopentadecine-14a-carboxamide hydrochloride

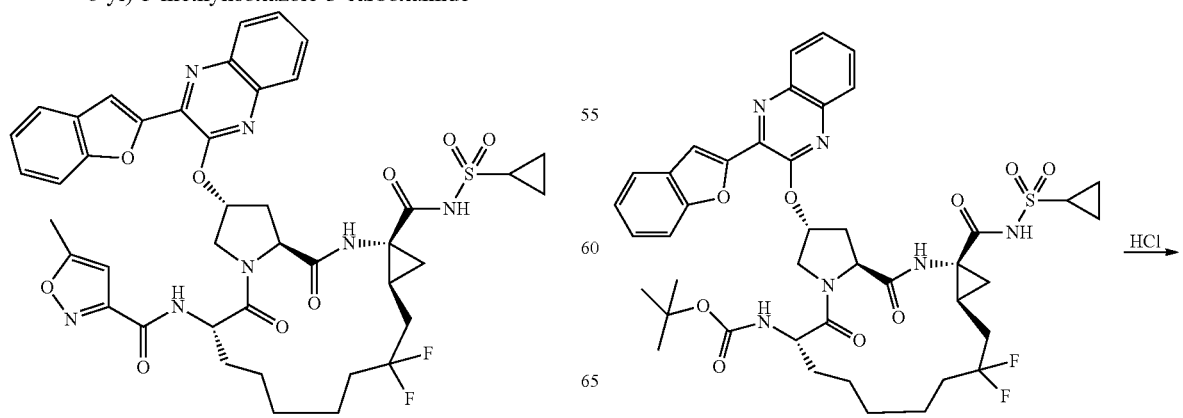

95
-continued

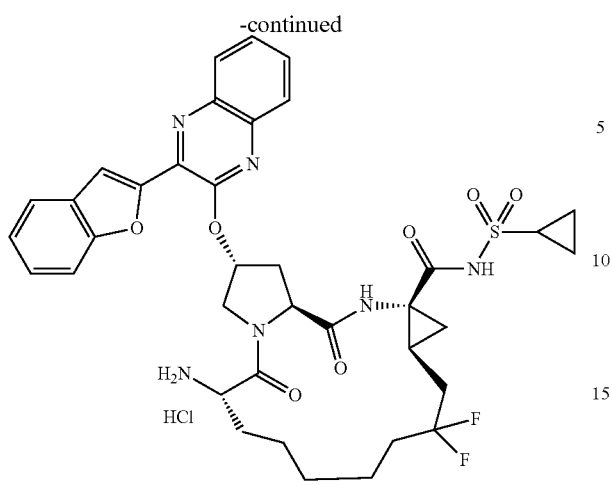

96

The title compound was prepared according to the procedure utilized for the preparation of Example 14a, replacing the product of Example 13 with the product of Example 15. (quantitative yield).

Example 16

N-((2R,6S,13aS,14aR,16aS)-2-(3-(benzofuran-2-yl) quinoxaline-2-yloxy)-14a-(cyclopropylsulfonylcarbamoyl)-12,12-difluoro-5,16-dioxooctadecahydrocyclopropa[e]pyrrolo[1,2-a][1,4]diazacyclopentadecin-6-yl)-5-methylisoxazole-3-carboxamide

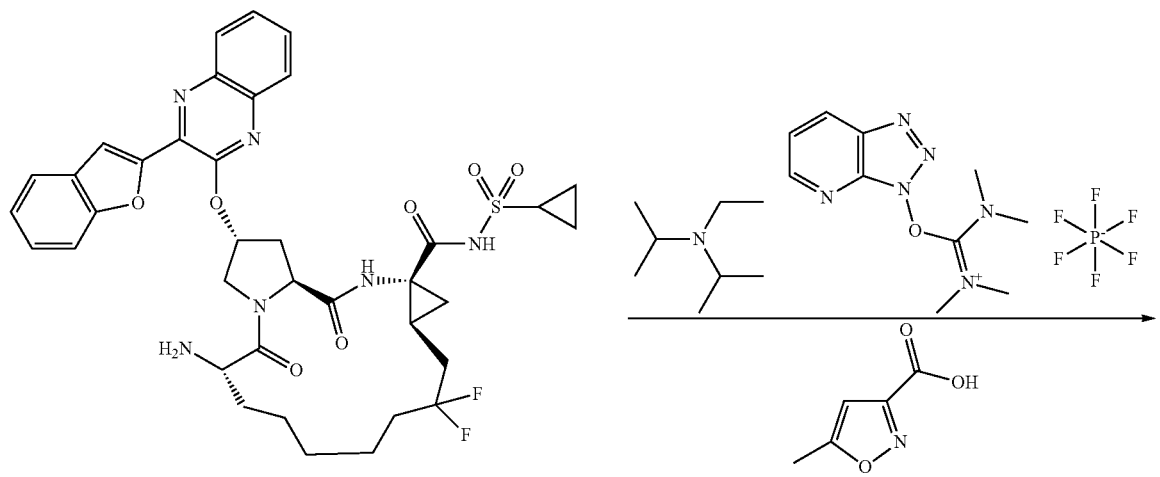

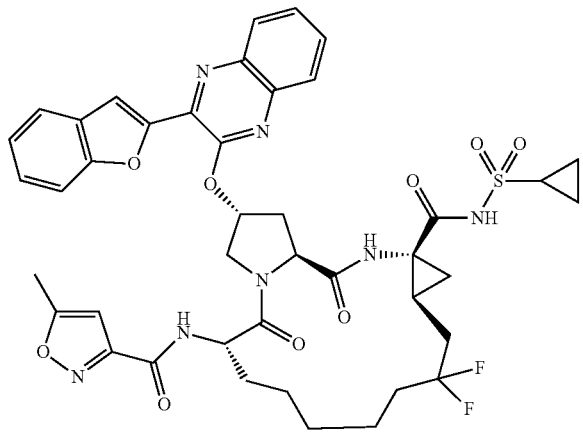

The title compound was prepared according to the procedure utilized for the preparation of Example 14, replacing the product of Example 14a with the product of Example 16a. (68% yield).

MS (ESI): m/z=860.3 [M+H], 858.4 [M−H].

Example 16 provided an $IC_{50}$ of between 0.1 and 0.5 nM in a 1a enzyme assay; an $IC_{50}$ of between 0.1 and 0.5 nM in a 1b enzyme assay; a HLM stability value of between 50 and 100 μl/min/mg; an $EC_{50}$ of between 1.0 and 2.0 nM in a replicon cell line assay in a 1a-H77 background, and an $EC_{50}$ of <1.0 nM in a replicon cell line assay in a 1-con1 background.

Example 17

(2R,6S,13aS,14aR,16aS)-2-(3-(benzofuran-2-yl) quinoxaline-2-yloxy)-N-(cyclopropylsulfonyl)-12, 12-difluoro-6-(1-methyl-1H-pyrazole-3-carboxamido)-5,16-dioxooctadecahydrocyclopropa[e] pyrrolo [1,2-a][1,4]diazacyclopentadecine-14a-carboxamide

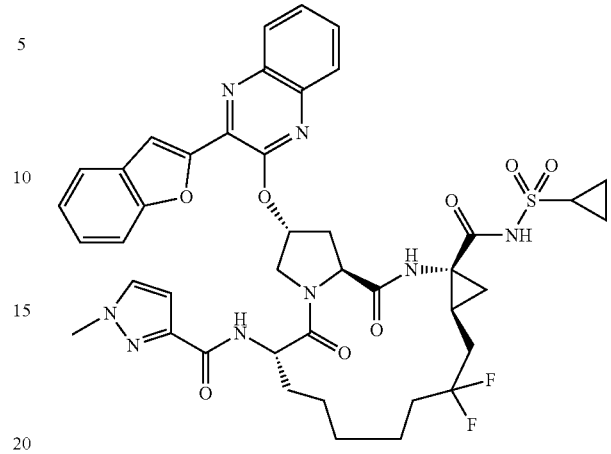

Example 17

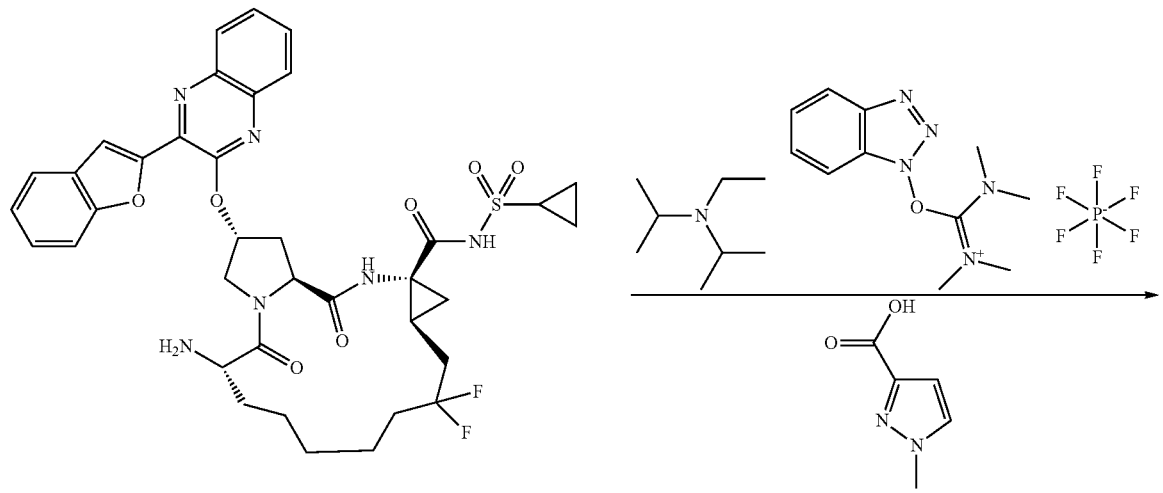

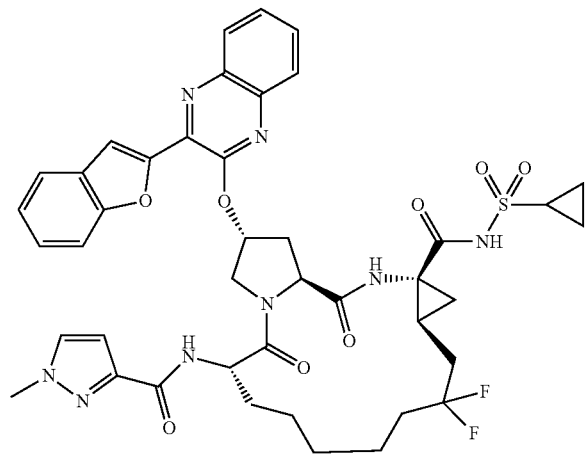

The title compound was prepared according to the procedure utilized for the preparation of Example 16, replacing 5-methylisoxazole-3-carboxylic acid with 1-methyl-1H-pyrazole-3-carboxylic acid. (96% yield). MS (ESI): m/z=859.0 [M+H], 857.4 [M−H].

Example 17 provided an $IC_{50}$ of between 0.1 and 0.5 nM in a 1a enzyme assay; an $IC_{50}$ of <0.1 nM in a 1b enzyme assay; a HLM stability value of <50 μl/min/mg; an $EC_{50}$ of between 2.0 and 5.0 nM in a replicon cell line assay in a 1a-H77 background, and an $EC_{50}$ of <1.0 nM in a replicon cell line assay in a 1-con1 background.

Example 18

N-((2R,6S,13aS,14aR,16aS)-14a-(cyclopropylsulfonylcarbamoyl)-12,12-difluoro-5,16-dioxo-2-(phenanthridin-6-yloxy)octadecahydrocyclopropa[e]pyrrolo[1,2-a][1,4]diazacyclopentadecin-6-yl)-5-methylisoxazole-3-carboxamide

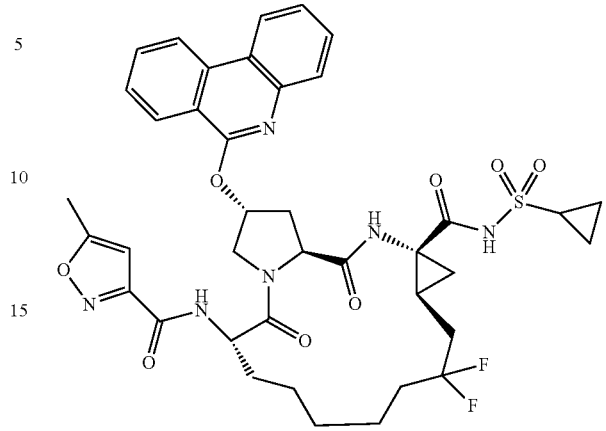

Example 18a (2R,6S,13aS,14aR,16aS,Z)-ethyl 6-(tert-butoxycarbonylamino)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylate

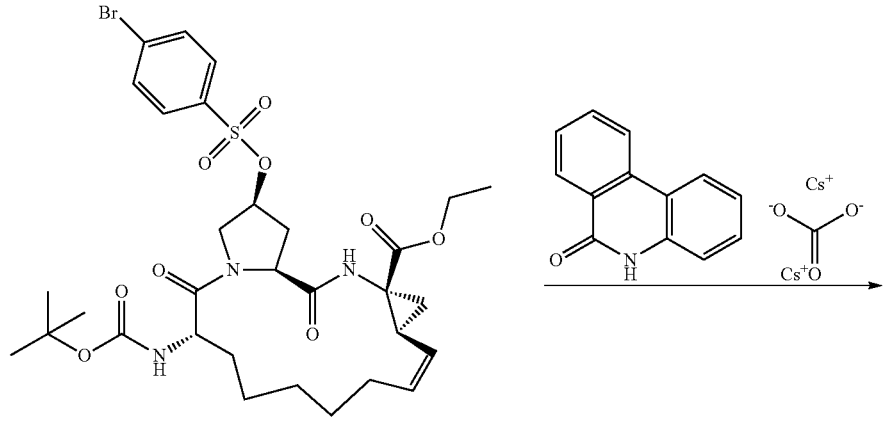

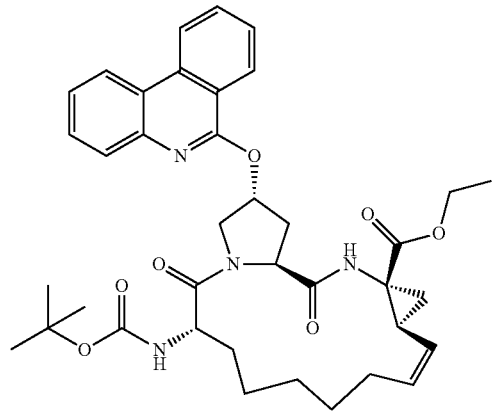

To (2S,6S,13aS,14aR,16aS,Z)-ethyl 2-(4-bromophenylsulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (9.00 g, 12.6 mmol) and phenanthridin-6(5H)-one (3.08 g, 15.8 mmol) was added DMSO (50 ml). To this mixture was added cesium carbonate (6.17 g, 18.9 mmol) and the resulting mixture was heated at 75° C. for 3 hr. The reaction mixture was cooled to room temperature, diluted with water (400 ML) and neutralized with HCl (2N, 7.8 mL). The mixture was filtered and the white solid was rinsed with water. The solid was taken up in dichloromethane and filtered to remove insoluble phenanthridinone. The filtrate was concentrated and the residue was purified flash chromatography on silica gel (4:6 hexane/ethyl acetate) to provide the title compound (2R,6S,13aS,14aR,16aS,Z)-ethyl 6-(tert-butoxycarbonylamino)-5,16-dioxo-2-(phenanthridin yloxy)-1,2,3,5,6,7,8,9,10,11,13a,14,14a,15,16,16a-hexadecahydrocyclopropa[e]pyrrolo [1,2-a][1,4]diazacyclopentadecine-14a-carboxylate as a pale yellow solid (5.07g, 60% yield).

Example 18b (2R,6S,13aS,14aR,16aS,Z)-ethyl 6-amino-5,16-dioxo-2-(phenanthridin-6-yloxy)-1,2,3,5,6,7,8,9,10,11,13a,14,14a,15,16,16a-hexadecahydrocyclopropa[e]pyrrolo [1,2-a][1,4]diazacyclopentadecine-14a-carboxylate hydrochloride

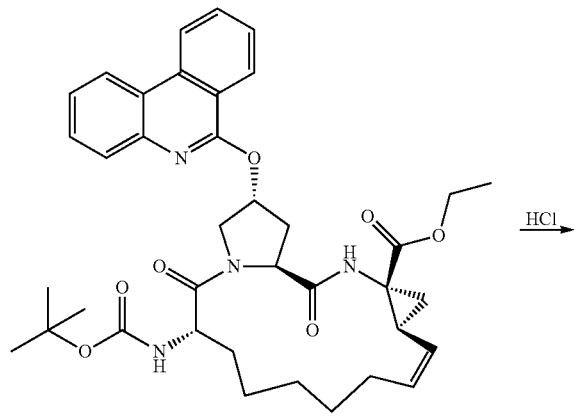

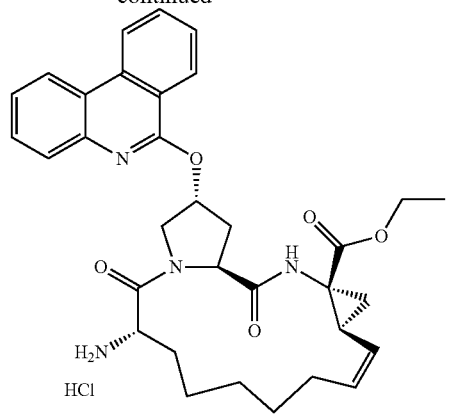

To a solution of (2R,6S,13aS,14aR,16aS,Z)-ethyl 6-(tert-butoxycarbonylamino)-5,16-dioxo-2-(phenanthridin-6-yloxy)-1,2,3,5,6,7,8,9,10,11,13a,14,14a,15,16,16a-hexadecahydrocyclopropa[e]pyrrolo [1,2-a][1,4]diazacyclopentadecine-14a-carboxylate (Example 18a, 6.25 g, 9.32 mmol) dissolved in Ethyl acetate (50 ml) was added 4 N hydrogen chloride in dioxane (44.3 ml, 177 mmol) and the reaction mixture was stirred at rt for 6 h. The solvent was evaporated under reduced pressure to give a white solid which was rinsed with ethyl acetate. The filtered solid was dried to give (2R,6S,13aS,14aR,16aS,Z)-ethyl 6-amino-5,16-dioxo-2-(phenanthridin-6-yloxy)-1,2,3,5,6,7,8,9,10,11,13a,14,14a,15,16,16a-hexadecahydrocyclopropa[e]pyrrolo [1,2-a][1,4]diazacyclopentadecine-14a-carboxylate, Hydrochloric Acid (5.52 g, 98% yield)

Example 18c (2R,6S,13aS,14aR,16aS,Z)-ethyl 6-(5-methylisoxazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylate

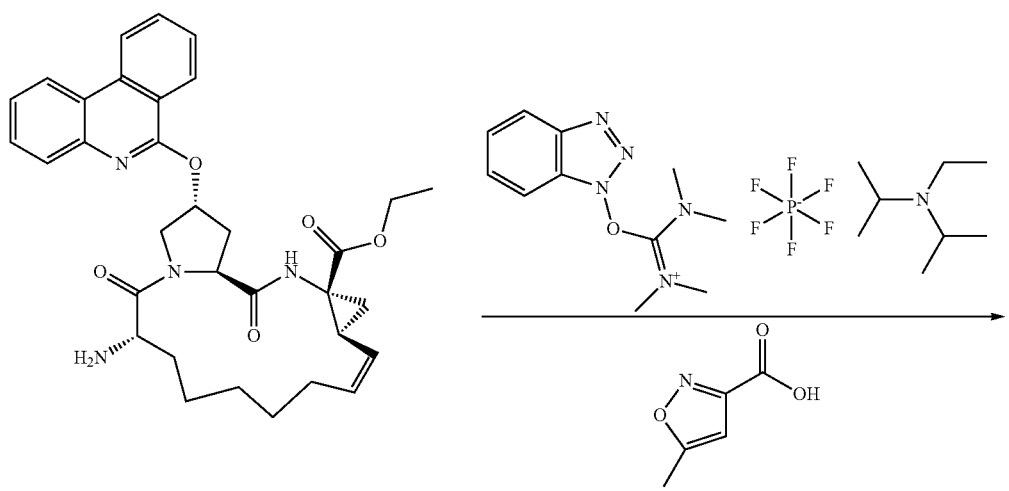

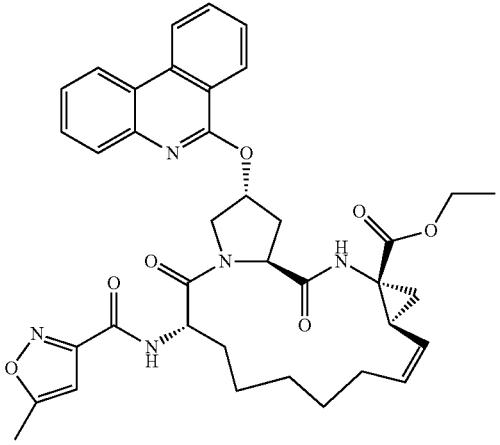

To a suspension of (2R,6S,13aS,14aR,16aS,Z)-ethyl 6-amino-5,16-dioxo-2-(phenanthridin-6-yloxy)-1,2,3,5,6,7,8,9,10,11,13a,14,14a,15,16,16a-hexadecahydrocyclopropa[e]pyrrolo [1,2-a][1,4]diazacyclopentadecine-14a-carboxylate, Hydrochloric Acid (Example 18b, 5.00 g, 8.24 mmol), 5-methylisoxazole-3-carboxylic acid (1.15 g, 9.06 mmol) and 2-(3H41,2,31triazolo[4,5-b]pyridin-3-yl)-1,1,3,3-tetramethylisouronium hexafluorophosphate(V) (3.44 g, 9.06 mmol) in dichloromethane (82 ml) was added N-ethyl-N-isopropylpropan-2-amine (5.03 ml, 28.8 mmol). The mixture was stirred at rt for 2 h, and then quenched with saturated aqueous sodium carbonate solution. The organic layer was washed with 1N HCl, separated, filtered, dried over anhydrous magnesium sulfate and evaporated under reduced pressure to provide a white foam.
This material was purified flash chromatography on silica gel (4:1 dichloromethane/ethyl acetate) to give (2R,6S,13aS,14aR,16aS,Z)-ethyl 6-(5-methylisoxazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylate (4.5 g, 80% yield).

Example 18d (2R,6S,13aS,14aR,16aS,Z)-6-(5-methylisoxazole-3-carboxamido)-5,16-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid

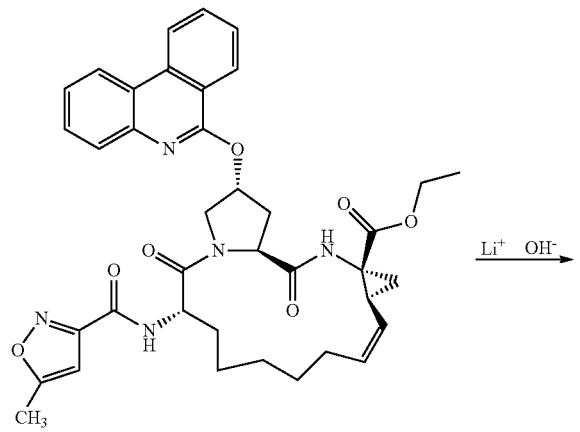

Li⁺ OH⁻ →

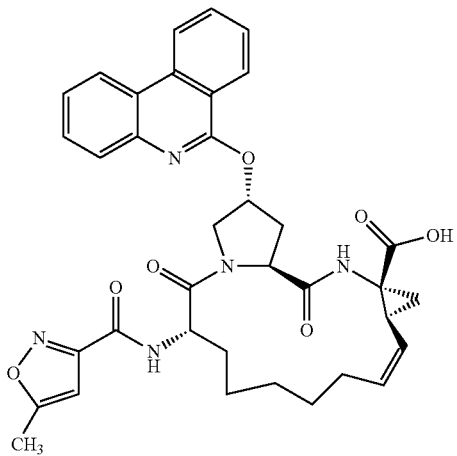

To a solution of (2R,6S,13aS,14aR,16aS,Z)-ethyl 6-(5-methylisoxazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo [1,2-a][1,4]diazacyclopentadecine-14a-carboxylate (Example 18c, 3.4 g, 5.0 mmol) in tetrahydrofuran (16.7 ml), ethanol (8.4 mL), and water (8.4 mL) was added lithium hydroxide monohydrate (1.36 g, 32.5 mmol). The mixture was stirred at 50° C. for 2 h, the solvent was evaporated under reduced pressure, and the residue partitioned between water and ethyl acetate. The aqueous layer was separated, diluted with ethyl acetate, and washed with 1N HCl. The organic layer was dried over anhydrous sodium sulfate, filtered, and evaporated under reduced pressure to give (2R,6S,13aS,14aR,16aS,Z)-6-(5-methylisoxazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (3.05 g, 94% yield) as a white solid.

Example 18e (2R,6S,13aS,14aR,16aS,Z)-tert-butyl 6-(5-methyl-isoxazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo [1,2-a][1,4]diazacyclopentadecine-14a-carboxylate

Example 18f (2R,6S,13aS,14aR,16aS)-tert-butyl 12-hydroxy-6-(5-methylisoxazole-3-carboxamido)-5,16-dioxo-2-(phenanthridin-6-yloxy)octadecahydrocyclopropa[e]pyrrolo[1,2-a][1,4]diazacyclopentadecine-14a-carboxylate

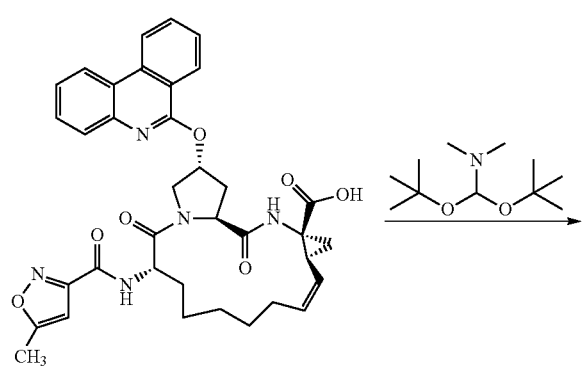

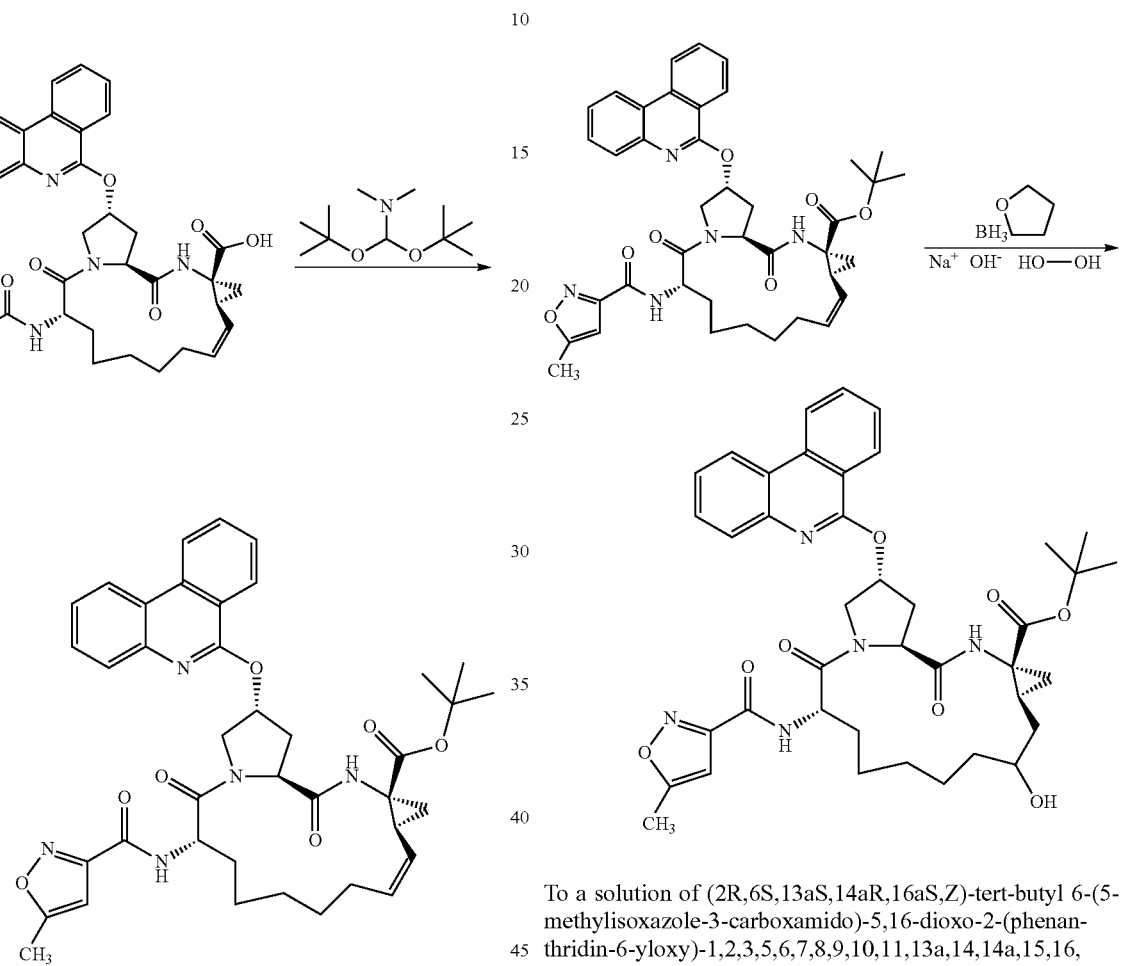

To a solution of (2R,6S,13aS,14aR,16aS,Z)-6-(5-methyl-isoxazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (Example 18d, 0.84 g, 1.3 mmol) in toluene (3.8 ml) heated at 85° C. was added 1,1-di-tert-butoxy-N,N-dimethylmethanamine (0.927 ml, 3.87 mmol) dropwise, and the mixture was stirred at 85° C. for 16 hr. The reaction was only 60% complete as shown by LCMS and additional 0.93 mL of 1,1-di-tert-butoxy-N,N-dimethylmethanamine was added in two portions over two hours. The solvent was evaporated and the residue was purified via flash chromatography (1:4 dichloromethane/ethyl acetate) to provide (2R,6S,13aS,14aR,16aS,Z)-tert-butyl 6-(5-methylisoxazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylate (720 mg, 1.02 mmol, 79% yield) as a white solid.

To a solution of (2R,6S,13aS,14aR,16aS,Z)-tert-butyl 6-(5-methylisoxazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo [1,2-a][1,4]diazacyclopentadecine-14a-carboxylate (Example 18e, 720 mg, 1.02 mmol) in tetrahydrofuran (10 mL) stirring at 0° C. was added borane tetrahydrofuran complex (1 M in tetrahydrofuran, 6.10 mL, 6.10 mmol). The ice bath was removed after the addition was complete and the reaction mixture was stirred at rt for 0.5 hr. The mixture was cooled to 0° C. and aqueous sodium hydroxide solution (2.5 M, 6.10 mL, 15.26 mmol) was added followed by hydrogen peroxide solution (2.494 mL, 24.41 mmol). The reaction mixture was stirred at rt for 1 hr. The mixture was then partitioned between ethyl acetate and water, and the organic layer was washed with brine, dried over anhydrous sodium sulfate, filtered, and evaporated under reduced pressure. The solid residue after solvent evaporation was purified via flash chromatography on silica gel (5% methanol/dichloromethane) to give 486 mg of a mixture of products. This material was repurified by by preparative thin layer chromatography (5% methanol/dichloromethane) to provide the title compound (2R,6S,13aS,14aR,16aS)-tert-butyl 12-hydroxy-6-(5-methylisoxazole-3-carboxamido)-5,16-dioxo-2-(phenanthridin-6-yloxy) octadecahydrocyclopropa[e]pyrrolo [1,2-a][1,4]

diazacyclopenta decine-14a-carboxylate (170 mg, 23%) along with the c'-hydroxy isomer (200 mg, 27% yield).

Example 18g (2R,6S,13aS,14aR,16aS)-tert-butyl 6-(5-methylisoxazole-3-carboxamido)-5,12,16-trioxo-2-(phenanthridin-6-yloxy)octadecahydrocyclopropa[e]pyrrolo[1,2-a][1,4]diazacyclopentadecine-14a-carboxylate

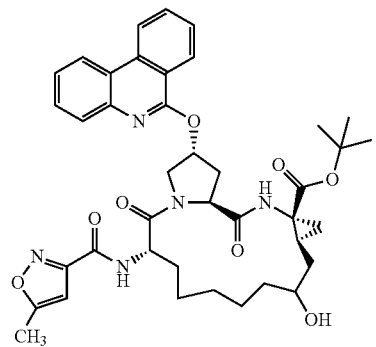

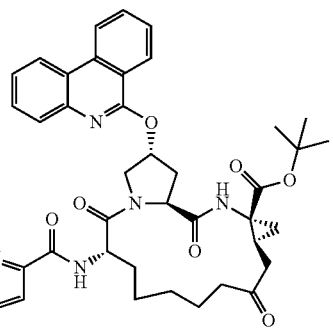

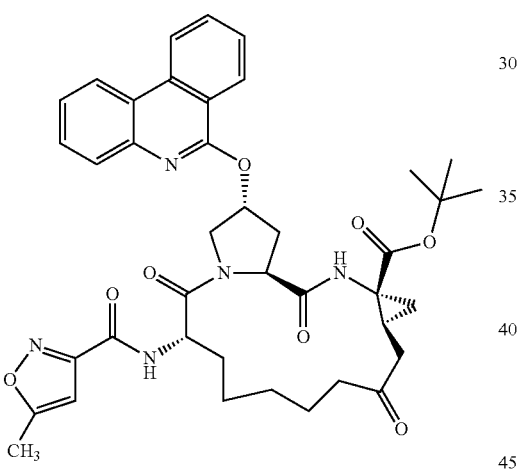

To a solution of oxalyl chloride (0.017 ml, 0.198 mmol) in dichloromethane (0.6 ml) cooled to −60° C. was added DMSO (0.030 ml, 0.419 mmol) dropwise. The mixture was stirred for 15 min and added dropwise a solution of compound (2R,6S,13aS,14aR,16aS)-tert-butyl 12-hydroxy-6-(5-methylisoxazole-3-carboxamido)-5,16-dioxo-2-(phenanthridin-6-yloxy)octadecahydrocyclo propa[e]pyrrolo[1,2-a][1,4]diazacyclopentadecine-14a-carboxylate (Example 18h, 80 mg, 0.11 mmol) in dichloromethane (0.4 ml). The reaction mixture was stirred for 20 min at −60° C., and triethylamine (0.123 ml, 0.882 mmol) was added dropwise. The mixture was stirred at −60° C. for 5 min, and allowed to warm to room temperature with stirring for 10 min. The reaction mixture was quenched with water, stirred for 15 min, and diluted with dichloromethane. The organic layer was separated, dried over anhydrous sodium sulfate, filtered, and evaporated under reduced pressure to give a foamy material. The crude product was purified by flash chromatography on silica gel (5% methanol/dichloromethane) to provide the title compound (2R,6S,13aS,14aR,16aS)-tert-butyl 6-(5-methylisoxazole-3-carboxamido)-5, 12, 16-trioxo-2-(phenanthridin-6-yloxy)octadecahydrocyclopropa[e]pyrrolo [1,2-a][1,4]diazacyclopentadecine-14a-carboxylate (47 mg, 59% yield).

Example 18h (2R,6S,13aS,14aR,16aS)-tert-butyl 12,12-difluoro-6-(5-methylisoxazole-3-carboxamido)-5,16-dioxo-2-(phenanthridin-6-yloxy)octadecahydrocyclopropa[e]pyrrolo[1,2-a][1,4]diazacyclopentadecine-14a-carboxylate

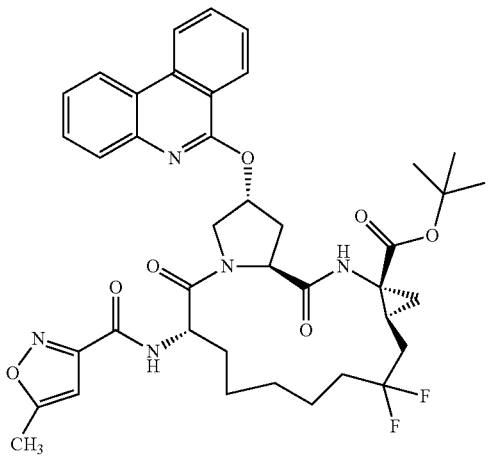

A solution of (2R,6S,13aS,14aR,16aS)-tert-butyl 6-(5-methylisoxazole-3-carboxamido)-5, 12, 16-trioxo-2-(phenanthridin-6-yloxy)octadecahydrocyclopropa[e]pyrrolo[1,2-a][1,4] diazacyclopentadecine-14a-carboxylate (Example 18g, 47 mg, 0.065 mmol) in Morpho-DAST (317 µl, 2.60 mmol) was stirred at rt for 40 h. The resulting mixture was dissolved in 1 mL dichloromethane and added dropwise to a cooled solution of saturated aqueous sodium carbonate. The mixture was stirred for 10 min and extracted with dichloromethane. The organic layer was separated, dried over anhydrous sodium sulfate, filtered, and evaporated under reduced pressure. The crude material was purified by preparative thin layer chromatography (3% methanol/dichloromethane) to provide the title compound (2R,6S,13aS,14aR,16aS)-tert-butyl 12,12-difluoro-6-(5-methylisoxazole-3-carboxamido)-5,16-dioxo-2-

(phenanthridin-6-yloxy)octadecahydrocyclopropa[e]pyrrolo[1,2-a][1,4]diazacyclopentadecine-14a-carboxylate (20 mg, 41% yield) as a white solid.

Example 18i (2R,6S,13aS,14aR,16aS)-12,12-difluoro-6-(5-methylisoxazole-3-carboxamido)-5,16-dioxo-2-(phenanthridin-6-yloxy)octadecahydrocyclopropa[e]pyrrolo[1,2-a][1,4]diazacyclopentadecine-14a-carboxylic acid

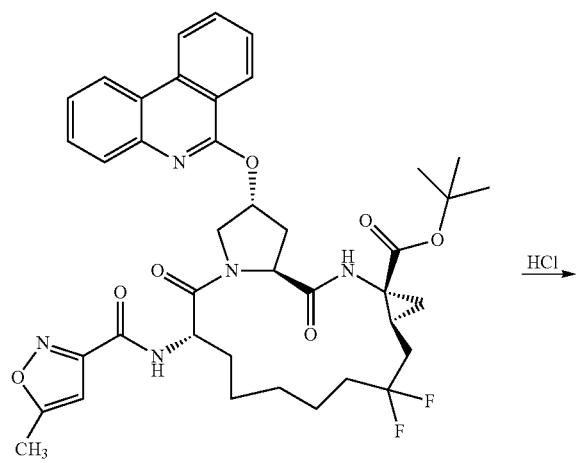

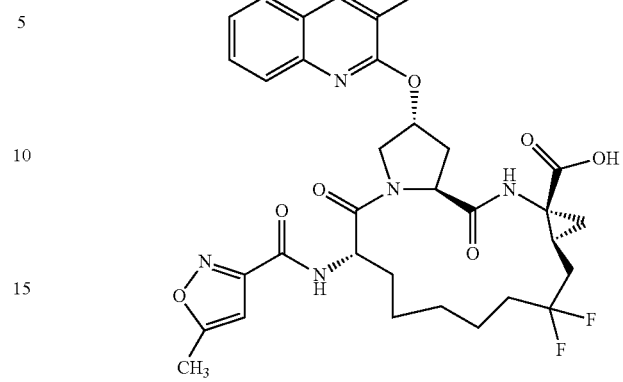

To a solution of (2R,6S,13aS,14aR,16aS)-tert-butyl 12,12-difluoro-6-(5-methylisoxazole-3-carboxamido)-5,16-dioxo-2-(phenanthridin-6-yloxy)octadecahydrocyclopropa[e]pyrrolo[1,2-a][1,4]diazacyclopentadecine-14a-carboxylate (Example 18h, 20 mg, 0.027 mmol) in ethyl acetate (100 μl) stiffing at rt was added 4N hydrogen chloride (134 μl, 0.536 mmol) in dioxane. The reaction mixture was stirred for 24 h, and the solvent was evaporated under reduced pressure. The residue was purified by preparative thin layer chromatography (10% methanol/dichloromethane) to provide the title compound (2R,6S,13aS,14aR,16aS)-12,12-difluoro-6-(5-methylisoxazole-3-carboxamido)-5,16-dioxo-2-(phenanthridin-6-yloxy)octadecahydrocyclopropa[e]pyrrolo [1,2-a][1,4]diazacyclopentadecine-14a-carboxylic (10.2 mg, 55%)

Example 18

N-((2R,6S,13aS,14aR,16aS)-14a-(cyclopropylsulfonylcarbamoyl)-12,12-difluoro-5,16-dioxo-2-(phenanthridin-6-yloxy)octadecahydrocyclopropa[e]pyrrolo [1,2-a][1,4]diazacyclopentadecin-6-yl)-5-methylisoxazole-3-carboxamide

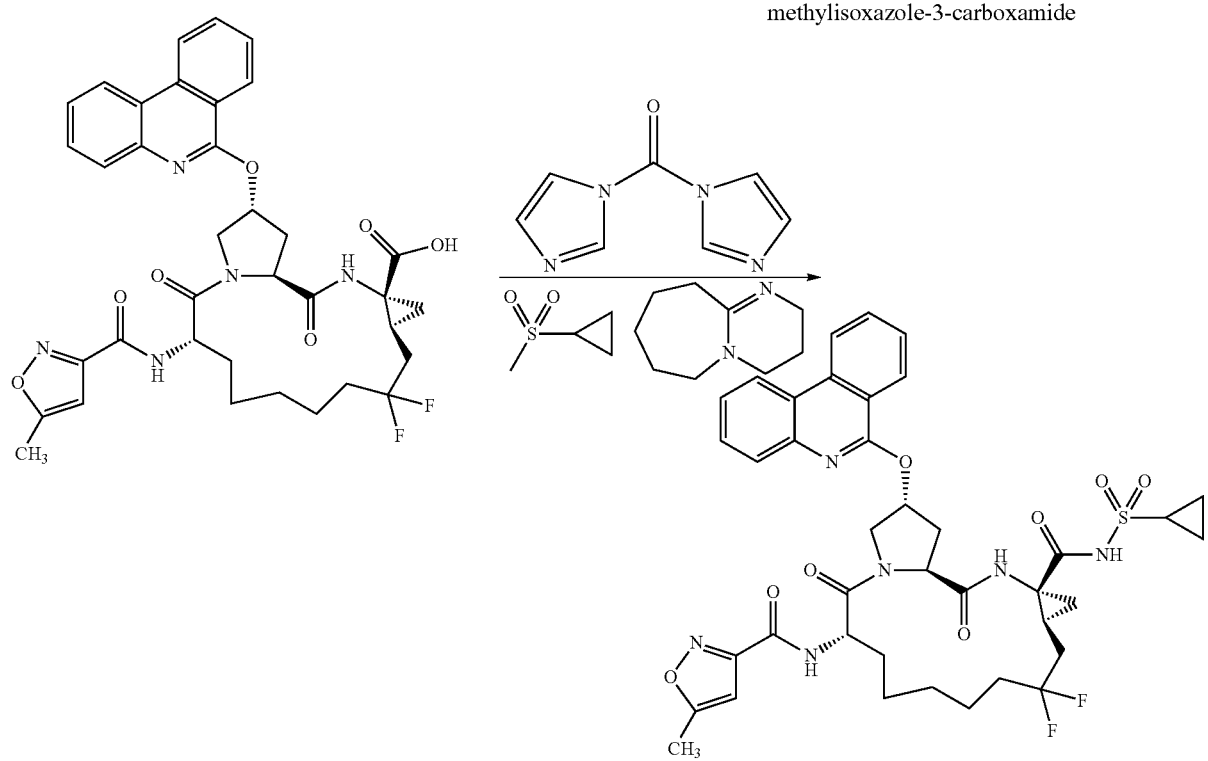

A solution of (2R,6S,13aS,14aR,16aS)-12,12-difluoro-6-(5-methylisoxazole-3-carboxamido)-5,16-dioxo-2-(phenanthridin-6-yloxy)octadecahydrocyclopropa[e]pyrrolo[1,2-a][1,4]diazacyclo pentadecine-14a-carboxylic acid (Example 18i, 21 mg, 0.030 mmol) and di(1H-imidazol-1-yl)methanone (10.96 mg, 0.068 mmol) in dichloroethane (400 μl) was stirred for 2 hr at 42° C. To this mixture was added methylsulfonylcyclopropane (11.0 mg, 0.091 mmol) and 2,3,4,6,7,8,9,10-octahydropyrimido[1,2-a]azepine (13.8 μl, 0.091 mmol) and the reaction mixture was stirred for 2 h at 42° C. The reaction mixture was diluted with ethyl acetate (7 mL) and washed with 10 mL of 1 N HCl followed by saturated aqueous sodium chloride solution. The organic layer was dried over anhydrous sodium sulfate, filtered, and evaporated under reduced pressure. The resulting residue was purified by flash chromatography on silica gel (3% methanol/dichloromethane). The resulting material was further purified by reverse phase HPLC (40% acetonitrile/water with 0.1%TFA to 100% water) to provide the title compound N-((2R,6S,13aS,14aR,16aS)-14a-(cyclopropylsulfonylcarbamoyl)-12,12-difluoro-5,16-dioxo-2-(phenanthridin-6-yloxy)octadecahydrocyclopropa[e]pyrrolo [1,2-a][1,4]diazacyclopentadecin-6-yl)-5-methylisoxazole-3-carboxamide (16 mg, 66.3% yield). MS (ESI): m/z=793.1 [M+H], 791.0 [M−H].

Example 18 provided a HLM stability value of between 50 and 100 μl/min/mg; an EC$_{50}$ of <1.0 nM in a replicon cell line assay in a 1a-H77 background, and an EC$_{50}$ of <1.0 nM in a replicon cell line assay in a 1-con1 background.

Example 19 tert-butyl (2R,6S,13aS,14aR,16aS)-14a-(cyclopropylsulfonylcarbamoyl)-12,12-difluoro-5,16-dioxo-2-(phenanthridin-6-yloxy)octadecahydrocyclopropa[e]pyrrolo[1,2-a][1,4]diazacyclopentadecin-6-ylcarbamate

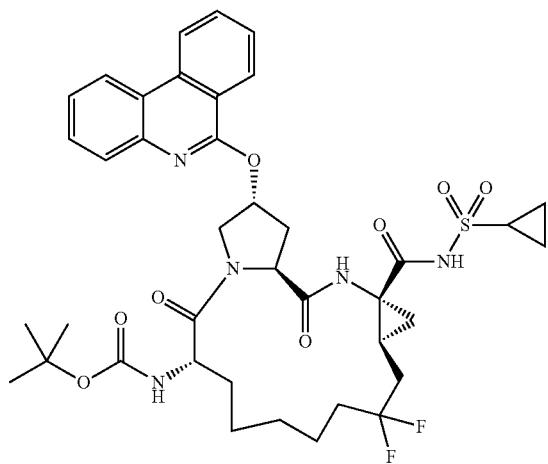 [SMILES: CC(C)(C)OC(=O)N[C@H]1CCCCCC(F)(F)C[C@@H]2C[C@@]2(C(=O)NS(=O)(=O)C2CC2)NC(=O)[C@@H]2C[C@@H](Oc3nc4ccccc4c4ccccc34)CN2C1=O]

Example 19a (2R,6S,13aS,14aR,16aS)-ethyl 6-(tert-butoxycarbonylamino)-12-hydroxy-5,16-dioxo-2-(phenanthridin-6-yloxy)octadecahydrocyclopropa[e]pyrrolo[1,2-a][1,4]diazacyclopentadecine-14a-carboxylate

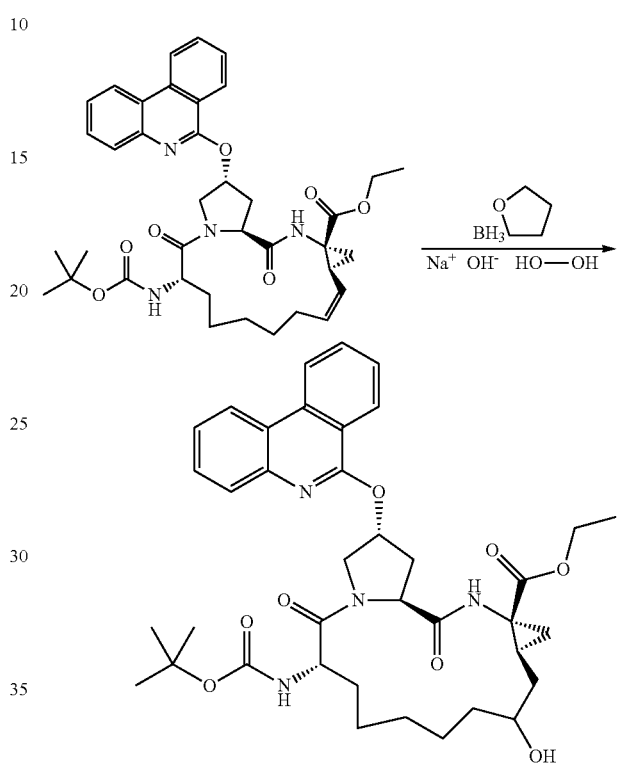

To a solution of (2R,6S,13aS,14aR,16aS,Z)-ethyl 6-(tert-butoxycarbonylamino)-5,16-dioxo-2-(phenanthridin-6-yloxy)-1,2,3,5,6,7,8,9,10,11,13a,14,14a,15,16,16a-hexadecahydrocyclopropa[e]pyrrolo [1,2-a][1,4]diazacyclopentadecine-14a-carboxylate (Example 18a, 3.2 g, 4.77 mmol) in tetrahydrofuran (41.5 ml) at rt with a water bath was added dropwise borane tetrahydrofuran complex (1 M in tetrahydrofuran, 14.3 ml, 14.3 mmol) and stirred at room temperature for 1 h. The mixture was cooled to 0° C. and sodium hydroxide (11.5 ml, 28.6 mmol) was added dropwise followed by hydrogen peroxide (4.0 ml, 43 mmol), and the reaction mixture stirred for 1.5 h at 0° C. The mixture was diluted with ethyl acetate and water, and the organic layer was washed with saturated aqueous sodium chloride solution. The resulting solid was purified via flash chromatography on silica gel (5% methanol in dichloromethane) to provide the title compound (2R,6S,13aS,14aR,16aS)-ethyl 6-(tert-butoxycarbonylamino)-12-hydroxy-5,16-dioxo-2-(phenanthridin-6-yloxy)octadecahydrocyclopropa[e]pyrrolo[1,2-a][1,4]diazacyclopentadecine-14a-carboxylate (1.06 g, 1.539 mmol, 32.3% yield). The α-hydroxy analog (2R,6S,13R,13aR,14aR,16aS)-ethyl 6-(tert-butoxycarbonylamino)-13-hydroxy-5,16-dioxo-2-(phenanthridin-6-yloxy)octadecahydrocyclopropa[e]pyrrolo [1,2-a][1,4]diazacyclopentadecine-14a-carboxylate (0.7 g, 21% yield) was also isolated.

Example 19b (2R,6S,13aS,14aR,16aS)-ethyl 6-(tert-butoxycarbonylamino)-5, 12, 16-trioxo-2-(phenanthridin-6-yloxy)octadecahydrocyclopropa[e]pyrrolo[1,2-a][1,4]diazacyclopentadecine-14a-carboxylate

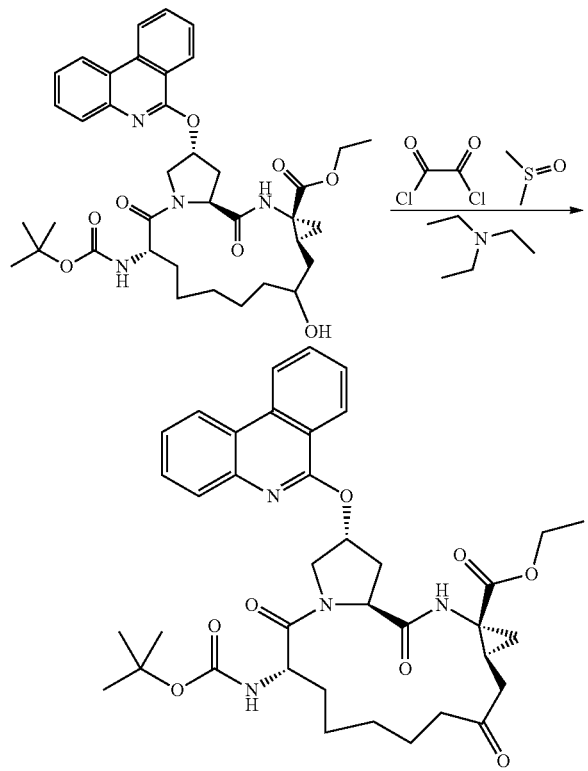

To a solution of oxalyl chloride (0.242 ml, 2.77 mmol) in dichloromethane (5.13 ml) stiffing at −60° C. was added DMSO (0.415 ml, 5.85 mmol) dropwise. The mixture was stirred for 20 min and added dropwise to a solution of (2R, 6S,13aS,14aR,16aS)-ethyl 6-(tert-butoxycarbonylamino)-12-hydroxy-5,16-dioxo-2-(phenanthridin-6-yloxy)octadecahydro cyclopropa[e]pyrrolo[1,2-a][1,4]diazacyclopentadecine-14a-carboxylate (Example 19a, 1.06 g, 1.54 mmol) in dichloromethane (5.13 ml). The reaction mixture was stirred for 20 min -60° C., and triethylamine (1.716 ml, 12.31 mmol) was added. The mixture was stirred for 10 min at -60° C., and then stirred for another 20 min at room temperature. The reaction mixture was quenched with water and stirred for 15 min, and diluted with dichloromethane. The organic layer was separated, dried over anhydrous sodium sulfate, filtered, and evaporated under reduced pressure to give a foamy material. The crude product was purified by flash chromatography on silica gel (5% methanol/dichloromethane). The fractions containing the title compound were collected and rechromatographed on a silica gel column (65% ethyl acetate/hexane) to provide the title compound (2R,6S,13aS,14aR,16aS)-ethyl 6-(tert-butoxycarbonylamino)-5, 12, 16-trioxo-2-(phenanthridin-6-yloxy)octadecahydrocyclopropa[e]pyrrolo [1,2-a][1,4] diazacyclopentadec 14a-carboxylate (680 mg, 64.3% yield) as a white solid.

Example 19c (2R,6S,13aS,14aR,16aS)-ethyl 6-(tert-butoxycarbonylamino)-12,12-difluoro-5,16-dioxo-2-(phenanthridin-6-yloxy)octadecahydrocyclopropa[e]pyrrolo[1,2-a][1,4]diazacyclopentadecine-14a-carboxylate

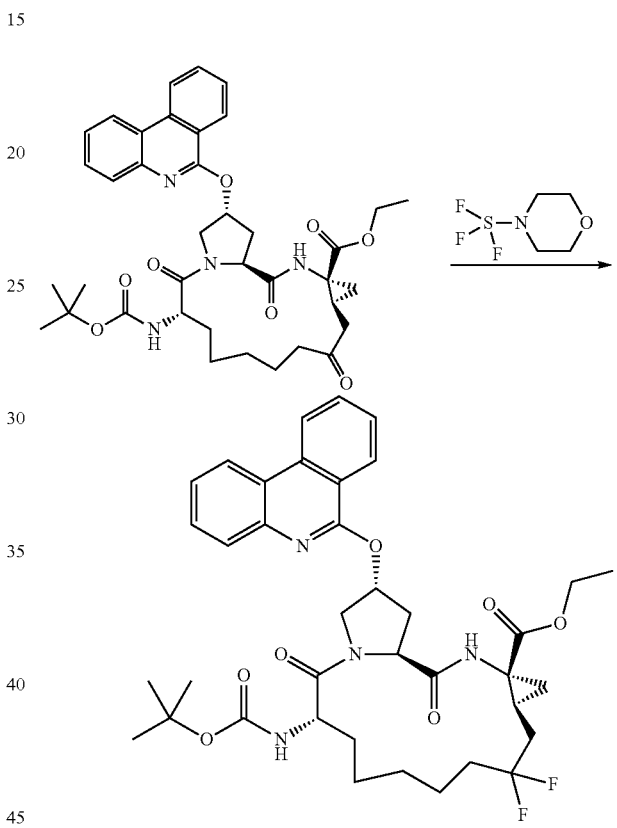

A solution of (2R,6S,13aS,14aR,16aS)-ethyl 6-(tert-butoxycarbonylamino)-5, 12, 16-trioxo-2-(phenanthridin-6-yloxy) octadecahydrocyclopropa[e]pyrrolo [1,2-a][1,4]diazacyclopentadecine-14a-carboxylate (Example 19b, 680 mg, 0.990 mmol) in Morpho-DAST (2.4 mL, 20 mmol) was stirred at room temperature for 48 h. The reaction mixture was dissolved in 2 mL dichloromethane and added dropwise into a cooled solution of saturated aqueous sodium carbonate solution, stirred for 10 min, and extracted with dichloromethane. The organic layer was dried over anhydrous sodium sulfate, filtered, and evaporated under reduced pressure. The residue was purified by preparative thin layer chromatography on silica gel (3% methanol/dichloromethane) to provide the title compound (2R,6S,13aS,14aR,16aS)-ethyl 6-(tert-butoxycarbonylamino)-12,12-difluoro-5,16-dioxo-2-(phenanthridin-6-yloxy)octadecahydro cyclopropa[e]pyrrolo[1,2-a][1,4]diazacyclopentadecine-14a-carboxylate (320 mg, 45.6% yield) as a white solid.

Example 19d (2R,6S,13aS,14aR,16aS)-6-(tert-butoxycarbonylamino)-12,12-difluoro-5,16-dioxo-2-(phenanthridin-6-yloxy)octadecahydrocyclopropa[e]pyrrolo[1,2-a][1,4]diazacyclopentadecine-14a-carboxylic acid

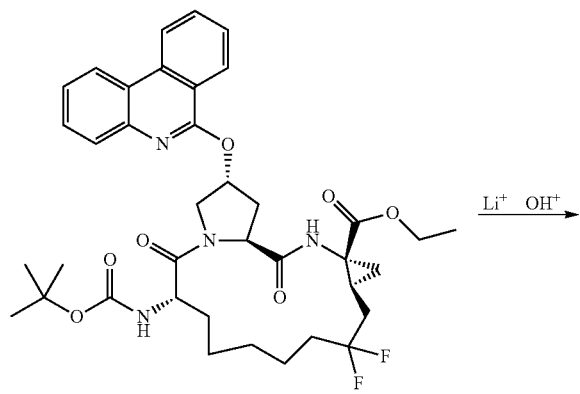

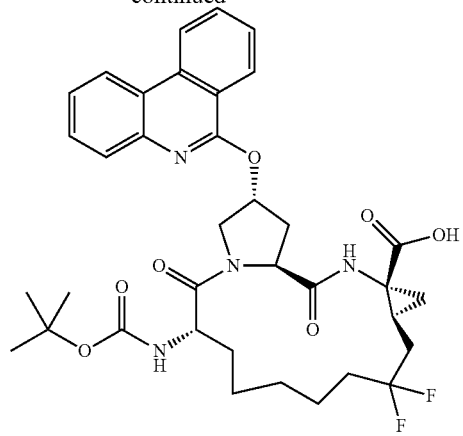

To a solution of (2R,6S,13aS,14aR,16aS)-ethyl 6-(tert-butoxycarbonylamino)-12,12-difluoro-5,16-dioxo-2-(phenanthridin-6-yloxy)octadecahydrocyclopropa[e]pyrrolo [1,2-a][1,4]diazacyclo pentadecine-14a-carboxylate (Example 19c, 320 mg, 0.451 mmol) in tetrahydrofuran (1505 µl), water (752 µl), and ethanol (752 µl) was added lithium hydroxide monohydrate (123 mg, 2.93 mmol) at room temperature The mixture was stirred at room temperature for 16 h and then heated at 37° C. for 6h. The mixture was cooled to room temperature and then eluted through a pad of silica gel with 10% methanol/dichloromethane, and evaporated under reduced pressure. The crude materal was purified by flash chromatography on silica gel (10% methanol/dichloromethane) to provide the title compound (2R,6S,13aS,14aR,16aS)-6-(tert-butoxycarbonylamino)-12,12-difluoro-5,16-dioxo-2-(phenanthridin-6-yloxy)octadeca hydrocyclopropa[e]pyrrolo[1,2-a][1,4]diazacyclopentadecine-14a-carboxylic acid (215 mg, 70.0% yield) as a white solid.

Example 19

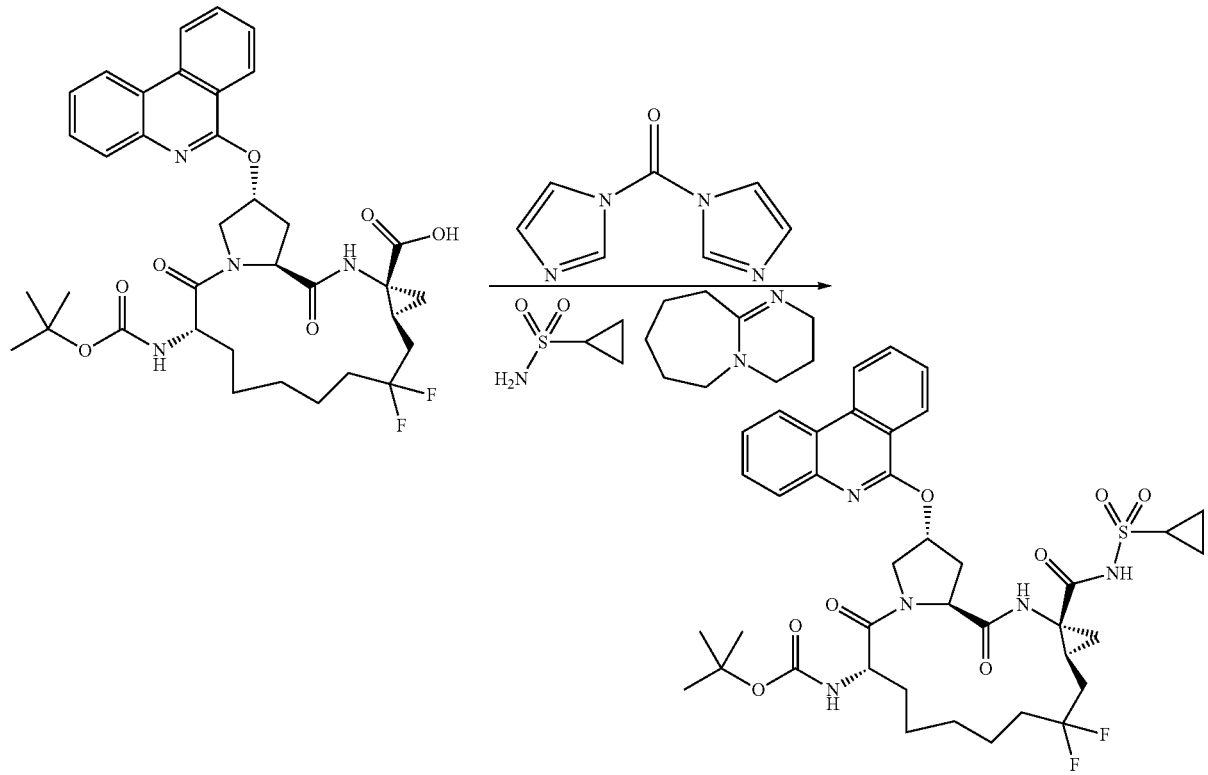

A solution of (2R,6S,13aS,14aR,16aS)-6-(tert-butoxycarbonylamino)-12,12-difluoro-5,16-dioxo-2-(phenanthridin-6-yloxy)octadecahydrocyclopropa[e]pyrrolo [1,2-a][1,4]diazacyclopentadecine-14a-carboxylic acid (215 mg, 0.316 mmol) and di(1H-imidazol-1-yl)methanone (Example 19d, 114 mg, 0.701 mmol) in dichloroethane (2 mL) was stirred for 2 h at room temperature. To this mixture was added cyclopropanesulfonamide (115 mg, 0.948 mmol) and 2,3,4,6,7,8,9,10-octahydropyrimido[1,2-a]azepine (0.143 mL, 0.948 mmol, dried with 4 A sieves powder at 42° C. for 2 h prior to usage), and the solution was stirred for 2 h. The reaction mixture was diluted with ethyl acetate (7 mL) and washed with 10 mL of 0.1 N HCl followed by saturated aqueous sodium chloride solution. The organic layer was dried with anhydrous sodium sulfate, filtered, and evaporated under reduced pressure leaving 0.23 g crude solid which was purified via flash chromatography on silica gel (3% methanol/dichloromethane) to provide the title compound tert-butyl (2R,6S,13aS,14aR,16aS)-14a-(cyclopropylsulfonylcarbamoyl)-12,12-difluoro-5,16-dioxo-2-(phenanthridin-6-yloxy)octadecahydrocyclopropa[e]pyrrolo [1,2-a][1,4]diazacyclopentadecin-6-ylcarbamate (195 mg, 0.249 mmol, 79% yield). MS (ESI): m/z=784.1 [M+H]. Example 19 provided an $IC_{50}$ of <0.1 nM in a 1a enzyme assay; an $IC_{50}$ of <0.1 0 nM in a 1b enzyme assay; a HLM stability value of >100 μl/min/mg; an $EC_{50}$ of <1.0 nM in a replicon cell line assay in a 1a-H77 background, and an $EC_{50}$ of <1.0 nM in a replicon cell line assay in a 1-con1 background.

Example 20

(2R,6S,13aS,14aR,16a5)-N-(cyclopropylsulfonyl)-12,12-difluoro-6-(5-methylpyrazine-2-carboxamido)-5,16-dioxo-2-(phenanthridin-6-yloxy)octadecahydrocyclopropa[e]pyrrolo[1,2-a][1,4]diazacyclopentadecine-14a-carboxamide

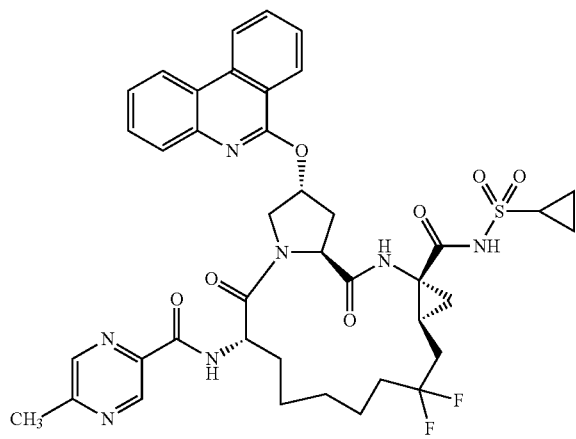 [SMILES: Cc1cnc(C(=O)N[C@H]2CCCCCC(F)(F)C[C@@H]3C[C@@]3(C(=O)NS(=O)(=O)C3CC3)NC(=O)[C@@H]3C[C@@H](Oc4nc5ccccc5c5ccccc45)CN3C2=O)cn1]

Example 20a (2R,6S,13aS,14aR,16aS)-6-amino-N-(cyclopropylsulfonyl)-12,12-difluoro-5,16-dioxo-2-(phenanthridin-6-yloxy)octadecahydrocyclopropa[e]pyrrolo [1,2-a][1,4]diazacyclopenta decine-14a-carboxamide

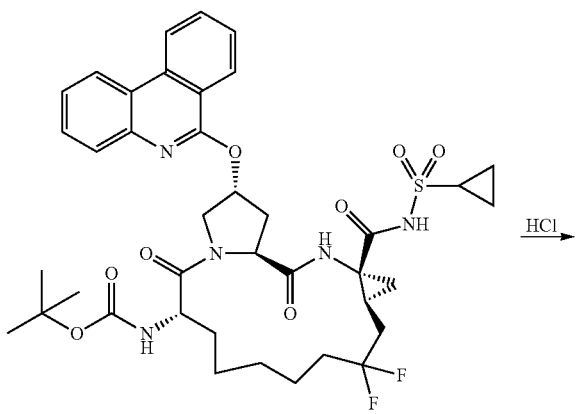

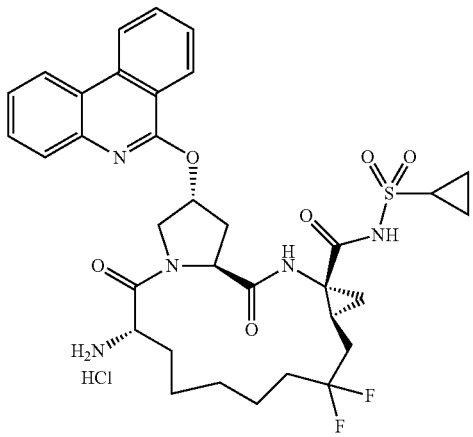

To a solution of tert-butyl (2R,6S,13aS,14aR,16aS)-14a-(cyclopropylsulfonylcarbamoyl)-12,12-difluoro-5,16-dioxo-2-(phenanthridin-6-yloxy)octadecahydrocyclopropa[e]pyrrolo [1,2-a][1,4]diazacyclopentadecin-6-ylcarbamate (Example 19, 195 mg, 0.249 mmol) in ethyl acetate (1 mL) stiffing at room temperature was added 4 N hydrogen chloride (1.24 mL, 5.0 mmol) in dioxane. The reaction mixture was stirred for 4 h, and then the solvent was evaporated under reduced pressure. The residue was triturated with ethyl acetate and the product was filtered as a white solid. The solid was dissolved in methanol and the solvent was evaporated to provide the title compound (2R,6S,13aS,14aR,16aS)-6-amino-N-(cyclopropylsulfonyl)-12,12-difluoro-5,16-dioxo-2-(phenanthridin-6-yloxy)octadecahydrocyclopropa[e]pyrrolo[1,2-a][1,4]diazacyclopentadecine-14a-carboxamide, Hydrochloric Acid (178 mg, 0.247 mmol, 99% yield).

Example 20

(2R,6S,13aS,14aR,16aS)-N-(cyclopropylsulfonyl)-12,12-difluoro-6-(5-methylpyrazine-2-carboxamido)-5,16-dioxo-2-(phenanthridin-6-yloxy)octadecahydrocyclopropa[e]pyrrolo[1,2-a][1,4]diazacyclopentadecine-14a-carboxamide

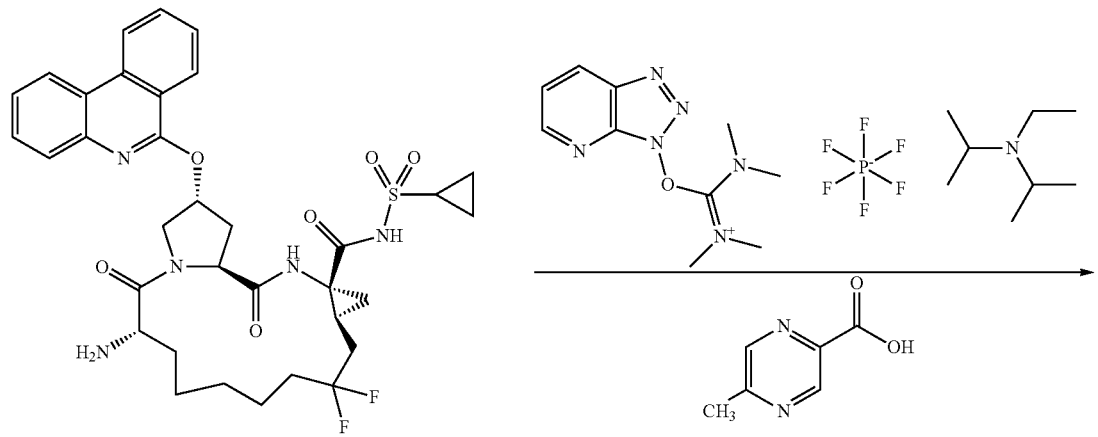

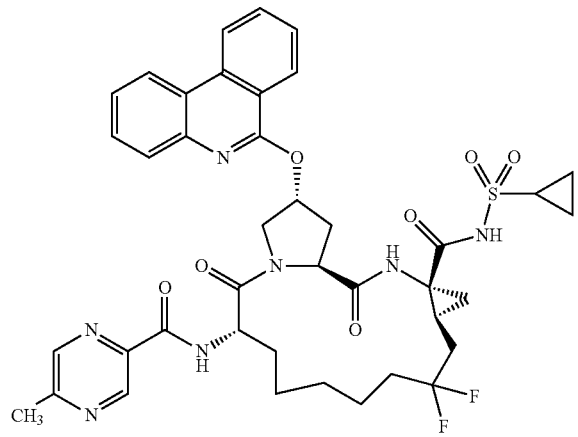

To a mixture of a(2R,6S,13aS,14aR,16aS)-6-amino-N-(cyclopropylsulfonyl)-12,12-difluoro-5,16-dioxo-2-(phenanthridin-6-yloxy)octadecahydrocyclopropa[e]pyrrolo[1,2-a][1,4]diazacyclopentadecine-14a-carboxamide, Hydrochloric Acid (Example 20a, 12 mg, 0.017 mmol), 5-methylpyrazine-2-carboxylic acid (2.53 mg, 0.018 mmol) and 2-(3H-[1,2,3]triazolo[4,5-b]pyridin-3-yl)-1,1,3,3-tetramethylisouronium hexafluorophosphate(V) (7.0 mg, 0.018 mmol) in dichloromethane (167 µl) was added N-ethyl-N-isopropylpropan-2-amine (10.18 µl, 0.058 mmol), and the resulting mixture was stirred for 3 h at room temperature. 0.1 N HCl was added and the organic layer was separated, dried over anhydrous sodium sulfate, and filtered. The residue after solvent evaporation was eluted through silica gel with 10% acetone/dichloromethane. The fractions containing the title compound were combined and the resulting crude material was purified by preparative thin layer chromatography on silica gel (20:1 dichloromethane/methanol) to provide the title compound (2R,6S,13aS,14aR,16aS)-N-(cyclopropylsulfonyl)-12,12-difluoro-6-(5-methylpyrazine-2-carboxamido)-5,16-dioxo-2-(phenanthridin-6-yloxy)octadecahydrocyclopropa[e]pyrrolo[1,2-a][1,4]diazacyclopentadec 14a-carboxamide (8 mg, 60% yield) as a white solid. MS (ESI): m/z=804.1 [M+H]. Example 20 provided a HLM stability value of <50 µl/min/mg; an $EC_{50}$ of between 2.0 and 5.0 nM in a replicon cell line assay in a 1a-H77 background, and an $EC_{50}$ of between 1.0 and 2.0 nM in a replicon cell line assay in a 1-con1 background.

Example 21

(2R,6S,13aS,14aR,16a5)-N-(cyclopropylsulfonyl)-6-(1,5-dimethyl-1H-pyrazole-3-carboxamido)-12,12-difluoro-5,16-dioxo-2-(phenanthridin-6-yloxy)octadecahydrocyclopropa[e]pyrrolo[1,2-a][1,4]diazacyclopentadecine-14a-carboxamide

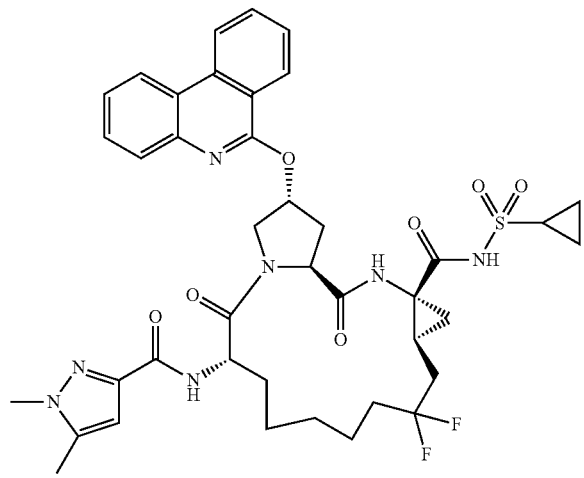 [SMILES: Cc1cc(C(=O)N[C@H]2CCCCCC(F)(F)C[C@@H]3C[C@@]3(C(=O)NS(=O)(=O)C3CC3)NC(=O)[C@@H]3C[C@@H](Oc4nc5ccccc5c5ccccc45)CN3C2=O)nn1C]

To a mixture of (2R,6S,13aS,14aR,16aS)-6-amino-N-(cyclopropylsulfonyl)-12,12-difluoro-5,16-dioxo-2-(phenanthridin-6-yloxy)octadecahydrocyclopropa[e]pyrrolo[1,2-a][1,4]diazacyclopentadecine-14a-carboxamide, Hydrochloric Acid (Example 20a, 12 mg, 0.017 mmol), 1,5-dimethyl-1H-pyrazole-3-carboxylic acid (2.57 mg, 0.018 mmol) and 2-(3H-[1,2,3]triazolo [4,5-b]pyridin-3-yl)-1,1,3,3-tetramethylisouronium hexafluorophosphate(V) (7.0 mg, 0.018 mmol)in dichloromethane (167 µl) was added N-ethyl-N-isopropylpropan-2-amine (10.18 µl, 0.058 mmol) and the mixture was stirred for 3 h at room temperature. 0.1 N HCl was added and organic layer was separated, dried over anhydrous sodium sulfate, and filtered. The residue after solvent evaporation under reduced pressure was eluted through silica gel with 10% acetone/dichloromethane. The fractions containing the title compound were combined and the resulting crude material was purified by preparative thin layer chromatography on silica gel (20:1 dichloromethane/methanol) to provide the title compound (2R,6S,13aS,14aR,16aS)-N-(cyclopropylsulfonyl)-6-(1,5-dimethyl-1H-pyrazole-3-carboxamido)-12,12-difluoro-5,16-dioxo-2-(phenanthridin-6-yloxy)octadecahydrocyclopropa[e]pyrrolo [1,2-a][1,4] diazacyclopentadecine-14a-carboxamide (8 mg 60% yield) as a white solid. MS (ESI): m/z=806.1 [M+H]. Example 21 provided a HLM stability value of <50 µl/min/mg; an $EC_{50}$ of between 2.0 and 5.0 nM in a replicon cell line assay in a 1a-H77 background, and an $EC_{50}$ of <1.0 nM in a replicon cell line assay in a 1b-con1 background.

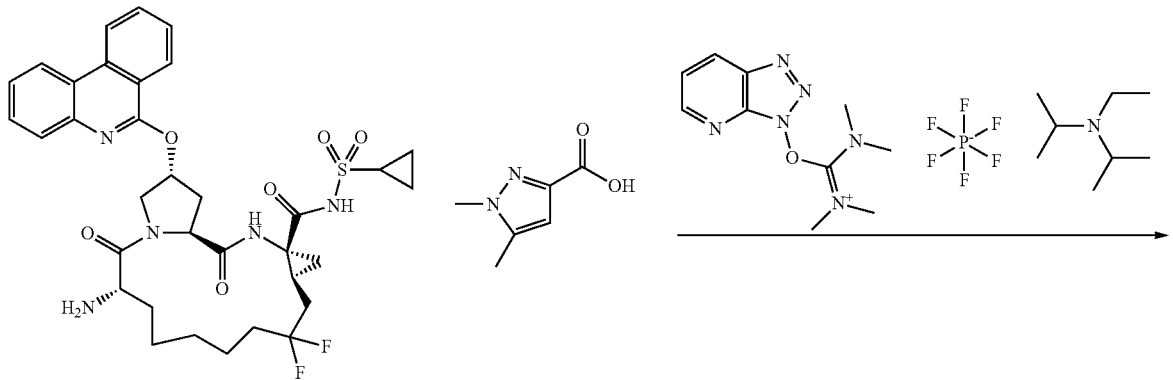

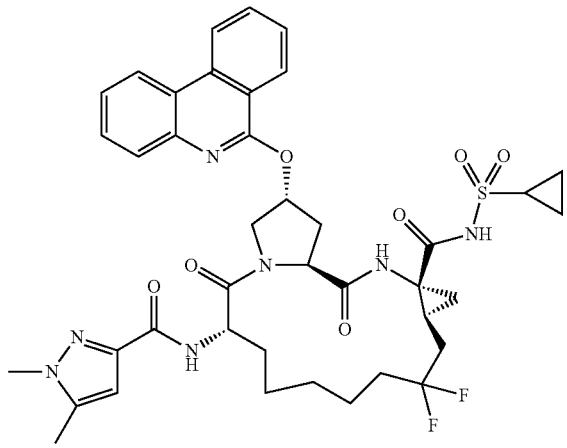

Example 22

Measurement of Potency of Inhibition with Purified NS3 Protease Enzyme

The activity of recombinant HCV NS3 proteases derived from isolates representing genotypes 1, 2, 3 or 4 is measured by cleavage of the following peptide substrate:

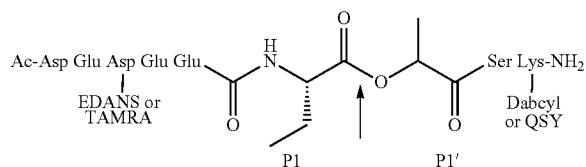

The substrate is labeled with a fluor and a fluorescence quencher. Cleavage results in release of the quencher and an increase in fluorescence. NS3 protease is incubated with a dilution series of inhibitor in 150 mM NaCl, 10% Glycerol, 5 mM DTT, with or without 0.01% dodecyl maltoside for either 30 minutes or 300 minutes. Substrate is added at a concentration of 5 uM to initiate the reaction, and fluorescence is measured at 2 minute intervals for 30 minutes. Enzyme concentrations range from 10 to 100 nM in the absence of detergent, or 10-fold lower in the presence of detergent. Substrate peptides are labeled with either EDANS and DABCYL (excitation 355 nm, emission 485 nm) or TAMRA and QSY (excitation 544 nm, emission 590 nm). For routine IC50 determination, 3-fold serial dilutions starting with initial concentrations of 100 µM, 200 µM, or 2 mM are used. For compounds with $K_i$ values approaching or lower than the enzyme concentration, a tight-binding calculation format is used, with 24 dilutions of inhibitor covering a range of 0 to 100 nM inhibitor. $K_i$ values are calculated using the tight binding assay format, according to the following equation:

$$V = A\{[(K+I-E)^2 + 4KE])^{1/2} - (K+I-E)\}, \text{ where } I = \text{total inhibitor concentration}, E = \text{active enzyme concentration}, K = \text{apparent } K_i \text{ value and } A = [k_{cat})S/2] [K_m = (S)].$$

Replicon Cell Lines

Two subgenomic replicon cell lines can be used for compound characterization in cell culture: one derived from genotype 1a and one derived from genotype 1b. Both replicon constructs are bicistronic subgenomic replicons essentially similar to those described by Bartenschlager and coworkers (Lohmann et al., Science (1999) 285(5424):110-113). The genotype 1a replicon construct contains the NS3-NS5B coding region derived from the H77 strain of HCV (1a-H77) (Blight et al., J Virol (2003) 77(5):3181-3190). The first cistron of the construct consists of the first 36 nucleotides of the HCV 1a-H77 core gene fused to a firefly luciferase reporter and a neomycin phosphotransferase (Neo) selectable marker. The luciferase and Neo coding regions are separated by the FMDV 2a protease. The second cistron contains the NS3-NS5B coding region derived from 1a-H77 with the addition of adaptive mutations E1202G in NS3, K1691R in NS4A, and K2040R and S2204I in NS5A. The 1b-Con-1 replicon construct is identical to the 1a-H77 replicon, except that the 5' and 3' NTRs and the NS3-NS5B coding region can be derived from the 1b-Con-1 strain (Blight et al., Science (2000) 290 (5498):1972-1974), and the adaptive mutations are E1202G and T1280I in NS3 and S2204I in NS5A.

Replicon Compound Testing

Replicon cell lines can be maintained in Dulbecco's modified Eagles medium (DMEM) containing 100 IU/ml penicillin, 100 mg/ml streptomycin (Invitrogen), 200 mg/ml G418 (Invitrogen) and 10% (v/v) fetal bovine serum (FBS). Replicon-containing cells can be seeded into 96 well plates at a density of 5000 cells per well in 100 µl DMEM containing 5% FBS. The next day, the compound can be initially diluted in dimethyl sulfoxide (DMSO) to generate a 200× stock of the inhibitor in a series of 8 half-log dilutions. The dilution series can then be diluted 100-fold in the medium containing 5% FBS. One hundred microliters of medium with the inhibitor can be added to each well of the overnight cell culture plate already containing 100 of DMEM with 5% FBS. In assays where the protein binding effect on inhibitor potency is assessed, the medium from the overnight cell culture plates can be replaced with 200 µl DMEM containing 40% human plasma (Innovative Research) plus 5% FBS as well as compound. The cells can be grown for 4 days in tissue culture incubators. The inhibitory effects of compounds against the replicons can be determined by measuring either the level of luciferase or HCV RNA. The luciferase assay can be conducted using a Luciferase Assay System kit (Promega) following the manufacturer's instructions. Briefly, the cell culture medium is removed and wells are washed with 200 µl of phosphate-buffered saline. To each well Passive Lysis buffer (Promega, Wis.) is added and the plates are incubated for 30 min with rocking to lyse the cells. Luciferin solution (50 µl, Promega) is added, and luciferase activity is measured with a Victor II luminometer (Perkin-Elmer). To determine HCV RNA levels, RNA extractions can be performed using the CellsDirect kit (Invitrogen), and the HCV RNA copy number can be measured using the SuperScript III Platinum One-Step qRT-PCR system (Invitrogen) and primers specific to the HCV 5' nontranslated region. Cytotoxicity can be determined by the 3-[4,5-dimethythiazol-2-yl]-2,5-diphenyltetrazolium bromide (MTT) colorimetric assay as follows. Replicon cells is plated in 96-well plates (4000 cells per well), the next day compound dilutions are added as in the activity assay, and the cells are grown in the presence of the inhibitors for 4 days. The MTT solution is diluted in DMEM containing 5% FBS and 60 µl of the solution is added to the cells. After 4 hrs, the cells are solubilized by the addition of 30 µl SDS (20% in 0.02 N HCl). The plates are incubated overnight and the optical density can be measured at 570 nm. To determine compounds' $EC_{50}$ and $TD_{50}$, luciferase, RNA inhibition and MTT data can be analyzed using the GraphPad Prism 4 software (equation: sigmoidal dose-response—variable slope).

Mutants in Transient Replicons

Mutations detected in resistance selection studies can be introduced into wild type transient replicon constructs based on genotypes 1a-H77 and 1-N. Both replicons are bicistronic sub-genomic constructs containing a firefly luciferase reporter similar to those described above, but they do not contain a Neo selectable marker and are therefore only suitable for transient replication assays. The 1a-H77 replicon for transient assays further differs from the replicon in the stable cell line in that it contains NS2 through NS5B in the second cistron. The 1-N strain replicon contains NS3 through NS5B in the second cistron, with adaptive mutations E1202G in NS3 and S2204I in NS5A. Mutagenesis can be performed using the Stratagene QuikChange XL II site-directed mutagenesis kit. Mutants' sequences can be confirmed, plasmids can be linearized with Xba I restriction enzyme and used as template for in vitro transcription reactions to make mutant replicon RNA for transient transfections. In vitro transcription can be performed with the T7 Megascript kit (Ambion).

Transient replicon transfections can be performed essentially as described by Mo et al. (*Antimicrob Agents Chemother* (2005) 49(10):4305-4314) with slight modifications. Fifteen micrograms of template RNA can be used to electroporate $3 \times 10^6$ cells in a 200 μl volume in a 0.2 cm cuvette. The cells used for transient transfections can be Huh7 cells obtained by curing replicon-containing cells with IFN (Mo et al., supra). Electroporation can be done with a Gene Pulser II (Bio-Rad, CA) at 480V and 25 μF, using two manual pulses. Transfected cells can be diluted to $7.5 \times 10^4$ cells/ml and plated in 96 well plates at $7.5 \times 10^3$ cells per well in DMEM with 5% FBS and 100 IU/ml penicillin, 100 mg/ml streptomycin (Invitrogen). Four hours post-transfection, one plate is harvested for luciferase measurement; this plate may provide a measure of the amount of input RNA that can be translated, and thus of transfection efficiency. To the remaining plates, test compound serial dilutions in DMSO can be added (0.5% DMSO final concentration), and plates are incubated for 4 days.

Exemplary compounds of the present invention were tested for their anti-HCV activities. Many of the compounds tested showed unexpected anti-HCV activities, including excellent activities in biochemical assays against HCV proteases representing various HCV genotypes, superior activities in standard HCV replicon assays including activity against 1a-H77 and 1b-con1 HCV strains in the absence or presence of 40% human plasma, and/or excellent activities in transient replicon assays against drug-resistant mutants in a number of different HCV genetic backgrounds.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

Those skilled in the art will recognize, or be able to ascertain using no more than routine experimentation, many equivalents of the specific embodiments of the invention described herein. Such equivalents are intended with be encompassed by the following claims.

What is claimed:

1. A compound of formula I or formula I':

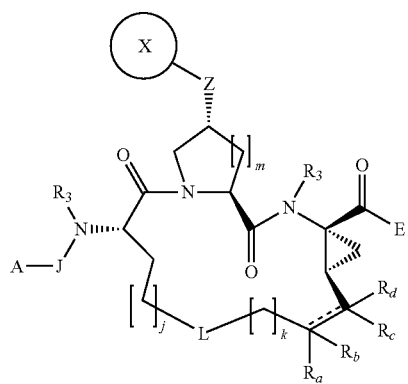

(I)

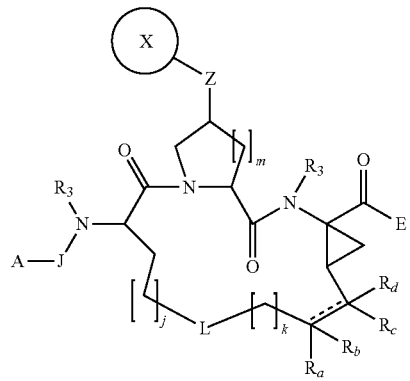

(I')

or a pharmaceutically acceptable salt, hydrate, or solvate thereof,
wherein:
X is

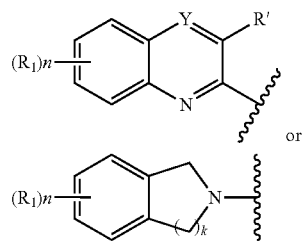

Y is N or —C(R")—;
wherein if Y is —C(R")—, then R' and R" taken together with the carbon atoms to which they are attached form a ring, which is optionally substituted;
R' is H, alkyl, alkenyl, alkynyl, carbocyclic, heterocyclyl, aryl, or heteroaryl, each of which may be optionally substituted;
each $R_1$ is independently selected from halogen, hydroxy, amino, —CN, —CF$_3$, —N$_3$, —NO$_2$, —OR$_4$, —SR$_4$, —SOR$_4$, —SO$_2$R$_4$, —N(R$_3$)S(O)$_2$—R$_4$, —N(R$_3$)(SO$_2$)NR$_3$R$_4$, —NR$_3$R$_4$, —C(O)—OR$_4$, —C(O)R$_4$, —C(O)NR$_3$R$_4$, —N(R$_3$)C(O)R$_4$; optionally substituted aryl; optionally substituted heteroaryl; optionally substituted heterocyclic; optionally substituted carbocyclic; optionally substituted alkyl, optionally substituted haloalkyl, optionally substituted alkenyl, or optionally substituted alkynyl, each containing 0, 1, 2, or 3 heteroatoms selected from O, S, or N;
each n is independently 0, 1, 2, 3, or 4;
Z is O, S(O)$_m$, NR$_x$, OC(O), C(O), C(O)O, NR$_x$C(O), or C(O)NR$_x$;
each R$_x$ is independently H or alkyl;
J is —C(O)—, —O—C(O)—, —C(O)O—, —N(R$_3$)—C(O)—, —C(S)—, —C(=NR$_4$)—, —N(R$_3$)—, —S(O)—, or —S(O$_2$)—or absent;
A is selected from the group consisting of the following:
(i) H, aryl; substituted aryl; heteroaryl; substituted heteroaryl;
(ii) heterocyclyl or substituted heterocyclyl; and
(iii) —C$_1$-C$_8$ alkyl, —C$_2$-C$_8$ alkenyl or —C$_2$-C$_8$ alkynyl, each containing 0, 1, 2, or 3 heteroatoms independently selected from O, S, and N; substituted —C$_1$-C$_8$ alkyl, substituted —C$_2$-C$_8$ alkenyl or substituted —C$_2$-C$_8$ alkynyl, each containing 0, 1, 2, or 3 heteroatoms independently selected from O, S and N; —C$_3$-C$_{12}$ carbocyclic, substituted —C$_3$-C$_{12}$ carbocyclic; —C$_3$-C$_{12}$ cycloalkenyl, or substituted—C$_3$-C$_{12}$cycloalkenyl;

E is —G-R$_5$;

wherein G is absent; optionally substituted alkylene, optionally substituted alkenylene, optionally substituted alkynylene, each containing 0, 1, 2, or 3 heteroatoms selected from O, S, or N;

or —O—, —S—, —N(R$_3$)—, —N(R$_3$)S(O$_p$)—, —N(R$_3$)C(O)—, —N(R$_3$) C(O)S(O$_p$)—, —OS(O$_p$)—, —C(O)S(O$_p$)—, or —C(O)N(R$_3$)S(O$_p$)—;

each p is independently 0, 1, or 2;

R$_5$ is H; optionally substituted alkyl, optionally substituted alkenyl, or optionally substituted alkynyl, each containing 0, 1, 2, or 3 heteroatoms selected from O, S, or N; optionally substituted carbocyclic, optionally substituted heterocyclic, optionally substituted aryl, or optionally substituted heteroaryl;

═══ denotes a carbon-carbon single or double bond (i.e.,

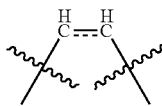

means

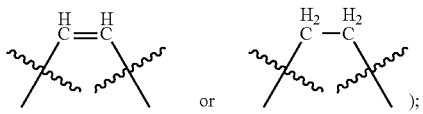

each of R$_a$, R$_b$, R$_c$, and R$_d$ are each independently H or halo, wherein at least two of R$_a$, R$_b$, R$_c$, and R$_d$ are halo; and R$_b$ and R$_d$ are absent if ═══ is a double bond each R$_3$ and R$_4$ is independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; and optionally substituted carbocyclic;

L is absent;

j =independently 0, 1, 2, 3, or 4;

k=independently 0, 1, 2, or 3; and each m is independently 0, 1, or 2.

2. The compound of claim 1, wherein ring X is phenanthridinyl, quinoxalinyl, quinolinyl, or isoindolinyl.

3. The compound of claim 1 according to formula I-A, or a pharmaceutically acceptable salt, hydrate, or solvate thereof, wherein:

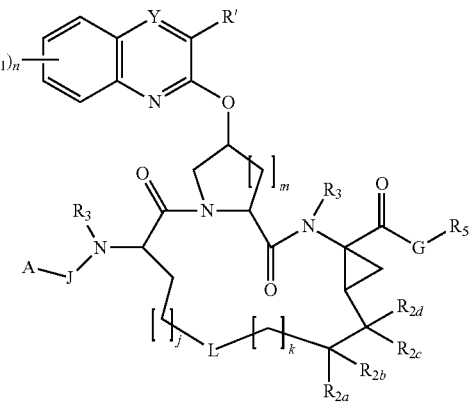

(I-A)

Y is —C(R″)—,

R′ and R″, taken together with the atoms to which each is attached, form a phenyl which is optionally substituted with one or more R$_1$;

m is 1, j is 2, k is 2, L is absent;

J is —C(O)—, —O—C(O)—, —N(R$_3$)—C(O)—, —S(O)—, or —S(O$_2$)—;

A is optionally substituted alkyl, optionally substituted alkenyl, optionally substituted alkynyl, optionally substituted heteroaryl, optionally substituted aryl, optionally substituted heterocyclic, or optionally substituted carbocyclic;

each R$_1$ is independently selected from H, halogen, hydroxy, amino, —CN, —CF$_3$, —N$_3$, —NO$_2$, —OR$_4$, —SR$_4$, —NR$_3$R$_4$, optionally substituted aryl; optionally substituted heteroaryl; optionally substituted heterocyclic; optionally substituted carbocyclic; optionally substituted haloalkyl, optionally substituted alkyl, optionally substituted alkenyl, or optionally substituted alkynyl;

G is —N(R$_3$)S(O)$_p$—;

p is 0, 1, or 2;

each of R$_{2a}$, R$_{2b}$, R$_{2c}$, and R$_{2d}$ are each independently H or F, wherein at least two of R$_{2a}$, R$_{2b}$, R$_{2c}$, and R$_{2d}$ are F;

R$_5$ is optionally substituted carbocyclic or heterocyclic;

each R$_3$ and R$_4$ is independently selected at each occurrence from the following:

optionally substituted alkyl, optionally substituted haloalkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; and n is 0, 1, 2, 3, or 4.

4. The compound of claim 3 wherein J is —C(O)—, or —O—C(O)—.

5. The compound of claim 3, wherein A is methyl, ethyl, propyl, iso-propyl, butyl, i-butyl, t-butyl, pentyl, hexyl, heptyl, phenyl, pyridyl, pyrimidyl, pyrazinyl, triazinyl, furanyl, thiophenyl, pyrrolyl, isoxazolyl, or pyrazolyl; each of which may be optionally substituted.

6. The compound of claim 3, wherein G is —N(R$_3$)S(O)$_p$— and R$_5$ is cyclopropyl, cyclobutyl, cyclopentyl, cyclohexyl, or cycloheptyl, each of which is optionally substituted.

7. The compound of claim 3, wherein R$_{2a}$ and R$_{2b}$ are F.

8. The compound of claim 3, wherein R$_{2c}$ and R$_{2d}$ are F.

9. The compound of claim 1, of formula II:

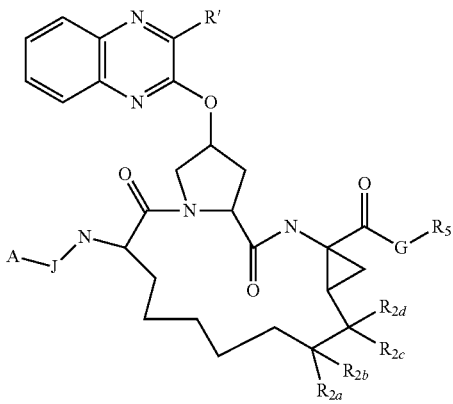

(II)

or a pharmaceutically acceptable salt, hydrate, or solvate thereof,
wherein:
J is —C(O)—, —O—C(O)—, —N(R$_3$)—C(O)—, —S(O)—, or —S(O$_2$)—;
A is optionally substituted alkyl, or optionally substituted heteroaryl, optionally substituted aryl, optionally substituted heterocyclic, or optionally substituted carbocyclic;
R' is H, optionally substituted aryl; optionally substituted heteroaryl; or optionally substituted alkyl;
G is —N(R$_3$)S(O)$_p$—;
p is 0, 1, or 2;
each of R$_{2a}$, R$_{2b}$, R$_{2c}$, and R$_{2d}$ are each independently H or F, wherein at least two of R$_{2a}$, R$_{2b}$, R$_{2C}$, and R$_{2d}$ are F;
R$_5$ is optionally substituted carbocyclic, optionally substituted heterocyclic, optionally substituted aryl, or optionally substituted heteroaryl; and
each R$_3$ and R$_4$ is independently selected at each occurrence from the following:
optionally substituted alkyl, optionally substituted haloalkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen.

10. The compound of claim 9, wherein R' is H, optionally substituted alkyl; optionally substituted aryl; or optionally substituted heteroaryl.

11. The compound of claim 9, wherein J is —C(O)—, or —O—C(O)—.

12. The compound of claim 9, wherein A is methyl, ethyl, propyl, iso-propyl, butyl, i-butyl, t-butyl, pentyl, hexyl, heptyl, phenyl, pyridyl, pyrimidyl, pyrazinyl, triazinyl, furanyl, thiophenyl, pyrrolyl, isoxazolyl, or pyrazolyl; each of which may be optionally substituted.

13. The compound of claim 9, wherein G is —N(R$_3$)S(O)$_p$—and R$_5$ is cyclopropyl, cyclobutyl, cyclopentyl, cyclohexyl, or cycloheptyl, each of which is optionally substituted.

14. The compound of claim 9, wherein R$_{2a}$ and R$_{2b}$ are F.

15. The compound of claim 9, wherein R$_{2c}$ and R$_{2d}$ are F.

16. A pharmaceutical composition comprising a therapeutically effective amount of a compound of claim 1 or a pharmaceutically acceptable salt, hydrate, or solvate thereof, in combination with a pharmaceutically acceptable carrier or excipient.

17. A method of treating an HCV viral infection in a subject, comprising administering to the subject a therapeutically effective amount of a compound of claim 1 or a pharmaceutically acceptable salt, hydrate, or solvate thereof.

18. A method of producing a compound of formula I or a pharmaceutically acceptable salt, hydrate, or solvate thereof, comprising the step of reacting a compound of formula I-a:

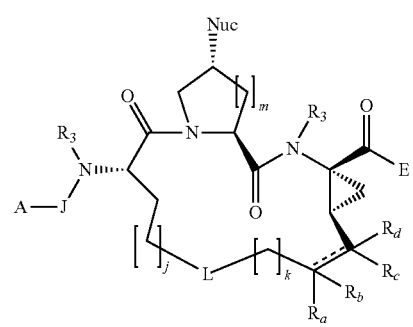

(I-a)

with a compound of formula I-b:

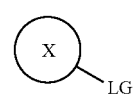

(I-b)

to arrive at a compound of formula I:

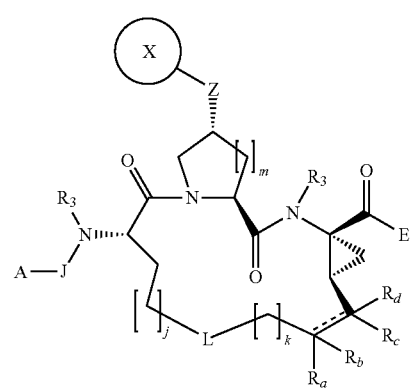

(I)

wherein:
X is

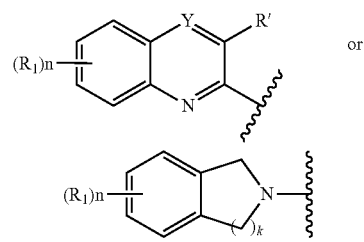

or

Y is N or —C(R")—;
wherein if Y is —C(R")—, then R' and R" taken together with the carbon atoms to which they are attached form a ring, which is optionally substituted;

R' is H, alkyl, alkenyl, alkynyl, carbocyclic, heterocyclyl, aryl, or heteroaryl, each of which may be optionally substituted;

each $R_1$ is independently selected from halogen, hydroxy, amino, —CN, —CF$_3$, —N$_3$, —NO$_2$, —OR$_4$, —SR$_4$, —SOR$_4$, —SO$_2$R$_4$, —N(R$_3$)S(O)$_2$—R$_4$, —N(R$_3$)(SO$_2$)NR$_3$R$_4$, —NR$_3$R$_4$, —C(O)—OR$_4$, —C(O)R$_4$, —C(O)NR$_3$R$_4$, —N(R$_3$)C(O)R$_4$; optionally substituted aryl; optionally substituted heteroaryl; optionally substituted heterocyclic; optionally substituted carbocyclic; optionally substituted alkyl, optionally substituted haloalkyl, optionally substituted alkenyl, or optionally substituted alkynyl, each containing 0, 1, 2, or 3 heteroatoms selected from O, S, or N;

each n is independently 0, 1, 2, 3, or 4;

Z is O, S(O)m, NRx, OC(O), C(O), C(O)O, NRxC(O), or C(O)NRx;

each Rx is independently H or alkyl;

Nuc is a nucleophile;

LG is a leaving group;

J is —C(O)—, —O—C(O)—, —C(O)O—, —N(R$_3$)—C(O)—, —C(S)—, —C(=NR$_4$)—, —N(R$_3$)—, —S(O)—, or —S(O$_2$)—or absent;

A is selected from the group consisting of the following:
  (i) H, aryl; substituted aryl; heteroaryl; substituted heteroaryl;
  (ii) heterocyclyl or substituted heterocyclyl; and
  (iii) —C$_1$-C$_8$ alkyl, —C$_2$-C$_8$ alkenyl or —C$_2$-C$_8$ alkynyl, each containing 0, 1, 2, or 3 heteroatoms independently selected from O, S, and N; substituted —C$_1$-C$_8$ alkyl, substituted —C$_2$-C$_8$ alkenyl or substituted —C$_2$-C$_8$ alkynyl, each containing 0, 1, 2, or 3 heteroatoms independently selected from O, S and N; —C$_3$-C$_{12}$ carbocyclic, substituted —C$_3$-C$_{12}$ carbocyclic; —C$_3$-C$_{12}$ cycloalkenyl, or substituted —C$_3$-C$_{12}$ cycloalkenyl;

E is —G-R$_5$;
  wherein G is absent; optionally substituted alkylene, optionally substituted alkenylene, optionally substituted alkynylene, each containing 0, 1, 2, or 3 heteroatoms selected from O, S, or N;
  or —O—, —S—, —N(R$_3$)—, —N(R$_3$)S(O$_p$)—, —N(R$_3$)C(O)—, —N(R$_3$) C(O)S(O$_p$)—, —OS(O$_p$)—, —C(O)S(O$_p$)—, or —C(O)N(R$_3$)S(O$_p$)—;

each p is independently 0, 1, or 2;

R$_5$ is H; optionally substituted alkyl, optionally substituted alkenyl, or optionally substituted alkynyl, each containing 0, 1, 2, or 3 heteroatoms selected from O, S, or N; optionally substituted carbocyclic, optionally substituted heterocyclic, optionally substituted aryl, or optionally substituted heteroaryl;

═══ denotes a carbon-carbon single or double bond (i.e.,

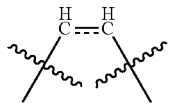

means or);

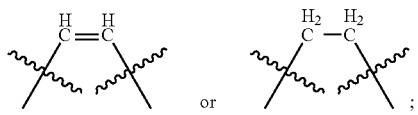

each of $R_a$, $R_b$, $R_c$, and $R_d$ are each independently H or halo, wherein at least two of $R_a$, $R_b$, $R_c$, and $R_d$ are halo; and $R_b$ and $R_d$ are absent if ═══ is a double bond each $R_3$ and $R_4$ is independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl;

optionally substituted heteroaryl; optionally substituted heterocyclic; and optionally substituted carbocyclic;

L is absent or a C$_2$-C$_5$ saturated or unsaturated chain, optionally containing one to three heteroatoms independently selected from O, N and S(O)$_q$, wherein L is optionally substituted with one or more substituents selected from halogen, hydroxy, mercapto, amino, carboxy, nitro, oxo, phosphonoxy, phosphono, thioxo, cyano, C$_1$-C$_6$alkyl, C$_2$-C$_6$alkenyl and C$_2$-C$_6$alkynyl, wherein each C$_1$-C$_6$alkyl, C$_2$-C$_6$alkenyl and C$_2$-C$_6$alkynyl, group is optionally substituted at each occurrence with one or more substituents selected from halogen, hydroxy, mercapto, amino, carboxy, nitro, oxo, phosphonoxy, phosphono, thioxo, formyl and cyano;

j = independently 0, 1, 2, 3, or 4;

k = independently 0, 1, 2, or 3;

each m is independently 0, 1, or 2; and q is independently 0, 1, or 2.

* * * * *